(12) United States Patent
Harshman et al.

(10) Patent No.: US 10,307,188 B2
(45) Date of Patent: Jun. 4, 2019

(54) SHAPE ADAPTABLE INTRAMEDULLARY FIXATION DEVICE

(71) Applicants: The University of British Columbia, Vancouver (CA); British Columbia Cancer Agency Branch, Vancouver (CA)

(72) Inventors: Edward Scott Harshman, Kirkland, WA (US); Steven Charles Dimmer, Bellevue, WA (US); Daniel Reed Baker, Seattle, WA (US); David Thomas Stinson, Woodinville, WA (US); Robert N. Meek, Vancouver (CA); Robin John Noel Coope, Vancouver (CA); Lok Tin Lam, Coquitlam (CA)

(73) Assignees: The University of British Columbia, Vancouver (CA); British Columbia Cancer Agency Branch, Vancouver (CA)

( * ) Notice: Subject to any disclaimer, the term of this patent is extended or adjusted under 35 U.S.C. 154(b) by 0 days.

(21) Appl. No.: 15/285,811

(22) Filed: Oct. 5, 2016

(65) Prior Publication Data

US 2017/0020585 A1    Jan. 26, 2017

Related U.S. Application Data

(60) Division of application No. 14/727,576, filed on Jun. 1, 2015, now Pat. No. 9,498,264, which is a (Continued)

(51) Int. Cl.
*A61B 17/72* (2006.01)
*A61B 17/16* (2006.01)
(Continued)

(52) U.S. Cl.
CPC ........ *A61B 17/7208* (2013.01); *A61B 17/164* (2013.01); *A61B 17/1717* (2013.01); (Continued)

(58) Field of Classification Search
CPC ............ A61B 17/7216; A61B 17/7225; A61B 17/7208; A61B 17/7283; A61B 17/7233; (Continued)

(56) References Cited

U.S. PATENT DOCUMENTS 4,706,659 A   11/1987   Matthews et al.
5,108,397 A   4/1992   White
(Continued)

FOREIGN PATENT DOCUMENTS

AT           509852 A4   12/2011
CN         2699846 Y    5/2005
(Continued)

OTHER PUBLICATIONS

US 7,273,482 B2, 09/2007, Dakin et al. (withdrawn)
(Continued)

*Primary Examiner* — Julianna N Harvey
(74) *Attorney, Agent, or Firm* — Fogg & Powers LLC

(57) ABSTRACT

Implantable devices for fixation of curved bone such as the pelvic ring pubic symphysis and acetabulum, and methods for the use of the devices are disclosed. The implantable devices are convertible between a flexible state and a rigid state, and include an elongate structure having a proximal bone interface, a main body, and a distal bone interface. In a flexible state, the devices may be inserted along, and conform to a curved pathway, and in the rigid state, the devices may support the mechanical loads required to fixate a fracture.

28 Claims, 44 Drawing Sheets

Related U.S. Application Data continuation of application No. PCT/US2015/018969, filed on Mar. 5, 2015.

(60) Provisional application No. 61/949,177, filed on Mar. 6, 2014.

(51) Int. Cl.
- *A61B 17/17* (2006.01)
- *A61B 17/88* (2006.01)
- *A61B 17/34* (2006.01)

(52) U.S. Cl.
CPC ...... *A61B 17/7233* (2013.01); *A61B 17/7283* (2013.01); *A61B 17/8897* (2013.01); *A61B 17/3421* (2013.01)

(58) Field of Classification Search
CPC .............. A61B 17/7241; A61B 17/725; A61B 17/7258; A61B 17/7266; A61B 17/7275; A61B 17/7291; A61B 17/72
See application file for complete search history.

(56) References Cited

U.S. PATENT DOCUMENTS

| | | |
|---|---|---|
| 5,167,665 A | 12/1992 | McKinney |
| 5,234,435 A | 8/1993 | Seagrave, Jr. |
| D346,218 S | 4/1994 | White |
| 5,300,071 A | 4/1994 | Browner et al. |
| 5,336,224 A | 8/1994 | Selman |
| 5,527,309 A | 6/1996 | Shelton |
| 5,527,310 A | 6/1996 | Cole et al. |
| 5,593,407 A | 1/1997 | Reis |
| 5,601,550 A | 2/1997 | Esser |
| 5,649,925 A | 7/1997 | Barbera Alacreu |
| 5,879,352 A | 3/1999 | Filoso et al. |
| 5,944,719 A | 8/1999 | Leban |
| 6,340,362 B1 | 1/2002 | Pierer et al. |
| 6,368,326 B1 | 4/2002 | Dakin et al. |
| 7,258,692 B2 | 8/2007 | Thelen et al. |
| 7,410,483 B2 | 8/2008 | Danitz et al. |
| 7,625,395 B2 | 12/2009 | Mückter |
| 7,632,277 B2 | 12/2009 | Woll et al. |
| 7,785,325 B1 | 8/2010 | Milbank |
| 7,846,162 B2 | 12/2010 | Nelson et al. |
| 8,043,347 B2 | 10/2011 | Jiang et al. |
| 8,128,626 B2 | 3/2012 | Justin |
| 8,128,627 B2 | 3/2012 | Justin et al. |
| 8,206,389 B2 | 6/2012 | Huebner et al. |
| 8,409,257 B2 | 4/2013 | Edidin et al. |
| 8,439,916 B2 | 5/2013 | Coati et al. |
| 8,632,543 B2 | 1/2014 | Metzinger et al. |
| 8,961,516 B2 | 2/2015 | Nelson et al. |
| 9,060,809 B2 | 6/2015 | Tipirneni et al. |
| 9,144,506 B2 | 9/2015 | Phelps |
| 9,155,574 B2 | 10/2015 | Saravia et al. |
| 9,482,260 B1 | 11/2016 | Krause |
| 9,498,264 B2 | 11/2016 | Harshman et al. |
| 9,839,435 B2 | 12/2017 | Meek et al. |
| 2002/0032444 A1 | 3/2002 | Mische |
| 2002/0087161 A1 | 7/2002 | Randall et al. |
| 2002/0198527 A1 | 12/2002 | Muckter |
| 2003/0078582 A1 | 4/2003 | Heggeness |
| 2003/0181982 A1 | 9/2003 | Kuslich |
| 2003/0187449 A1 | 10/2003 | McCleary et al. |
| 2004/0024409 A1 | 2/2004 | Sand et al. |
| 2004/0102778 A1 | 5/2004 | Huebner et al. |
| 2004/0215191 A1 | 10/2004 | Kitchen |
| 2005/0055023 A1 | 3/2005 | Sohngen et al. |
| 2005/0085819 A1 | 4/2005 | Ellis et al. |
| 2005/0154390 A1 | 7/2005 | Biedermann et al. |
| 2005/0165401 A1 | 7/2005 | Pack |
| 2006/0074421 A1 | 4/2006 | Bickley et al. |
| 2006/0264950 A1* | 11/2006 | Nelson ............... A61B 17/7208 606/916 |
| 2007/0083204 A1 | 4/2007 | Sidebotham |
| 2007/0162132 A1 | 7/2007 | Messerli |
| 2007/0233111 A1 | 10/2007 | Orbay et al. |
| 2008/0051786 A1 | 2/2008 | Jensen |
| 2008/0058722 A1 | 3/2008 | Von Oepen et al. |
| 2008/0077133 A1 | 3/2008 | Schulze |
| 2008/0077154 A1 | 3/2008 | Edwards et al. |
| 2008/0108989 A1 | 5/2008 | Parsell et al. |
| 2008/0161805 A1 | 7/2008 | Saravia et al. |
| 2008/0195145 A1 | 8/2008 | Bonutti et al. |
| 2008/0234676 A1 | 9/2008 | Schulze et al. |
| 2008/0249628 A1 | 10/2008 | Altarac et al. |
| 2008/0269745 A1 | 10/2008 | Justin |
| 2008/0287951 A1 | 11/2008 | Stoneburner et al. |
| 2008/0294164 A1 | 11/2008 | Frank et al. |
| 2009/0024174 A1 | 1/2009 | Stark |
| 2009/0048672 A1 | 2/2009 | Essenmacher |
| 2009/0062797 A1 | 3/2009 | Huebner et al. |
| 2009/0192512 A1 | 7/2009 | Sommers |
| 2009/0216232 A1 | 8/2009 | Buford, III et al. |
| 2010/0023010 A1 | 1/2010 | Nelson et al. |
| 2010/0076503 A1 | 3/2010 | Beyar et al. |
| 2010/0185290 A1 | 7/2010 | Compton et al. |
| 2010/0217333 A1 | 8/2010 | McShane et al. |
| 2010/0249832 A1 | 9/2010 | Stopek et al. |
| 2010/0249838 A1 | 9/2010 | Stopek et al. |
| 2010/0249854 A1 | 9/2010 | Thomas et al. |
| 2010/0249944 A1 | 9/2010 | Thomas et al. |
| 2010/0262239 A1 | 10/2010 | Boyden et al. |
| 2010/0286692 A1* | 11/2010 | Greenhalgh ........ A61B 17/7258 606/63 |
| 2010/0298893 A1 | 11/2010 | Stucki |
| 2010/0318137 A1 | 12/2010 | Stucki et al. |
| 2010/0331842 A1 | 12/2010 | Milbank |
| 2011/0015684 A1 | 1/2011 | Belcheva et al. |
| 2011/0028974 A1 | 2/2011 | Chemello |
| 2011/0040282 A1 | 2/2011 | Uihlein |
| 2011/0046746 A1 | 2/2011 | Rabiner et al. |
| 2011/0087227 A1 | 4/2011 | Mazur et al. |
| 2011/0098757 A1 | 4/2011 | Schelling |
| 2011/0098816 A1 | 4/2011 | Jacob et al. |
| 2011/0098817 A1 | 4/2011 | Eckhardt et al. |
| 2011/0119815 A1 | 5/2011 | Paulson et al. |
| 2011/0144643 A1 | 6/2011 | Lorenz et al. |
| 2011/0144645 A1 | 6/2011 | Saravia et al. |
| 2011/0153454 A1 | 6/2011 | Dunn et al. |
| 2011/0184518 A1 | 7/2011 | Trieu |
| 2011/0184519 A1 | 7/2011 | Trieu |
| 2011/0184520 A1 | 7/2011 | Trieu |
| 2011/0196435 A1 | 8/2011 | Forsell |
| 2011/0230966 A1 | 9/2011 | Trieu |
| 2011/0238181 A1 | 9/2011 | Trieu |
| 2011/0264229 A1 | 10/2011 | Donner |
| 2011/0288598 A1 | 11/2011 | Moed et al. |
| 2011/0306975 A1 | 12/2011 | Kaikkonen et al. |
| 2011/0319944 A1 | 12/2011 | Borodic |
| 2012/0010617 A1 | 1/2012 | Ramos Maza |
| 2012/0078252 A1 | 3/2012 | Huebner et al. |
| 2012/0078311 A1 | 3/2012 | Huebner et al. |
| 2012/0083847 A1 | 4/2012 | Huebner et al. |
| 2012/0083895 A1 | 4/2012 | Conway et al. |
| 2012/0101533 A1 | 4/2012 | Purcell et al. |
| 2012/0101576 A1 | 4/2012 | Dewey et al. |
| 2013/0006145 A1 | 1/2013 | Toomey et al. |
| 2013/0006245 A1 | 1/2013 | Stoneburner et al. |
| 2013/0012942 A1 | 1/2013 | Nelson et al. |
| 2013/0131678 A1 | 5/2013 | Dahners |
| 2013/0144348 A1 | 6/2013 | Schwappach |
| 2013/0325007 A1 | 12/2013 | Beyar et al. |
| 2014/0114312 A1 | 4/2014 | Krause |
| 2014/0309636 A1 | 10/2014 | Meek et al. |
| 2014/0358146 A1 | 12/2014 | Meek et al. |
| 2015/0157370 A1 | 6/2015 | Gross |
| 2015/0257800 A1 | 9/2015 | Harshman et al. |
| 2017/0014170 A1 | 1/2017 | Fallin et al. |

(56) References Cited

U.S. PATENT DOCUMENTS

| | | | |
|---|---|---|---|
| 2017/0020585 | A1 | 1/2017 | Harshman et al. |
| 2017/0238977 | A1 | 8/2017 | Harshman et al. |

FOREIGN PATENT DOCUMENTS

| | | | |
|---|---|---|---|
| CN | 101633119 A | 1/2010 | |
| CN | 102793579 A | 11/2012 | |
| CN | 104203132 A | 12/2014 | |
| CN | 104203132 B | 8/2017 | |
| CN | 107106217 A | 8/2017 | |
| EP | 2779928 A1 | 9/2014 | |
| EP | 3326558 A1 | 5/2018 | |
| EP | 3206608 | 7/2018 | |
| WO | 2007009123 A2 | 1/2007 | |
| WO | 2008116175 A2 | 9/2008 | |
| WO | 2008120877 A1 | 10/2008 | |
| WO | 2009143374 A2 | 11/2009 | |
| WO | 2010124230 A1 | 10/2010 | |
| WO | 2011067668 A1 | 6/2011 | |
| WO | 2011119815 A2 | 9/2011 | |
| WO | 2011153454 A2 | 12/2011 | |
| WO | 2012107913 A2 | 8/2012 | |
| WO | 2013071432 A1 | 5/2013 | |
| WO | 2016061173 A1 | 4/2016 | |
| WO | 2018067888 A1 | 4/2018 | |

OTHER PUBLICATIONS

Canada Intellectual Property Office, "Office Action for CA Application No. 2,855,752", "Foreign Counterpart to U.S. Appl. No. 14/357,917", dated Mar. 9, 2018, pp. 1-5, Published in: CA.

Canadian Intellectual Property Office, "Office Action for CA Application No. 2,855,752", "Foreign Counterpart to U.S. Appl. No. 14/357,917", dated Feb. 3, 2017, pp. 1-4, Published in: CA.

Canadian Intellectual Property Office, "Office Action for CA Application No. 2,855,752", "Foreign Counterpart to U.S. Appl. No. 14/357,917", dated Oct. 28, 2015, pp. 1-4, Published in: CA.

Canadian Intellectual Property Office, "Office Action from CA Application No. 2,964,370 dated May 4, 2018", from Foreign Counterpart to PCT Application No. PCT/US2015/055441, May 4, 2018, pp. 1-7, Published: CA.

European Patent Office, "Communication under Rule 71(3) for EP Application No. 12849005.9", Foreign Counterpart to U.S. Appl. No. 14/357,917, dated Jul. 25, 2017, pp. 1-6, Published in: EP.

European Patent Office, "Communication Pursuant to Article 94(3) for EP Application No. 12849005.9", Foreign Counterpart to U.S. Appl. No. 14/357,917, dated Jun. 2, 2016, pp. 1-4, Published in: EP.

European Patent Office, "Communication pursuant to Article 94(3) from EP Application No. 12849005.9 dated Nov. 25, 2016", from Foreign Counterpart to PCT Application No. PCT/CA2012/050808, Nov. 25, 2016, pp. 1-4, Published: EP.

European Patent Office; "Extended European Search Report from EP Application 15850096.7 dated Jun. 8, 2018"; from Foreign Counterpart of U.S. Appl. No. 15/519,148; dated Jun. 8, 2018; pp. 1-12; Published: EP.

European Patent Office; "Extended European Search Report from EP Application No. 17207050.0 dated Apr. 20, 2018" from Foreign Counterpart of U.S. Appl. No. 14/357,917; pp. 1-6; Date Apr. 20, 2018; Published: EP.

International Bureau, "International Preliminary Report on Patentability from PCT Application No. PCT/CA2012/050808 dated May 20, 2014", from Foreign Counterpart to U.S. Appl. No. 14/357,917, May 20, 2014, pp. 1-6, Published: Switzerland.

International Searching Authority, "International Search Report and Written Opinion from PCT Application No. PCT/US2017/055442 dated Dec. 11, 2017", Dec. 11, 2017, pp. 1-14, Published: US.

IP Australia, "Notice of acceptance for patent application from AU Application No. 2015333623 dated Jul. 20, 2018", from Foreign Counterpart to PCT Application No. PCT/US2015/055441, Jul. 20, 2018, pp. 1-3, Published: AU.

IP Australia, "Notice of Acceptance from AU Application No. 2012339536 dated Jan. 28, 2016", from Foreign Counterpart to PCT Application No. PCT/CA2012/050808, Jan. 28, 2016, pp. 1-3, Published: AU.

IP Australia, "Patent Examination Report No. 1 for AU Application No. 2012339536", Foreign Counterpart to U.S. Appl. No. 14/357,917, dated Jan. 23, 2015, pp. 1-5, Published in: AU.

IP Australia, "Patent Examination Report No. 2 for AU Application No. 2012339536", Foreign Counterpart to U.S. Appl. No. 14/357,917, dated Oct. 16, 2015, pp. 1-6, Published in: AU.

IP Australia; " Examination report No. 1 for standard patent application from AU Application No. 2015333623 dated Sep. 26, 2017"; from Foreign Counterpart of U.S. Appl. No. 15/519,148; Dated Sep. 26, 2017; pp. 1-4; Published: AU.

Japanese Patent Office, "Decision to Grant from JP Application No. 2017519539 dated Jul. 31, 2018", from Foreign Counterpart to PCT Application No. PCT/US2015/055441, Jul. 31, 2018, pp. 1-3, Published: JP.

Japanese Patent Office, "Office Action from JP Application No. 2017519539 dated Jan. 10, 2018", from Foreign Counterpart to PCT Application No. PCT/US2015/055441, Jan. 10, 2018, pp. 1-6, Published: JP.

State Intellectual Property Office of P.R. China, "Notification on Grant of the Patent Right for Invention from CN Application No. 2012800661802 dated Apr. 28, 2017", from Foreign Counterpart to PCT Application No. PCT/CA2012/050808, Apr. 28, 2017, pp. 1-3, Published: CN.

State Intellectual Property Office of the People'S Republic of China, "Search Report for CN Application No. 201280066180.2 dated Aug. 10, 2016", Foreign Counterpart to U.S. Appl. No. 14/357,917, Aug. 10, 2016, pp. 1-3.

State Intellectual Property Office, P.R. China, "First Office Action for CN Application No. 201280066180.2 dated Dec. 28, 2015 (English language explanation of relevance included)", Foreign Counterpart to U.S. Appl. No. 15/952,093, Dec. 28, 2015, pp. 1-7, Published in: CN.

State Intellectual Property Office, P.R. China, "Second Office Action for CN Application No. 201280066180.2 dated Aug. 3, 2016 (English language explanation of relevance included)", "Foreign Counterpart to U.S. Appl. No. 15/952,093", Aug. 3, 2016, pp. 1-6, Published in: CN.

State Intellectual Property Office, P.R. China, "Third Office Action for CN Application No. 201280066180.2 dated Jan. 5, 2017 (English language explanation of relevance included)", Foreign Counterpart to U.S. Appl. No. 15/952,093, Jan. 5, 2017, pp. 1-4, Published in: CN.

U.S. Patent and Trademark Office, "Restriction Requirement for U.S. Appl. No. 14/357,917", dated Jan. 21, 2016, pp. 1-6, Published in: US.

U.S. Patent and Trademark Office, "Advisory Action for U.S. Appl. No. 14/300,752", dated Oct. 7, 2015, pp. 1-3, Published in: US.

U.S. Patent and Trademark Office, "Advisory Action for U.S. Appl. No. 14/300,752", dated Feb. 16, 2017, pp. 1-3, Published in: US.

U.S. Patent and Trademark Office, "Final Office Action for U.S. Appl. No. 14/300,752", dated Jan. 12, 2018, pp. 1-18, Published in: US.

U.S. Patent and Trademark Office, "Final Office Action for U.S. Appl. No. 14/300,752", dated Nov. 3, 2016, pp. 1-15, Published in: US.

U.S. Patent and Trademark Office, "Final Office Action for U.S. Appl. No. 14/300,752", dated May 28, 2015, pp. 1-14, Published in:US.

U.S. Patent and Trademark Office, "Final Office Action for U.S. Appl. No. 14/357,917", dated Sep. 6, 2016, pp. 1-11, Published in: US.

U.S. Patent and Trademark Office, "Interview Summary" U.S. Appl. No. 14/727,576, dated Feb. 17, 2016, pp. 1-4, Published: US.

U.S. Patent and Trademark Office, "Interview Summary", U.S. Appl. No. 14/727,576, dated Jun. 14, 2016, pp. 1-3, Published: US.

U.S. Patent and Trademark Office, "Notice of Allowance for U.S. Appl. No. 14/357,917", dated Jul. 26, 2017, pp. 1-5, Published in: US.

(56) References Cited

OTHER PUBLICATIONS

U.S. Patent and Trademark Office, "Notice of Allowance" U.S. Appl. No. 14/727,526, dated Jul. 19, 2016, pp. 1-8, Published: US.
U.S. Patent and Trademark Office, "Office Action for U.S. Appl. No. 14/300,752", dated Aug. 8, 2017, pp. 1-16, Published in: US.
U.S. Patent and Trademark Office, Office Action for U.S. Appl. No. 14/300,752, dated Apr. 5, 2016, pp. 1-16, Published in: US.
U.S. Patent and Trademark Office, "Office Action for U.S. Appl. No. 14/357,917", dated Apr. 18, 2016, pp. 1-10, Published in: US.
U.S. Patent and Trademark Office, "Office Action", U.S. Appl. No. 14/300,752, dated Oct. 20, 2014, pp. 1-14, Published: US.
U.S. Patent and Trademark Office, "Office Action", U.S. Appl. No. 14/727,576, dated Oct. 16, 2015, pp. 1-14, Published: US.
U.S. Patent and Trademark Office, "Office Action", U.S. Appl. No. 14/727,576, dated Apr. 28, 2016, pp. 1-15, Published: US.
U.S. Patent and Trademark Office, "Restriction Requirement", U.S. Appl. No. 14/727,576, dated Jul. 23, 2015, pp. 1-10, Published: US.
U.S. Patent and Trademark Office, "Restriction Requirement", U.S. Appl. No. 15/285,811, dated Mar. 30, 2018, pp. 1-7, Published: US.
U.S. Patent and Trademark Office; "Office Action"; U.S. Appl. No. 15/519,148; dated Jul. 26, 2018; pp. 1-38; Published: US.
Novick, N., "Pelvic Fractures/Acetabular Fractures—An Interview with Dr. David L. Helfet," Hospital for Special Surgery, accessed at http://www.hss.edu/conditions—pelvic-acetabulum-fractures.asp, Mar. 30, 2006, 10 pages.
"UT Southwest Medical Surgeons Market Pelvic Fracture Device," Texas Business, accessed at https://web.archive.org/web/20120531221302/http://www.texasbusiness.com/ut-southwest-medical-surgeons-market-pelvic-fracture-device-cms-4418, posted on Apr. 22, 2011, pp. 5.
Cheung, K.M., et al., "A New Halo-Pelvic Apparatus," SPINE, vol. 28, No. 3, pp. 305-308 (2003).
Extended European Search Report for European Patent Application No. 12849005.9, dated Jun. 15, 2015, pp. 6.
International Search Report and Written Opinion for International Application No. PCT/US2015/055441 dated Feb. 9, 2016, pp. 12.
International Search Report and Written Report for International Application No. PCT/CA2012/050808 dated Feb. 26, 2013, pp. 10.
Helfet, D.L., "Pelvic Fractures/Acetabular Fractures," Hospital for Special Surgery, accessed at https://web.archive.org/web/20131103011942/http://www.hss.edu/conditions_pelvic-fractures-acetabular-fractures.asp, posted on Mar. 30, 2006, pp. 9.
Barry, M., and Paterson, J.M.H., "Flexible intramedullary nails for fractures in children," The Journal of Bone & Joint Surgery (Br), vol. 86-B, No. 7, pp. 947-953 (Sep. 2004).
Ganz, R., et al., "Surgical dislocation of the adult hip," The Journal of Bone & Joint Surgery (Br), vol. 83-B, No. 8, pp. 1119-1124 (Nov. 2001).
Griffin, D.R., et al., "Vertically unstable pelvic fractures fixed with percutaneous iliosacral screws: does posterior injury pattern predict fixation failure?.," Journal of Orthopaedic Trauma, vol. 20, No. 1 (Supplement), pp. S30-S36 (Jan. 2006).
International Search Report and Written Opinion for International Application No. PCT/US2015/018969 dated May 27, 2015, pp. 5.
Miller, A.N., and Routt, M.L.C.Jr., "Variations in Sacral Morphology and Implications for Iliosacral Screw Fixation," Journal of the American Academy of Orthopaedic Surgeons, vol. 20, No. 1, pp. 8-16 (Jan. 2012).
Starr, A.J., and Malekzadeh, A.S., "Fractures of the Pelvic Ring," in Rockwood & Green's Fractures in Adults, Chapter-41, pp. 1-40, 6th Edition, Lippincott Williams & Wilkins (2006).
Starr, A.J., et al., "Superior pubic ramus fractures fixed with percutaneous screws: what predicts fixation failure?," Journal of Orthopaedic Trauma, vol. 22, No. 2, pp. 81-87 (Feb. 2008).
Vaidya, R., et al., "Complications of Anterior Subcutaneous Internal Fixation for Unstable Pelvis Fractures: A Multicenter Study," Clinical Orthopaedicsand Related Research, vol. 470, No. 8, pp. 2124-2131 (Aug. 2012).
U.S. Patent and Trademark Office, "Notice of Allowance", U.S. Appl. No. 15/519,148, dated Feb. 13, 2019, pp. 1-42, Published: US.
Canadian Intellectual Property Office, "Office Action from CA Application No. 2,964,370 dated Jan. 24, 2019", from Foreign Counterpart to U.S. Appl. No. 15/519,148, Jan. 24, 2019, pp. 1-6, Published: CA.
China National Intellectual Property Office, "Office Action from CN Application No. 201580061380.2 dated Dec. 21, 2018", from Foreign Counterpart to U.S. Appl. No. 15/519,148, Dec. 21, 2018, pp. 1-18, Published: CN.
Canadian Intellectual Property Office, "Office Action from CA Application No. 2978697 dated Oct. 19, 2018", from Foreign Counterpart to PCT Application No. PCT/US2015/018969, Oct. 19, 2018, pp. 1-4, Published: CA.

\* cited by examiner

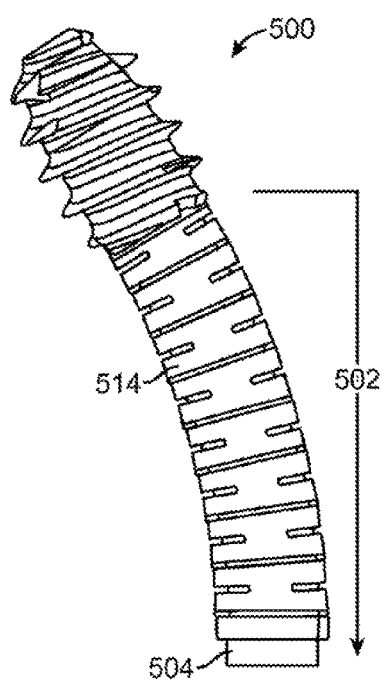
FIG. 5A
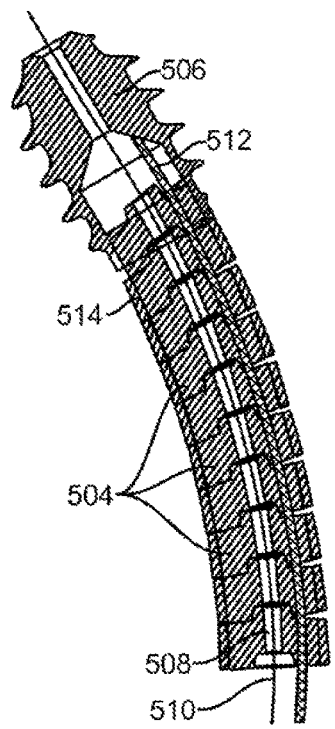
FIG. 5B
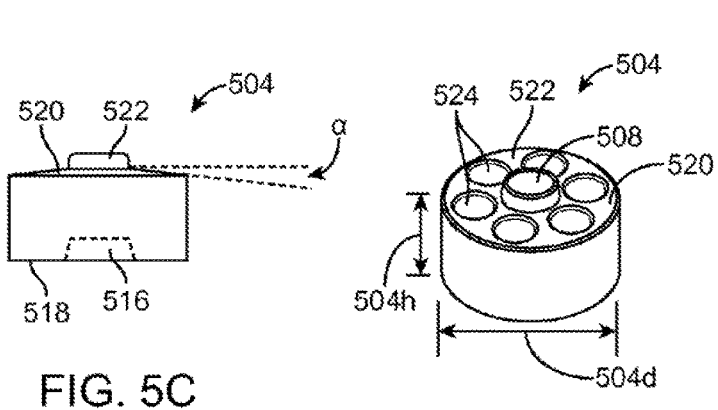
FIG. 5C
FIG. 5D
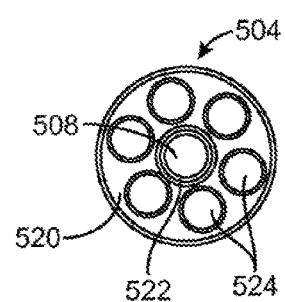
FIG. 5E

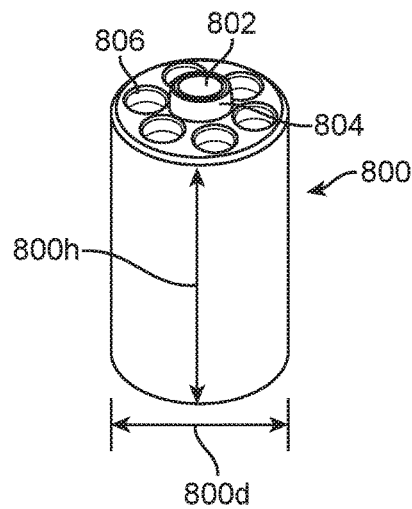
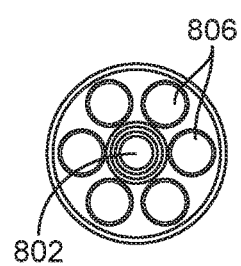
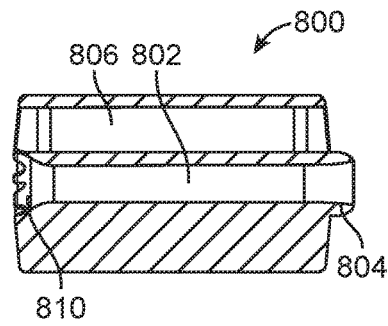
FIG. 8A　　FIG. 8B　　FIG. 8C
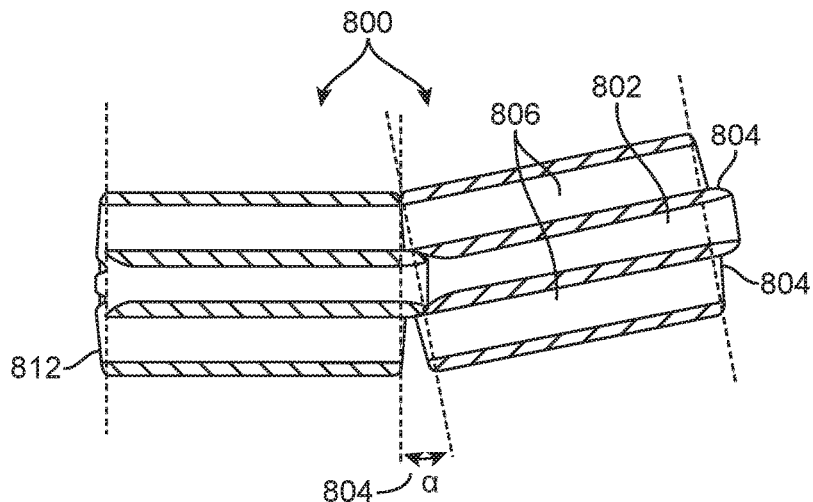
FIG. 8D

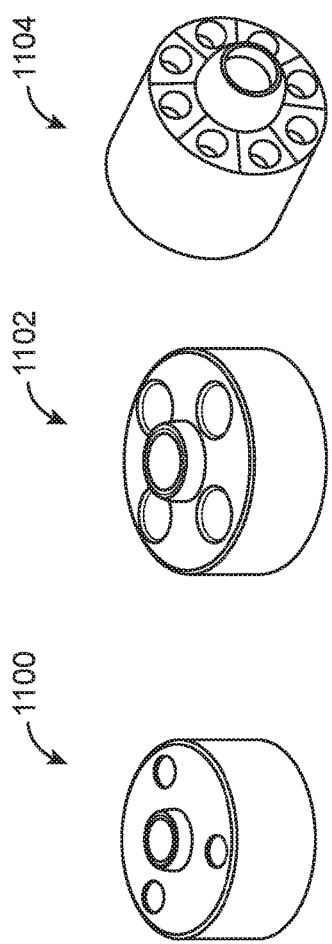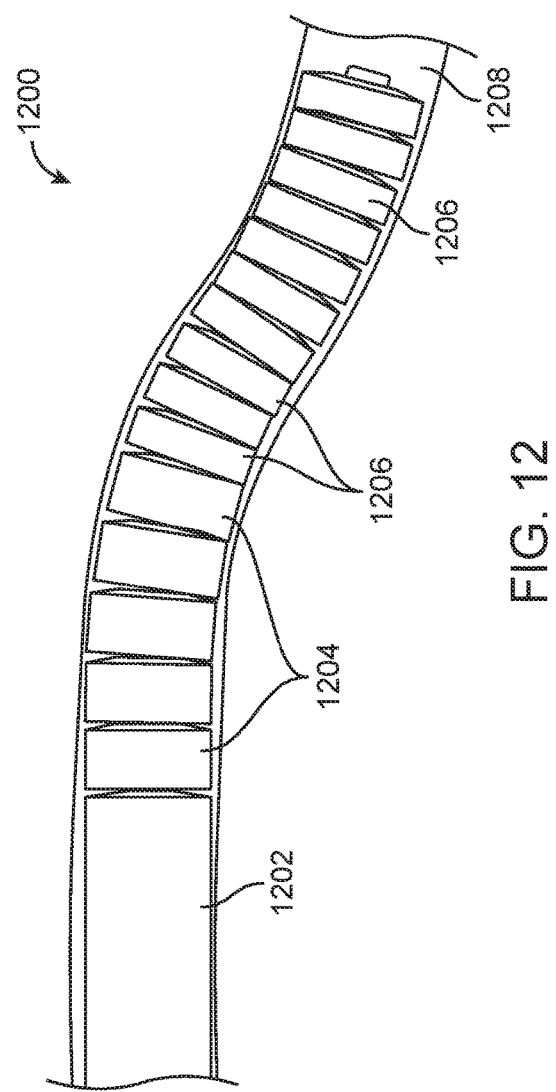

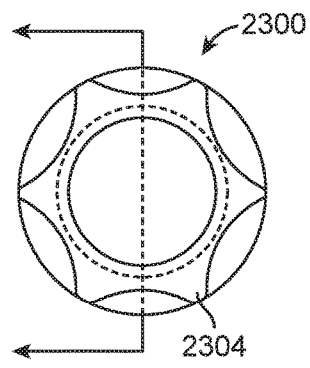
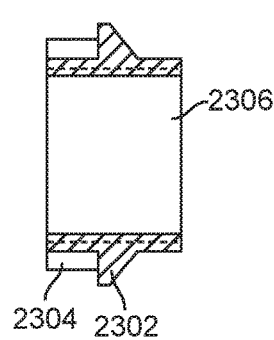
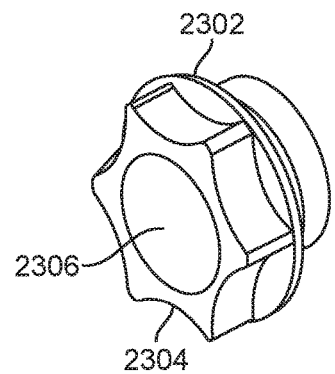
FIG. 23A   FIG. 23B   FIG. 23C
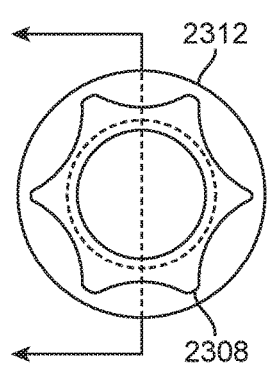
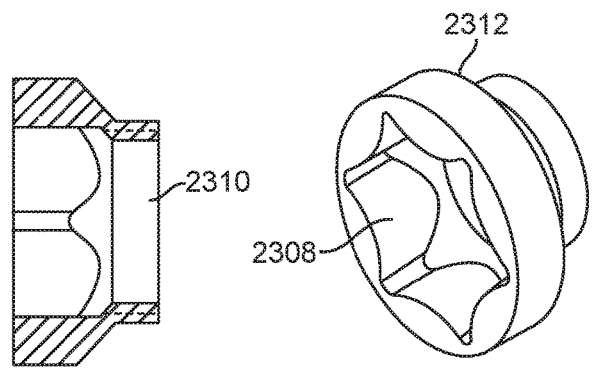
FIG. 23D   FIG. 23E   FIG. 23F

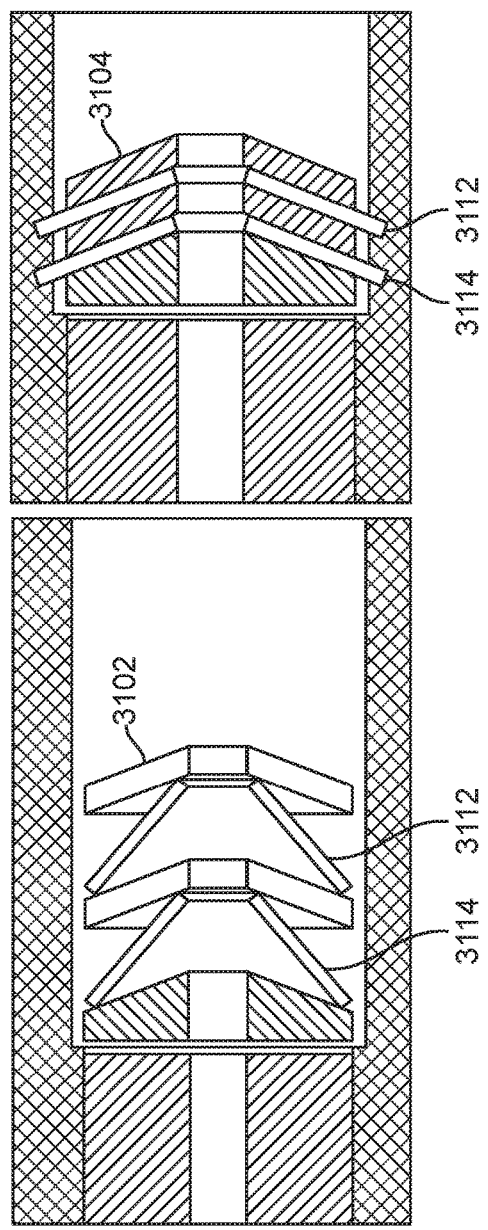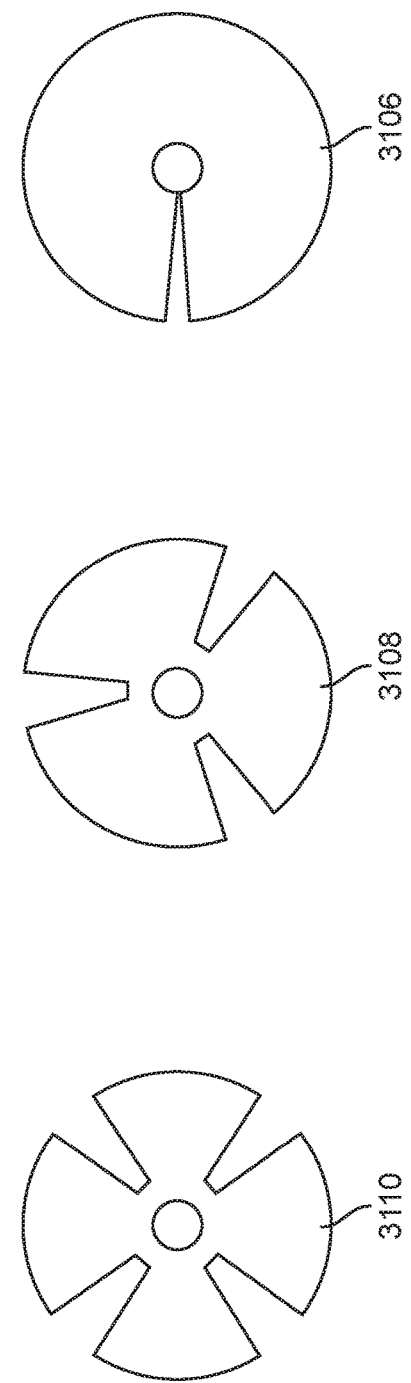
FIG. 31

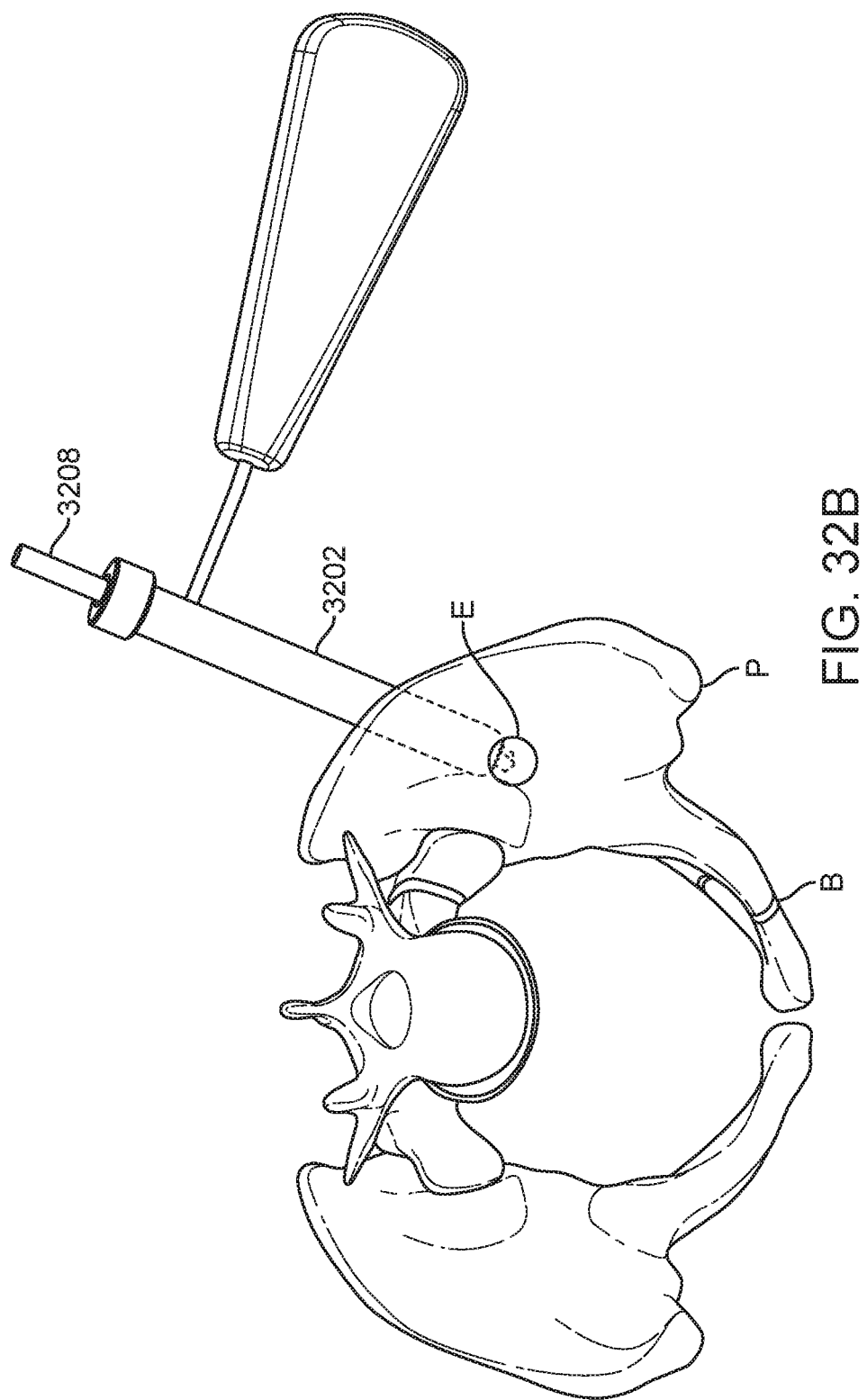

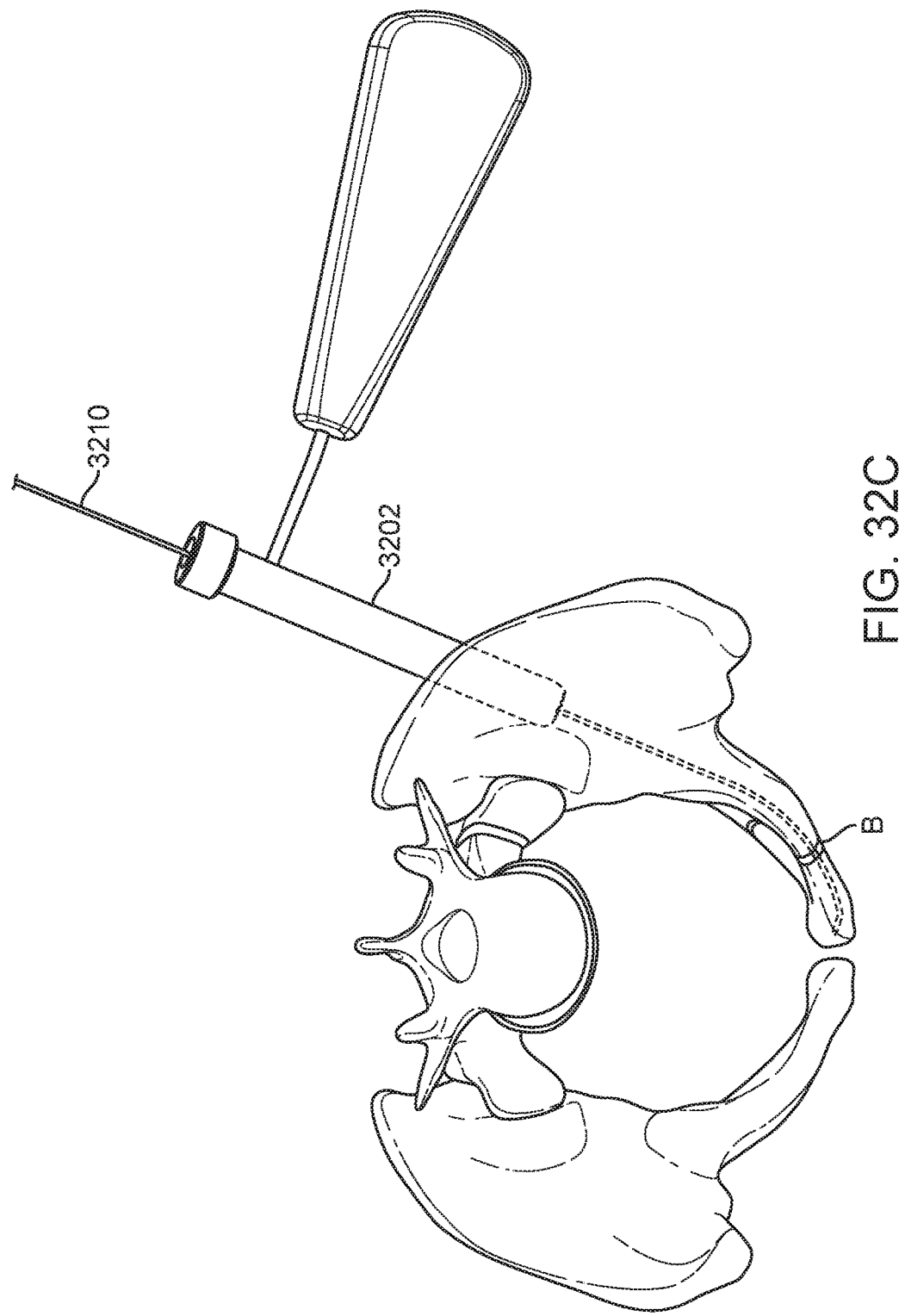

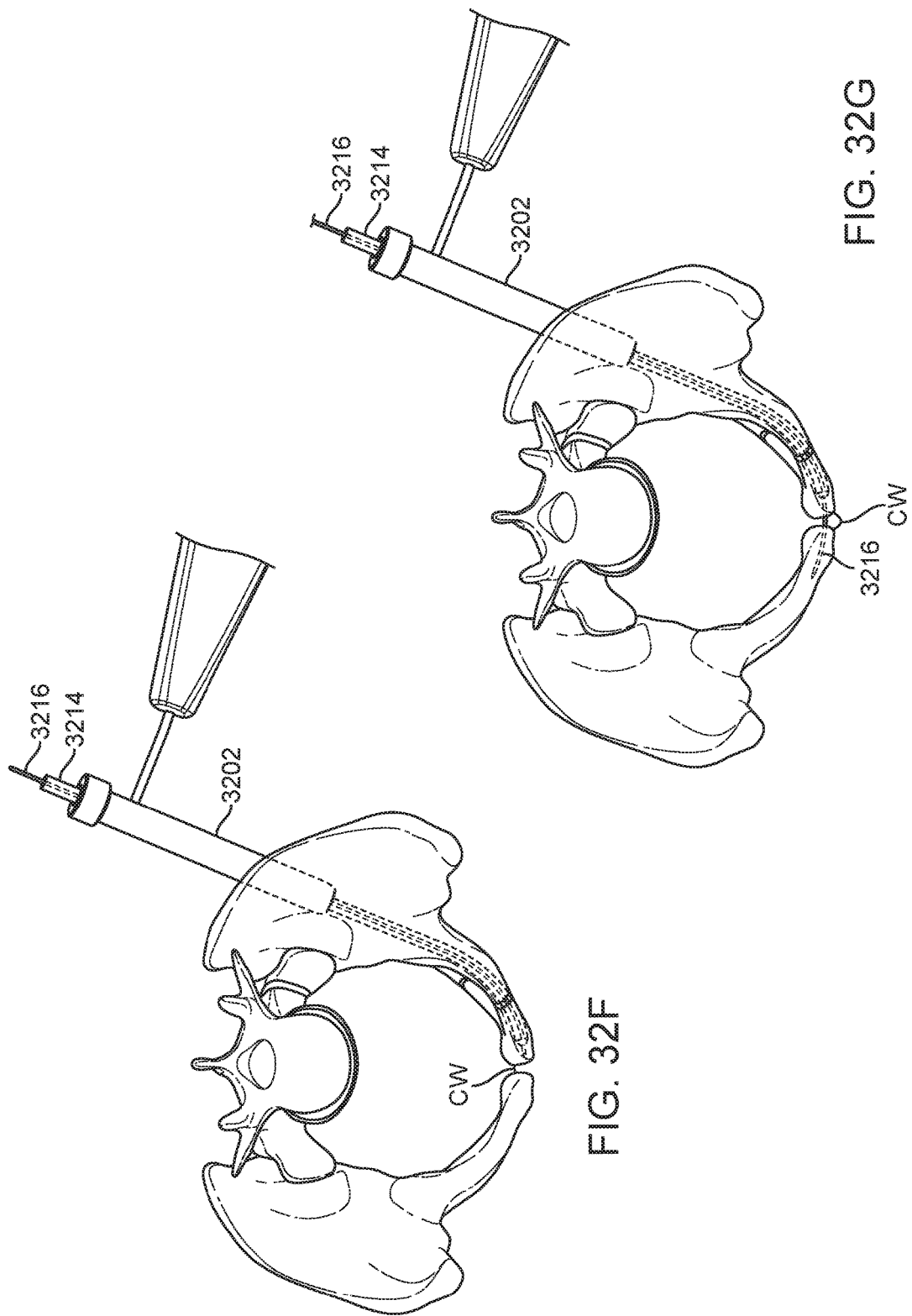

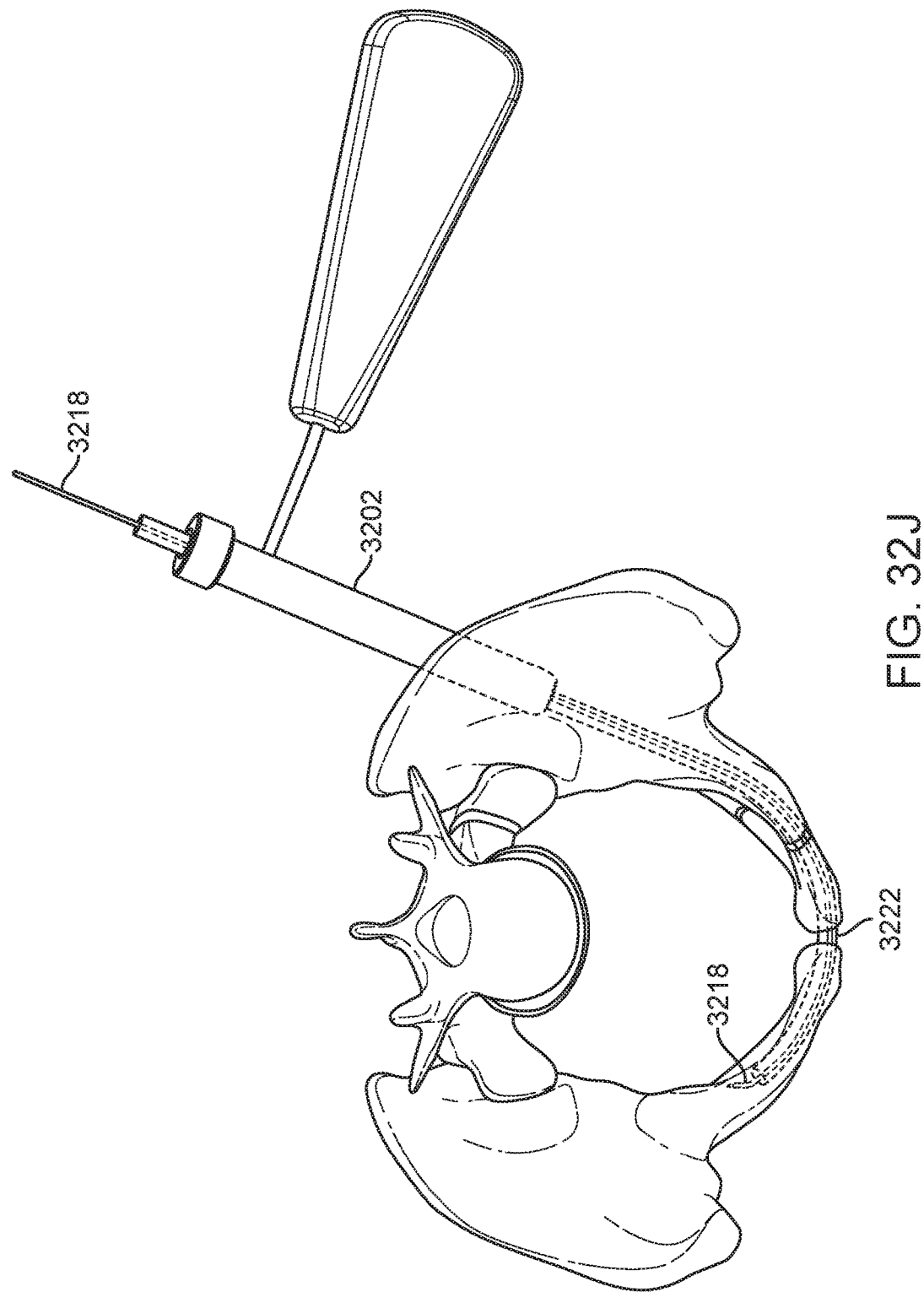

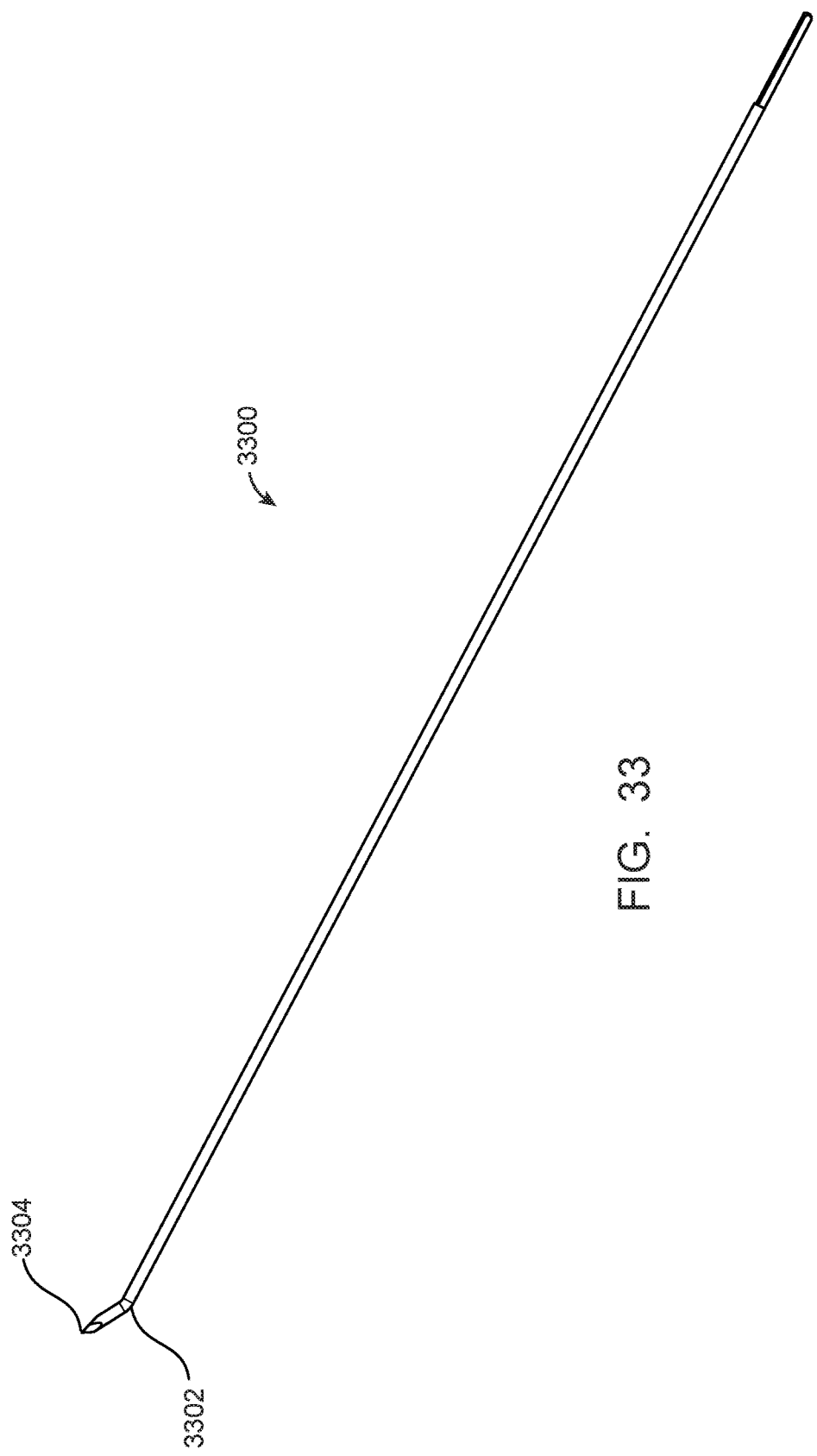

SHAPE ADAPTABLE INTRAMEDULLARY FIXATION DEVICE

CROSS-REFERENCE TO RELATED APPLICATIONS

This application is a divisional application under 35 U.S.C. § 121 of U.S. application Ser. No. 14/727,576, filed on Jun. 1, 2015, which is a continuation under 35 U.S.C. §§ 365(c) and 120 of International Application No. PCT/US2015/018969, filed on Mar. 5, 2015, which claims priority to U.S. Provisional Application No. 61/949,177, filed on Mar. 6, 2014, which are each incorporated herein by reference in their entirety for any and all purposes.

BACKGROUND

Bone fractures may occur in straight bones, such as the femur, or in curved bones, such as pelvic bones. Repairing a bone fracture generally involves two steps: fracture reduction and fracture fixation. Reduction is the step of reducing the fracture by minimizing the distance between the bone fragments and aligning the bones anatomically to minimize deformity after healing. Both surgical and nonsurgical reduction methods exist. Fixation is the step of holding the bone fracture fragments mechanically stable and in close proximity to each other to promote bone healing which may take several weeks or more, depending on the type of fracture, type of bone and the general health of the patient suffering the injury.

Fixing bone fracture fragments in a mechanically stable manner to eliminate motion across the fracture site also minimizes pain when patients apply weight across the fracture during everyday activities like sitting or walking. Fixation of bone fractures may be accomplished by either internal or external fixation. Internal fixation is defined by mechanically fixing the bone fracture fragments with implanted devices. Examples of internal fixation include bone screws inserted within the bone across the fracture site and bone plates which are applied to the surface of the bone across the fracture site. Bone plates are typically attached to healthy bone using two or more bone screws.

External fixation is defined by methods and devices which mechanically fix the bone fracture fragments with devices or methods external to the body. The traditional use of a splint or cast are examples of external fixation of a fractured bone. An example of an invasive external fixation device uses long screws that are inserted into bone on each side of the fracture. In pelvic fracture work the use of external skeletal fixation is common and involves placing long threaded pins into the iliac bones and then connecting them with an external frame. These screws are connected to a frame which is located outside the body.

Invasiveness of both fracture reduction and fixation steps varies depending on the devices and/or methods used. Invasive open reduction typically involves surgically dissecting to allow access the bone fracture. Dissection is performed through the skin, fat, and muscle layers, while avoiding injury to adjacent structures such as nerves, major blood vessels, and organs. Once dissection has been completed, the fracture may be reduced prior to definitive fixation and provisionally held using surgical clamps or other methods. Non-invasive closed reduction is typically performed by applying force to the patient's skin surface at different locations and/or to apply traction to a leg, to reduce the fracture. Minimally invasive reduction techniques minimize the surgical dissection area by reducing the size of the surgical wound and by directly pushing on the bone with various long handled tools through the minimal surgical wound. Invasive open fixation typically involves surgically dissecting to allow access to sufficient areas of healthy bone so that fixation devices such as surgical plates can be attached directly to the bone surface to fix the fracture site. Minimally invasive closed fixation typically involves insertion of a device such as a bone screw or intramedullary rod (or nail) within the bone through a small incision in the skin, fat, and muscle layers.

Minimally invasive reduction and fixation are typically used to repair long bone injuries such as the femur. One example is an intramedullary rod, also known as an intramedullary nail (IM nail), inter-locking nail or Küntschner nail. Intramedullary nails in the femur and tibia are load sharing devices and can well resist large bending and shearing forces, thereby allowing patients to leave hospital and manage with crutches in a short time.

The mechanical strength of bone fixation is determined by both the strength of the implant and strength of the implant's attachment to healthy bone. The mechanical forces applied across the fracture during the healing process can include shear, compression, tension (tensile), torsion, static loading and dynamic loading. In bones with complex curvature such as bones of the pelvis (FIG. 1) or of the spine, straight intramedullary fixation devices have limitations. Bone curvature limits the mechanical strength of attaching a straight intramedullary fixation device within healthy bone tissue. In pelvic and acetabular fracture fixation, and example of a straight intramedullary device is a commonly used cannulated bone screw. These screws must be limited in length and diameter because they are a straight device in a curved tunnel. If too long they will penetrate the bone and could injure important soft tissues. However, such screws may not offer secure fixation due to their low tensile pull out forces in cortical cancellous and/or osteoporotic bone during the healing process. Also, the diameter of the straight intramedullary screw, when in a curved bone, is significantly smaller than the thickness of the cancellous bone layer between the two outer cortical bone layers. Since the cancellous bone is significantly weaker than cortical bone (and can have significantly compromised strength in the case of osteoporotic bone) straight intramedullary screws may allow for the bone fragments to move relative to each other due to inadequate vertical shear holding force of cancellous bone. Plates normally act, mechanically, as tension band plates, neutralization plates or compression plates. Often a single plate will perform more than one of these mechanical functions, but since the plates are attached to the bone, the use of plates requires invasive open surgery to expose the bone. The plates are inherently weak because they have to be designed to be thin and have notches in them so that they can be bent to fit the curves of the pelvis. Invasive open surgery can result in increased blood loss, increased risk of infection and increased healing time compared to minimally invasive methods.

SUMMARY

Difficult mechanical fixation issues associated with fixation of curved bones such as are found in the pelvic ring and around the acetabulum, may be minimized or eliminated by using implantable devices that may be convertible between a flexible and a rigid state. These devices may include an elongate structure, a proximal bone interface, a main body, and a distal bone interface. In a flexible state, the device may be inserted inside, and conform to a curved pathway, and in the rigid state, the device may support the tensile and vertical shear mechanical loads required to fix fractured bone segments. The insertion process may involve screwing the device into bone. Other embodiments are sufficiently flexible to be inserted inside a curved path and sufficiently rigid after implantation without requiring a flexible-to-rigid conversion step. A fixation system may include the curved intramedullary fixation device, a guide wire, a reamer, and an extraction tool. Methods of use may include usages of a curved intramedullary fixation device for fixation of pelvic ring and acetabular fractures, intramedullary guide wire placement within curved bone, curved intramedullary fixation device implantation over a guide wire, intramedullary fixation device attachment to bone at implant distal end, intramedullary fixation device attachment to bone at proximal end, and in some embodiments device conversion between flexible and rigid states. In an embodiment, there is a medical apparatus for bone fixation. The apparatus has a flexible body defining a main axis. The flexible body has a proximal end and a distal end. The flexible body is made up of several individual segments having a mechanical engagement structure for non-rigidly interlocking the individual segments together. The segments have a plurality of channels or apertures arranged to generally form two or more lumens in the flexible body when the segments are in non-rigid mechanical engagement. The individual segments may move relative to each other in a first and a second orthogonal plane relative to the main axis. The medical apparatus has a torque transmission member positioned substantially on the proximal end. There is a bone engagement feature positioned substantially on the distal end. There are one or more fibers extending through the lumens such that the fibers provide a fixed shape to the flexible body when the fibers are fixed into position.

In an embodiment, there is a medical device for bone fixation, the device has an elongate tubular body defining a first axis, the body having a proximal end, a distal end and a lumen there through. The tubular body has a series of slots, cuts or apertures in it. There is a torque transmission member located generally at the proximal end. There is a bone engagement feature located generally at the distal end. The series of slots, cuts or apertures provide stress relief along the elongate body when the tubular body is under torque.

In an embodiment, there is a medical device for fixation of fractured bone, the device has an elongated body defining a longitudinal axis, and having a proximal end and a distal end spaced longitudinally from the proximal end by a first distance. There is a flexible body portion extending along at least a portion of the first distance, the flexible body portion has a plurality of interconnected segments. Each segment of the interconnected segments defines an axis portion of the longitudinal axis, and each segment is movable with respect to at least one adjacent segment to angularly offset the axis portion of each segment with the axis portion of the at least one adjacent segment. There is a transmission member positioned adjacent the proximal end for axially inserting the elongated body into the bone. There is a bone engagement device positioned adjacent the distal end for axially retaining the elongated body within the bone. There are two or more fibers disposed longitudinally within the elongated body through at least the flexible body portion in circumferentially spaced relation to one another. There is a fiber tensioning system for tensioning individual fibers of the two or more fibers to retain the interconnected segments in a fixed relationship with each other, and the fibers with one another.

In another embodiment, there is a method of fixing a reduced bone fracture in a curved bone. The method involving creating an entry into a curved bone, advancing a guidewire through an intramedullary space to a position distal to a reduced bone fracture, reaming a channel in the intramedullary space along the length of the guidewire, advancing a curved intramedullary fixation device through the channel and locking the curved intramedullary fixation device in place.

BRIEF DESCRIPTION OF THE FIGURES

FIGS. 5A-5E provide various illustrations of device segments.
FIGS. 8A-8D provide an illustration of an alternative segment and segment arrangement.
FIGS. 11A-11C provide alternative embodiments of segments.
FIG. 12 illustrates a segment stack using different kinds of segments.
FIGS. 23A-23F provide various alternative embodiments of proximal end sections.
FIG. 31 provides an alternative embodiment of a distal end.
FIGS. 32A-32L illustrate a method of fixing a reduced bone fragment.
FIG. 33 illustrates a curved guidewire.

DETAILED DESCRIPTION

Figure 1A:
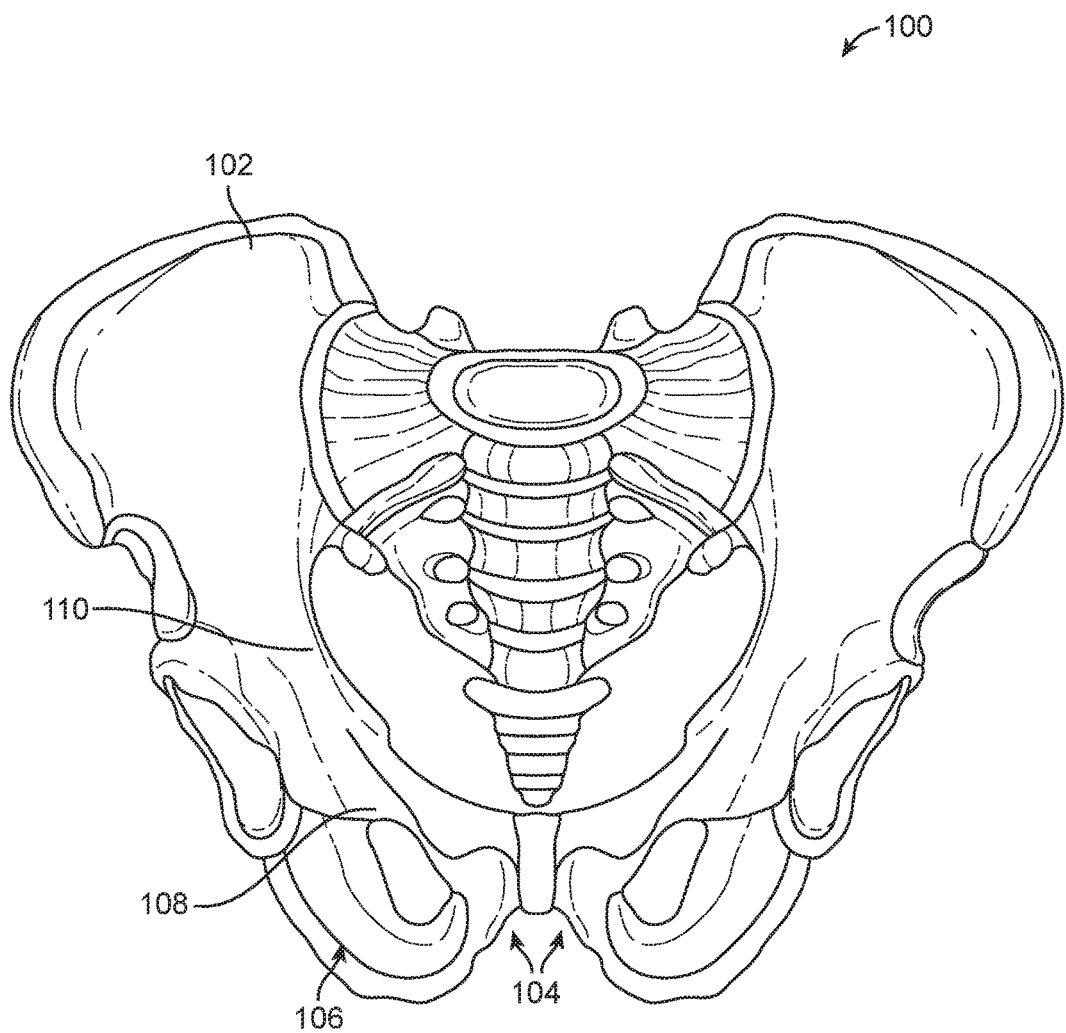
FIGS. 1A-1B depict the human pelvis.

Described herein are various embodiments for the fixation of fractured or broken bones. The systems, apparatus and methods described herein may be used on long and straight bones, but are designed specifically to treat curved bones. Curved bones may be generally straight with a section having a curve or arc length, generally curved without a distinguishable straight segment, or a combination of the two. Curved bones or non-linear bones include the zygoma, mandible (jaw bone), clavicle, scapula (the hemipelvis of the upper limb), ribs, spine, talus and calcaneus. The device may also have some applications in pediatric long bones.

Treatment of an injury or weakness in these curved bones may involve the use of a bone reinforcement structure for deployment within the bones soft interior (marrow or bone channel). The use of straight intramedullary nails and bone screws and plates are well known and often used for straight bones. Curved intramedullary nails are used in the humerus and clavicle bones to reduce the invasiveness of the implantation procedure. However, curved intramedullary nails are not used in the pelvis because the curvature of the pelvis varies significantly depending on the size of the patient and the location of the fracture(s). Therefore, the deployment of a curved nail into curved pelvis bones would be fraught with inherent difficulties, such as matching the curvature of the nail to the bone, penetrating the nail through the desired path in the bone without piecing the cortical bone and thus further weakening the bone structure, visualizing the deployment path, visualizing the placement in real time and removing the nail from the patient in the event the nail needs to be withdraw post procedure for any variety of reasons. Another problem with trying to put a preformed curved nail into the pelvic ring or anterior or posterior columns of the acetabulum is the paths formed are complex S shaped. To get the preformed device past the first part of the complex S into the second part is impossible. The complex S shaped curves are three dimensional S's and have more than one S curve in them.

In the discussion of the various systems, devices and methods herein, references and orientation are made to facilitate the understanding of the described embodiment. The term "proximal" as used herein means the side or end of a device that tends to be the closest to the physician or operator when using the described embodiment. Alternatively "proximal" means the side or end of an embodiment that is the last to enter a patient body. The term "distal" refers to the end or side of the embodiment that is furthest away from the physician or operator. The term distal may alternatively mean the end or side of the embodiment that is first to enter the patient body. Several embodiments also make reference to a general axis. This axis is an imaginary axis based on the shape of some of the embodiments of the device and refers to the long axis of the embodiments having one dimension (of height, length or width) clearly longer or greater than the other two dimensions. The dimension which is the greatest is the dimension on which the general axis runs parallel to. Note the general axis may not be a straight line, and may be curved or follow a tortuous path, so long as the axis is generally thought of as running parallel to the embodiment. Parallel may also include superimposed in the same line, whether straight or curved.

Described herein is a curved intramedullary fixation device with adaptable or alterable shape capable of deployment within a bone or boney structure while having a flexible or non-rigid form, then adapting to an inflexible or rigid form after deployment. The curved intramedullary fixation device with adaptable or alterable shape may revert to a flexible or non-rigid form subsequent to deployment for either further adjustment or removal from the bone or boney structure. Other embodiments are sufficiently flexible to be inserted along a curved path and sufficiently rigid after implantation without requiring a conversion step. Hereinafter, any discussion of bone placement shall also refer to boney structures, bone like structures or other support organs of an animal. The curved intramedullary fixation device with adaptable or alterable shape shall also simply be referred to herein as the device, support device or the apparatus.

In various embodiments, the device has a proximal end, a shape locking interface or section, a distal end, and an intermediate section. The device may be formed from a group of segments arranged in an end to end fashion, where each segment has a generally standardized shape. In various embodiments, the device may be flexible in two planes orthogonal to the general axis. In some embodiments, the device may be flexible in more than two planes orthogonal to the general axis. In some embodiments the standardized shape of each segment may include a generally cylindrical body having a first end and a second end. The first end may have a protrusion extending from the cylindrical body, and that protrusion may be formed or shaped so as to engage an aperture or receptacle shaped generally to receive the protrusion in a generally male to female arrangement. The cylindrical body may have one male end and one female end at the first or second ends. Alternatively the cylindrical body may have two male ends or two female ends. When the cylindrical bodies are lined up to form the device, the arrangement can be made so male ends are adjacent to and engage into female ends. The mechanical engagement need not be tight fitting. In various embodiments it may be useful for the male and female ends to meet and have some degree of slop in the fitting. By slop we mean that when the male and female ends are mechanically engaged, the adjacent segments are able to move relative to each other without disengaging mechanically. In other words, the male and female connection maybe such that the adjacent segments do not separate from each other when moved relative to the other in at least one plane.

In various embodiments, the support device may have a series of cylindrical bodies arranged in an end to end fashion with a male to female mechanical arrangement. In some embodiments the generally cylindrical body segments may have holes or apertures running parallel to the general axis. The holes may form one or more lumens in the support device when the segments are generally lined up. In some embodiments, the cylindrical bodies form segments of the support device and may be shaped to provide atraumatic surfaces and edges to prevent or reduce incidental tissue damage within bone during a procedure to place the support device within the bone, reduce injury when removing the support device, and also reduce the risk of aggravating the injury the support device is intended to help heal.

In some embodiments the segments of the support device may have a short height compared to the width of the segment, and in some embodiments the segments may have long heights compared to the width of a segment. In still other embodiments the segment height may be equal to the width. In some embodiments the segments of the device may be substantially uniform (all being of the same basic design with no more than 15% variation in any angles, axial lines and dimensions between segments), or the segments may be a completely mixed variety where no segment is similar to any other segment.

In some embodiments, the segments may have several holes in them that are substantially parallel to the general axis of the device. The holes may be arranged with a first hole in the center of the segment, with one or more additional holes arranged around the center hole. The one or more additional holes may be arranged in a regular arrangement around the center hole, or the one or more additional holes may be arranged in an irregular pattern, such as having more holes on one side of the segment than the other. The one or more additional hole may form one or more lumens through the support device when the individual segments are lined up in the device.

In some embodiments the holes may be drilled through the segment after the segment is formed. Drilling may be achieved mechanically, or through electromagnetic machining techniques such as laser, electric discharge machining (EDM), chemical processing or other techniques. In some embodiments the holes may be formed into the segment when the segment is created (e.g. during an injection molding process, die cast process or the like).

In some embodiments the segments have additional components incorporated into their structures to facilitate with the movement or fixation of the device within the bone to be treated. In some embodiments, the segment may have a movable element within the segment, such as a co-axial inner core that may be moved relative to the segment outer ring. The inner core may be shaped such that as it rotates, it causes elastic or plastic deformation of the outer ring, which may in turn help cause the outer ring of the segment to expand in at least one dimension. Such expansion may assist in helping the device anchor itself within the bone. Reversal of the rotation of the inner core may relieve the elastic stress and return the outer ring to its original shape, or cause a second plastic deformation to cause the outer ring to change into a reduced profile, which may be useful for withdrawing the support device from the bone.

In some embodiments, the segments have one external form when the device is being deployed into the bone, and a second external form when the device transitions or converts to its rigid inflexible state. The movable element of the segment may be one or more spur(s) or spike(s) which help anchor the support device in the bone. The spurs or spikes may protrude from a segment upon activation. Activation may be through mechanical means or via electromagnetic means.

In various embodiments, one or more fibers may be threaded through the holes in the segments, so that fibers extend from one end of the support device to the other through the holes in the segments. In various embodiments the holes are lined up to form lumens through the support device, so as to not crimp, impede or otherwise damage the fibers. In various embodiments the fibers may be affixed to the most distal segment and protrude from the most proximal segment. In some embodiments the fibers may be releasably engaged to the distal segment, and may be released from the segments and withdrawn from the segments when desired. In some embodiments the fibers that protrude from the most proximal segment may be adjusted by tensioning the fibers, torquing the fibers, pulling the fibers, pushing the fibers or exerting no force at all on the fibers. In various embodiments any combination of the above may be used on any number of the fibers at any time, and different forces (including no force) may be applied at any particular moment in time. In various embodiments, the force(s) applied to the fibers can be used to draw the segments closer together, push them apart, torque them in different directions, or hold the segments in a desired shape. In various embodiments the device shape is defined by a guidewire. In various embodiments, the fibers may be manipulated to fix the segments into a rigid or inflexible curved shape. In some embodiments, the fibers may subsequently be altered to return the support device into a flexible or non-rigid shape. In various embodiments, the support device may be advanced distally or retracted proximally while the support device is either flexible or rigid. In some embodiments, the fibers may be cables, wires, rods or similar structures. The fibers may be made of biocompatible metal (for example, stainless steel, titanium or nitinol), alloys, polymers, biosorbable materials, ceramics, glass, carbon fiber or any combination of these materials. Additional materials are provided and/or described herein.

In some embodiments, the shape of the device is provided by the guidewire or guide pin used to make the initial entry into the intramedullary space of the bone to be treated. The guidewire used may be one having a particular geometry to facilitate creating the desired shaped path in a curved intramedullary space. The device may be inserted over the guide wire or guide pin and traverse the length of the guide wire. While the device traverses the length of the guide wire, it follows the curvature of the guide wire and maintains that curvature during and after deployment. The fibers may be used to draw the individual segments together and may or may not contribute to the shape setting of the device when it is made rigid. Reference is made throughout the present disclosure of a guide wire being used to make the initial entry into the intramedullary space, and the device tracking over the guide wire. The guide wire may be a flexible or stiff wire, a guide pin or other device having similarly useful characteristics to make the initial entry into a bone, and able to bear the device tracking over it. It is not essential that the guide wire be so robust that the device cannot alter the shape of the guide wire if desired.

In some embodiments, the proximal section of the support device may contain one or more segments. The segments of the proximal section may have any of the features described herein and attributed to any segment, or may possess any of the following additional features. In various embodiments, the proximal section may serve as the proximal bone interface to anchor the proximal end of the support device to the exterior bone surface. In some embodiments this may be an individual or singular component. In some embodiments the anchoring may be done by a set of components that together form an exterior surface that contacts the cortical bone at the proximal end of the device. In some embodiments, the proximal section may have an interior surface that mates with the support device. The mating of the proximal section and the bone may provide for transferring load from the bone to the device. The load path begins in the bone, passes into the proximal end of the device, through the device, and along to the distal end, and back into the bone (this assumes a fracture with heavily fragmented bone that cannot be compressed at the fracture site). Alternatively, if the bone can be compressed at the fracture, the load path is shared, passing through the bone in compression, and through the device in tension. In some embodiments the proximal section may have a bone interface like internal threads. The internal threads may fit over some external threads of a shape locking device, or of the intermediate section, or of the rest of the support device.

In some embodiments the proximal end can transfer torque exerted on the proximal end to the body of the support device. In some embodiments the torque transferred from the proximal end to the distal end can be used to drive the support device through a bone channel, or other prepared path through the bone. In some embodiments where the body of the device is made of multiple segments, torque transmitted to the proximal section may also cause all subsequent segments and sections to rotate and experience at least some of the torque imparted to the proximal end or section. In some embodiments, the proximal end has a positive or negative relief feature for receiving a torque transmission device. The torque transmission device may be any instrument capable of transferring or applying torque, from human fingers to a screw driver to an electric powered drill.

In various embodiments, the proximal section may be shaped to facilitate engagement to the bone. In some embodiments the proximal end may have a cone shape, where the base of the cone (the wide part) is at the most proximal end, and the narrow part of the cone is connected to the main body of the support device. In some embodiments the proximal end may be shaped in an oblong manner so as to be partially tapered at both the distal facing side and the proximal facing side of the proximal end. Such double tapering may ease the insertion of the proximal end to the bone, and facilitate the covering of the support device once implanted into the bone.

In various embodiments, there is a shape locking section to convert the flexible configuration of the support device into a rigid or inflexible configuration. In some embodiments, the shape locking interface may have an outer shell, an inner expanding member, fibers and a locking screw. The outer shell may serve as one jaw of a clamping mechanism for the fibers which may be threaded through the interface. The outer shell may also serve as a retaining member for the proximal section via an external thread. In some embodiments, the inner expanding member is passed against the fibers feeding through the interface by the advancement of the locking screw. In some embodiments the locking screw may be tapered along its axis such that when advanced, it causes the inner expanding member to expand, and causing an interference fit between the outer shell, fibers and the inner expanding member. The resulting interference fit between the various components causes the fibers to be locked into whatever tensioned position they were in when the force was applied. As previously noted, the fibers may be tensioned to various degrees to cause the segments of the support device to change its curvature or shape.

In some embodiments, the support device may have more than one shape locking member. Additional shape locking members may be positioned at various lengths along the support device and be locked down independently. In some embodiments, locking down one shape locking member into one shape, and a second or third shape locking member down into a different shape, allows the support device to become rigid in a variety of shapes (e.g. a "S" shape, with two oppositely shaped curves).

In some embodiments, the shape locking mechanism may be an outer tension band and an inner support core. In other embodiments the locking interface may be one or more swage balls on each fiber where the fibers are held in place by an accessory tool. In some embodiments the locking mechanism may use gear teeth on the fibers and on the inside of the support device. In still other embodiments the locking mechanism may use a locking cap for fixing the tension of the various fibers.

In some embodiments the distal section may have one or more bone interface elements used to mechanically engage the bone. The distal end may anchor the distal end of the support device into a fixed position in the bone and prevent the distal end from moving. The distal end may be a single component having multiple segments, it may be a single component having a single segment, or it may be one or more components not the same as one of the segments. In some embodiments the distal end has a radial diameter greater than the main body of the support device. In some embodiments the distal end has a diameter the same as the main body of the support device, and in still other embodiments the distal end has a diameter smaller than the main body of the support device.

In some embodiments, the bone engaging feature of the distal end may be a screw thread. In some embodiments the screw thread may have cutting edges for cutting both when the distal end is rotated either clockwise (e.g. insertion), or counter clockwise (e.g. removal). In some embodiments the bone engaging feature may be a frangible screw. In some embodiments the bone engagement feature may be any one or more of spikes, pins, clips, grommets, claws, bumps, wires, washers or similar features that are able to provide mechanical engagement between the distal end of the support device, and the bone.

In some embodiments the segmented support device may have a polymer sleeve to help provide an atraumatic surface between the curved intramedullary fixation device and the bone.

In various embodiments, the device may be a tubular body. The tubular body may have a proximal end, a distal end, and a section in between the proximal and distal section. The tubular body may be flexible about two axes orthogonal to the general axis. In some embodiments, the tubular body may be flexible about more than two axes orthogonal to the general axis. Flexibility about two orthogonal axes orthogonal to the general axis allows the device to follow a complex shape, for example a complex shape formed by a guide wire which was previously inserted into curved bone(s). In some embodiments, the tubular body may have apertures, cuts or material removed from the main body. These apertures, cuts or removed material may be arranged and shaped in such a manner as to promote flexibility in the tubular body. The device could be one piece. For example a machined titanium or polyether ether ketone (PEEK) screw with reliefs in the body of the device to make the body flexible. In other embodiments a proximal, body, and distal section could be mechanically attached to each other.

In some embodiments, a guidewire is placed under fluoroscopic guidance and the curved intramedullary fixation device is inserted over the guidewire. Insertion of the device may be then be accomplished by screwing the device into bone. In other embodiments, the device may be properly positioned within the bone without using a guidewire.

In the various embodiments described herein, the curved intramedullary fixation device may be composed from a polymer, a metal, an alloy, or a combination thereof, which may be biocompatible. For example, the fracture stabilization device can be formed from titanium or a titanium alloy. Other suitable metals may include stainless steel, cobalt-chromium alloys, and tantalum. In some embodiments, metal alloys having shape memory capability, such as nickel titanium or spring stainless steel alloys, may also be used. In some embodiments, the fracture stabilization device can be formed from a suitable polymer including non-degradable polymers, such as polyetheretherketone (PEEK) and polyethylene (PE), as well as modified versions of these materials (for example, PEEK+calcium phosphates and PE+vitamin E, metal coatings, or surface texturing). Additional non limiting polymers may include; polyether-block copolyamide polymers, copolyester elastomers, thermoset polymers, polyolefins (e.g., polypropylene or polyethylene, including high density polyethylene (HDPEs), low-density polyethylene (LDPEs), and ultrahigh molecular weight polyethylene (UHMWPE)), polytetrafluoroethylene, ethylene vinyl acetate, polyamides, polyimides, polyurethanes, polyvinyl chloride (PVC), fluoropolymers (e.g., fluorinated ethylene propylene, perfluoroalkoxy (PEA) polymer, polyvinylidenefluoride, etc.), polyetheretherketones (PEEKs), PEEK-carbon fiber composites, Polyetherketoneketones (PEKKs), poly(methylmethacrylate) (PMMA), polysulfone (PSU), epoxy resins and silicones. Additionally starch based polymers may be used.

Additional materials may include carbon and polyaramid structures, glass or fiberglass derivatives, ceramic materials, and artificial biocompatible protein derivatives (recombinant derived collagen). In other embodiments, the fracture stabilization device may be made of a metal and/or alloy segments with a polymer shell, or a sandwich style and coaxial extrusion composition of any number of layers of any of the materials listed herein. Various layers may be bonded to each other to provide for single layer composition of metal(s), alloys, and/or polymers. In another embodiment, a polymer core may be used with a metal and/or metal alloy shell, such as a wire or ribbon braid.

Additionally, at least a portion of the fracture stabilization device may include a bone integration surface to promote bone ingrowth, on-growth, and/or through-growth between the segments, if desired. The bone integration surfaces can comprise a three-dimensional space to allow bone integration into and/or onto portions of the fracture stabilization device. The three dimensional space can be provided by a three-dimensional substrate, for example beads, and/or by the provision of holes through the bone integration portions. Other methods for achieving bone integration can include the provision of an appropriate surface topography, for example a roughened or textured area and/or by the provision of osteoconductive coatings, such as calcium phosphates. The bone integration surface may enable the fracture stabilization device to provide a metal and/or polymeric scaffold for tissue integration to be achieved through the fracture stabilization device. In various embodiments, various materials may be used to facilitate, stimulate or activate bone growth. A non-limiting list of materials may include hydroxyapatite (HA) coatings, synthetic bioabsorbable polymers such as poly (α-hydroxy esters), poly (L-lactic acid) (PLLA), poly(glycolic acid) (PGA) or their copolymers, poly(DL-lactic-co-glycolic acid) (PLGA), and poly(ε-caprolactone) (PLC), poly(L-lactide) (LPLA), (DLPLA), poly(ε-caprolactone) (PCL), poly(dioxanone) (PDO), poly (glycolide-co-trimethylene carbonate) (PGA-TMC), poly (lactide-co-glycolide), polyorthoesters, poly (anhydrides), polyhydroxybutyrate, poly(l-lactide-co-glycolide) (PGA-LPLA), cyanoacrylates, poly(dl-lactide-co-glycolide) (PGA-DLPLA), poly(ethylene carbonate), poly(iminocarbonates), poly(l-lactide-co-dl-lactide) (LPLA-DLPLA), and poly(glycolide-co-trimethylene carbonate-co-dioxanone) (PDO-PGA-TMC).

Furthermore, at least a portion of the fracture stabilization device may be treated or coated with a calcium material, such as calcium deposits, calcium phosphate coatings, calcium sulfates, modified calcium salts such as Magnesium, Strontium and/or Silicon substituted calcium phosphates, RGD sequences, collagen, and combinations thereof in order to enhance a strength of bone ingrowth, on-growth, and/or through-growth between the segments or other portions of the fracture stabilization device.

The process of repairing or providing support to a bone to prevent further degradation of the bone's structural integrity may involve diagnosis and understanding of the underlying cause for the bone injury, disease or weakness. Any diagnostic tool or procedure is not part of the present disclosure and does not form any aspect of the methods of using the system, apparatus and methods described herein.

Once the nature of the injury to be treated is understood and a treatment plan involving the herein described support device is conceived, the doctor or operator may proceed to access the bone where the support device is to be placed. In some embodiments the support device is entered into the bone where there is a minimum of other bone joints, nerve tissue and/or muscle mass so the use of the support device has the lowest probability of creating additional injury or increasing the patient's recuperation time. Because there is a general desire to promote quick healing, the procedure involved in using the herein described support device may be one that is minimally invasive. In some embodiments the procedure may be fully invasive. In some procedures the support device may have an increased length to allow the support device to enter bone far from the injury site, and still successfully navigate the bone and injury site. In some embodiments, extra length of the support device may be relegated to the proximal end, where a greater flexibility of segment choices are generally permitted. In some embodiments, the area of injury may be close to the access point to the bone, and to ensure proper fixation of the support device, the distal segment may have increased length to engage in cortical bone or other healthy tissue sufficient to provide for bone fixation. Where the distal section is elongated, regardless of the reason why the distal section is elongated, the choice of different segment types may also be generally flexible.

In some embodiments, the support device as described herein may be used in a procedure to promote fixation of a bone. In some embodiments, a method of fixing a fractured or broken bone may utilize any one or more of the steps such as creating a surgical incision in a patient to gain access to a bone surface, creating a hole in the bone, inserting a guide wire into the bone, navigating the guidewire along a curved path within the bone, feeding a flexible reamer over the guide wire, creating a channel for the support device, removing the reamer, advancing the support device into the bone, adjusting the shape of the support device, fixing the shape of the support device, and securing the support device in the bone.

In some embodiments there may be one or more additional steps such as observing the movement of the guide wire, reamer or device into the bone, threading one or more sections of the support device into the bone, securing the shape of the support device through one or more locking mechanisms, rotating the support device, applying torque to the support device, applying torque to a section or segment of the support device.

In some instances, it becomes necessary to remove a bone fixation device from a patient. The support device of the present disclosure may be removed following a series of steps similar to, but not necessarily opposite of the implanting steps. In some embodiments, the support device may be removed from the bone by: exposing the shape locking feature, returning the flexibility of the support feature, and removing the support feature from the bone.

In various embodiments, removal of the support device may entail one or more additional steps, such as exposing the proximal end for manipulation, disengaging the proximal end from the shape locking feature, removing the shape locking feature (or element), withdrawing the support device, retracting any retractable bone engagement features, rotating the support device, applying proximally directed force on the support device or any of its sections and/or segments. Other embodiments may not use or require a shape locking element to be unlocked prior to removal.

Figure 1B:
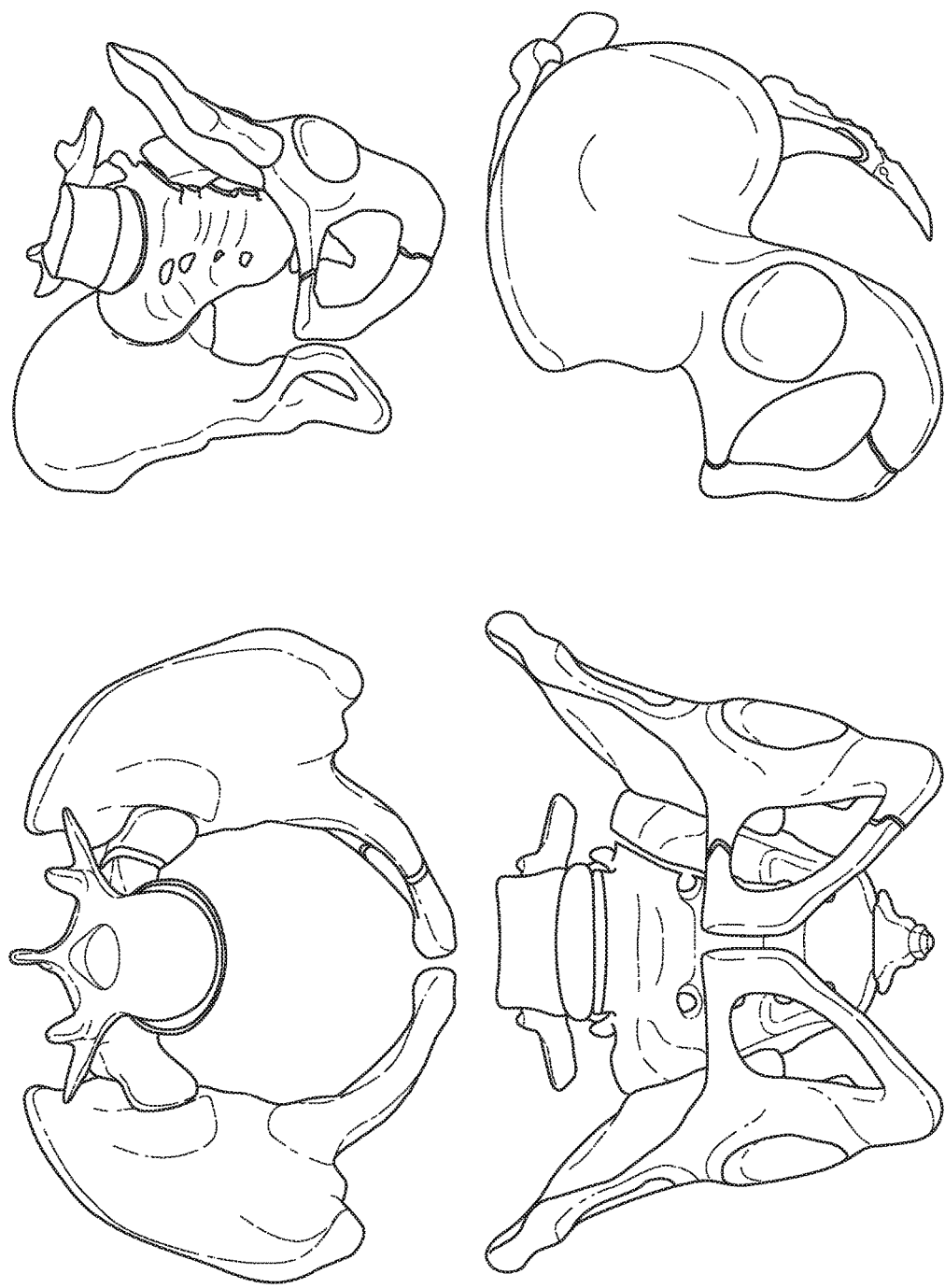
Figure 2:
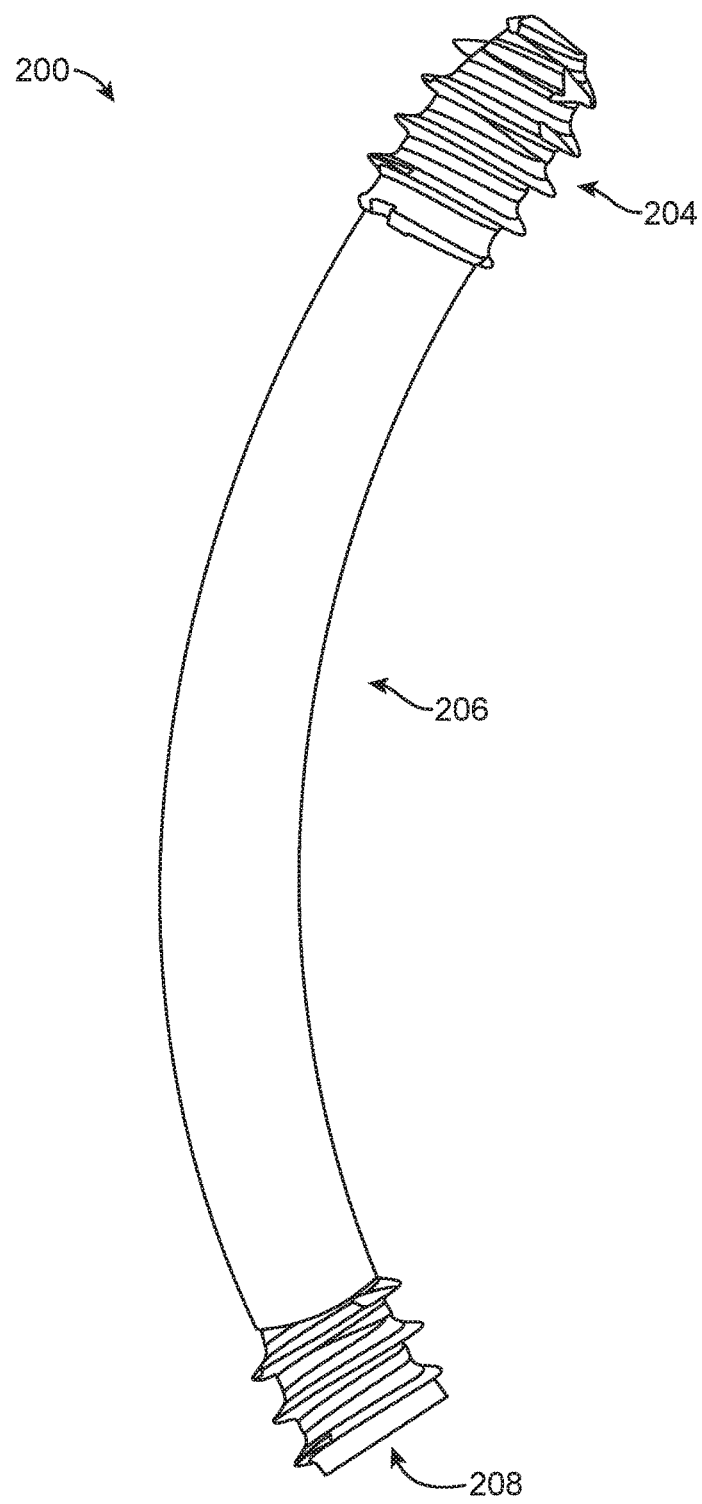
FIG. 2 depicts an embodiment of a curved intramedullary fixation device according to an embodiment.

Discussion of the various embodiments, alternative arrangements and methods of use are now further described in some forms by turning now to the drawings. A notation used in the drawings may refer to various parts with a subscript, in particular part number $X_{a-n}$, where X is the general part number, and a-n refers to a sequence of parts, or numerous parts having many numbers. The use of a-n simply refers to the parts starting with "a" and ending at some undetermined number "n." The use here is similar to the general use in mathematics when referring to a number of variables from A to N. As a representative curved bone structure, the pelvic ring 100 has several areas where short curved bone sections are present (FIG. 1). Some elements of the pelvis are the Ilium 102, the Pectineal Line 110, the Os Pubis 108, the Ischium 106 and the Pubic Arch 104. The pelvic ring is a key structural element of the skeletal system because it is a weight-bearing structure interposed between the upper body and the legs. As such, if a fracture occurs and it is untreated, the pelvic ring may not heal (nonunion) or may heal in a poor position (malunion). Nonunion can lead to chronic pain and an inability to walk. Malunion can result in a short leg or one which points in the wrong direction or an abnormal gait. There are variations between the male and female pelvis and pelvic ring, and the male structure is shown in FIG. 1. However the arbitrary selection of using the male pelvis is not to be taken as limiting or discriminating in any sense. The use of the technology described herein is designed and adaptable for use in both the male and female anatomy. Certain adjustments may be necessary to accommodate one or the other anatomy, and such adjustments will be evident to those skilled in the field of bone fixation upon detailed study of the present disclosure.

A treatment of these kinds of fractures in curved bones may be utilize a curved intramedullary fixation device (device) capable of implantation into a variety of curved pathways inside the bone. These curved pathways inside the bone may vary about two or more axes long the length of the device. Such a support device 200 may have a distal end 204, a main body 206 and a proximal section 208. In some embodiments the support structure 200 in the many embodiments is the main body 206 can be flexible when delivered, and then made rigid or inflexible when the support device 200 is properly positioned. The transition between a flexible state and a rigid state may be achieved through various means, such as a shape locking mechanism. In other embodiments the main body 206 is sufficiently flexible to be implanted along a curved intramedullary path yet sufficiently strong enough to withstand tensile and vertical shear forces required to fixate the fracture(s). In other words, no transition step between flexible and rigid states is required. The distal end 204 and the proximal end 208 may have one or more features to assist in engaging the bone.

Figure 3A:
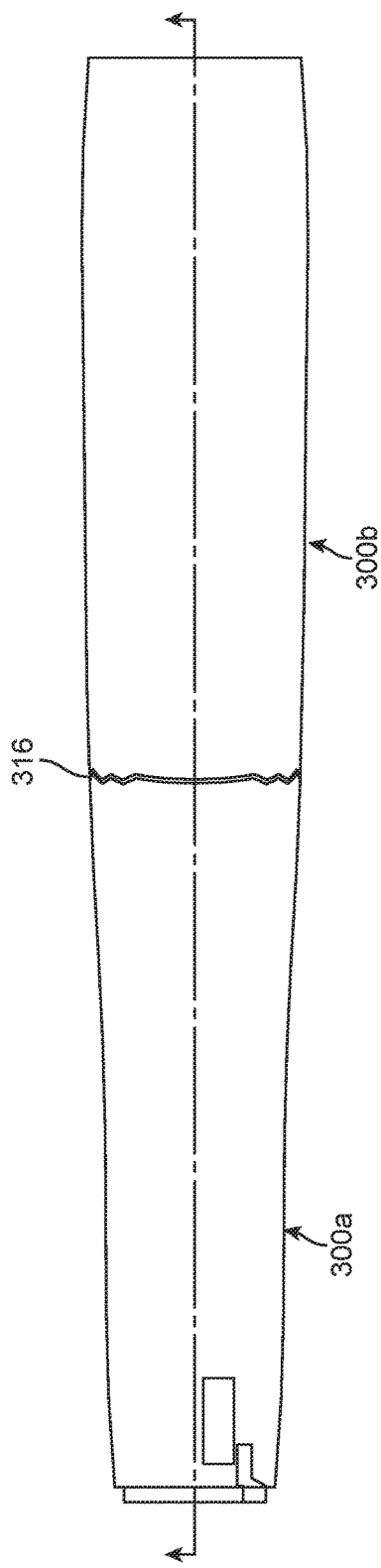
FIG. 3A show a bone with a fracture.
Figure 3B:
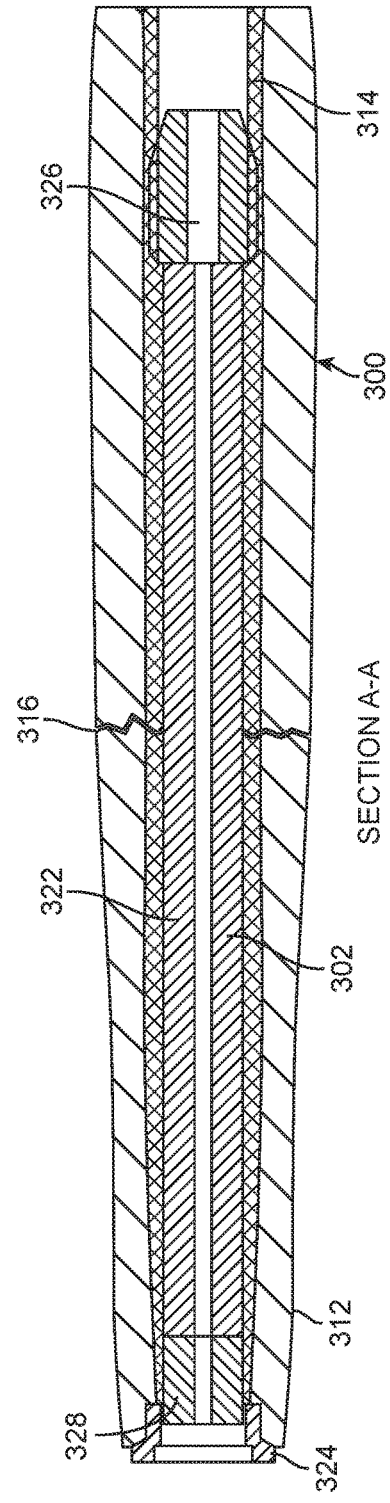
FIG. 3B illustrates the device inside a broken bone.

A cross-sectional view of a fractured bone 300 with a support device 302 is now described (FIGS. 3A-B). The depicted bone of FIG. 3A is straight for ease of illustration only, all features of the support device 302 are equally applicable to a curved bone. As represented in FIGS. 3A and 3B, a bone 300 may include an outer cortical bone layer 312 that surrounds the cancellous bone 314. A fracture 316 may extend partially or completely through the bone 300, forming two separated bone portions 300a and 300b. A fixation device 302 may generally include a main body 322, with a proximal bone interface 324, and a distal bone interface 326. The fixation device 302 may also include a shape locking interface, generally represented at 328.

Various embodiments of fixation devices 302, including various embodiments of the main body 322, various embodiments of the proximal bone interface 324, various embodiments of the distal bone interface 326, and various embodiments of the shape locking interface 328 are discussed below. The four components are configured to be modular to a degree, such that the alternate embodiments described for each component may be interchangeable with one another, and may also be usable with any of the embodiments of the other three components. All sections may be manufactured using standard machining, electric discharge machining (EDM), metal injection molding MIM, traditional molding, polymer injection molding, metal casting, and/or forging methods, or any combination. The various elements of the device may be produced from Titanium Grade 23 6Al-4V ELI material. Other implantable materials may also be feasible for use, including but not limited to 316 LVM Stainless steel, polyether ether ketone (PEEK), other any material considered biocompatible, materials, and/or a combination of the materials previously described.

The use of the term "fiber" may refer to any variety of elongated strands of material, such as filaments or wire, having any of various cross sections including, but not limited to, round, rectangular, square, and bundles (for example cable) of any of the former. The terms "fixing" or "to fix" refer to holding or setting something in place. In particular, a bone fracture may be fixed by causing a device placed across the point of fracture to become rigid, thereby stabilizing the bone on either side of the fracture. Additionally, the device itself may transition between a rigid state and a flexible state by actuating a transitioning member. The device may be highly flexible to navigate a complex series of S curves, or semi-rigid and rather stiff to handle a simple curve. Regardless of the level of flexibility in the device, the various segments can be locked down to enhance the rigidness of the device.

The main body 322 may have at least one flexible portion that is configured to bend, rotate along, or follow a curved path. In an embodiment, at least a portion near the distal end 326 may be flexible, or alternatively, the entire body 322 may be flexible. For fixation of bone, as represented in FIG. 3B, a fixation device 302 may be implanted to extend lengthwise across the fracture 316 to stabilize the bone segments on each side of the fracture with respect to one another. To access the bone 300, a small surgical incision may be made through the skin and soft tissue, and access to a bone surface may be provided by a system of trocars and cannulae placed through the soft tissue. A hole may be made in the hard outer cortical bone layer 312 using a drill to access the interior (cancellous) bone 314. A, bent tip guidewire may be placed though the cannula into the interior of the bone, and the guide wire may be driven into the interior cavity of the bone under fluoroscopic observation. The sharp tip of the guide wire may be oriented toward the interior of the bone curvature, such that the tip does not dig into the exterior cortical wall. The guide wire will generally follow, and may be directionally guided through the interior geometry of the bone to a desired depth past the fracture 316. If desired, the sharp tip guide wire may be exchanged for a blunt tipped guide wire. A flexible reamer, having a diameter appropriate for an intended support device 302 may be fed over the guide wire to create a tunnel, or cannula, along the same path as the guide wire. The reamer may be withdrawn, leaving a curved tunnel or passage way for the support device 302. Other embodiments do not require reaming prior to implanting the device over the guide wire. These embodiments may include self-drilling and/or self-tapping threads on the distal end of the device. For embodiments wherein the fixation devices include apertures, the guide wire may be left in place to guide the support device 302 into place.

In embodiments, the main body 322 may be configured as a one-piece body, or, alternatively, may be configured as a plurality of interconnected segments, or segments. The length of the support device 302 may vary depending on intended use, such as severity and location of the fracture, and stress that may be applied to the fractured bone. In embodiments, the length may be about 80 mm, about 100 mm, about 120 mm, about 140 mm, about 160 mm, about 180 mm, about 200 mm, about 220 mm, about 240 mm, about 260 mm, about 280 mm, about 300 mm, about 400 mm, about 500 mm, about 600 mm, or any length between any of the listed lengths, or if needed, longer or shorter than the listed lengths. The diameter of the support device 302 may also vary depending on intended use, such as severity and location of the fracture, and stress that may be applied to the fractured bone. As a reference point, the diameter may be defined by the outer diameter of features on the device distal end 326. In embodiments, the diameter may be about 5 mm, about 6 mm, about 7 mm, about 8 mm, about 9 mm, about 10 mm, about 11 mm, about 12 mm, about 13 mm, about 14 mm, about 15 mm, or any diameter between any of the listed diameters, or if needed, larger or smaller than the listed diameters. The diameter of the device may be maximized for a particular procedure to optimally full the intramedullary space between outer cortical bone layers displacing weak cancellous bone and optimizing the strength of the bone fixation relative to, for example, a straight intramedullary screw. The device may be scaled up or down for treating larger or smaller animals than human beings. The bend radius of the support device 302 may also vary depending on intended use, such location, and the curvature of the fractured bone in the vicinity of the fracture. In embodiments, the bend radius may be about 40 mm, about 45 mm, about 50 mm, about 55 mm, about 60 mm, about 65 mm, about 70 mm, about 75 mm, about 80 mm, about 85 mm, about 90 mm, about 95 mm, about 100 mm, or any radius between any of the listed values, or if needed, larger or smaller than the listed lengths. As a non-limiting example, a support device 302 may have a length of about 150 mm, a diameter of about 10 mm, and a bend radius of about 60 mm.

In another embodiment, a filler 400 may have a length that fits within the interior of a cannula of a fixing device (FIGS. 4A-4B, FIGS. 29A-29B). The filler 400 may be cannulated and include a longitudinal cannula 402 to fit over a guide wire. An exterior of the filler 400 may include a number of grooves 404 separated by dividers 406. The grooves 404 may have a cross-sectional configuration that matches the cross-sectional configuration of the fibers. The grooves 404 have a semi-cylindrical base for receipt of cylindrical fibers 408 therein.

In an embodiment, fibers 408 may be inserted into a fixation device to a length as needed, and the filler 400 may be guided to the entry. The fibers 408 may be aligned with corresponding slots 404 on the filler 400, and the filler may be inserted into the body of the device. Upon insertion of the filler 400 into the device, the fibers 408 will align into the slots 404 and engage the teeth on the interior surface. In an embodiment, the filler 400 may also include an end plug 410 that limits movement axially into the fixation device, and provides a gripping area for gripping the filler during installation, and allows for gripping the filler for removal, if removal is or becomes necessary. Upon removal of the filler 400, any engaged fibers 404 may then disengage from the interior and also then be removable as well.

Figure 4A:
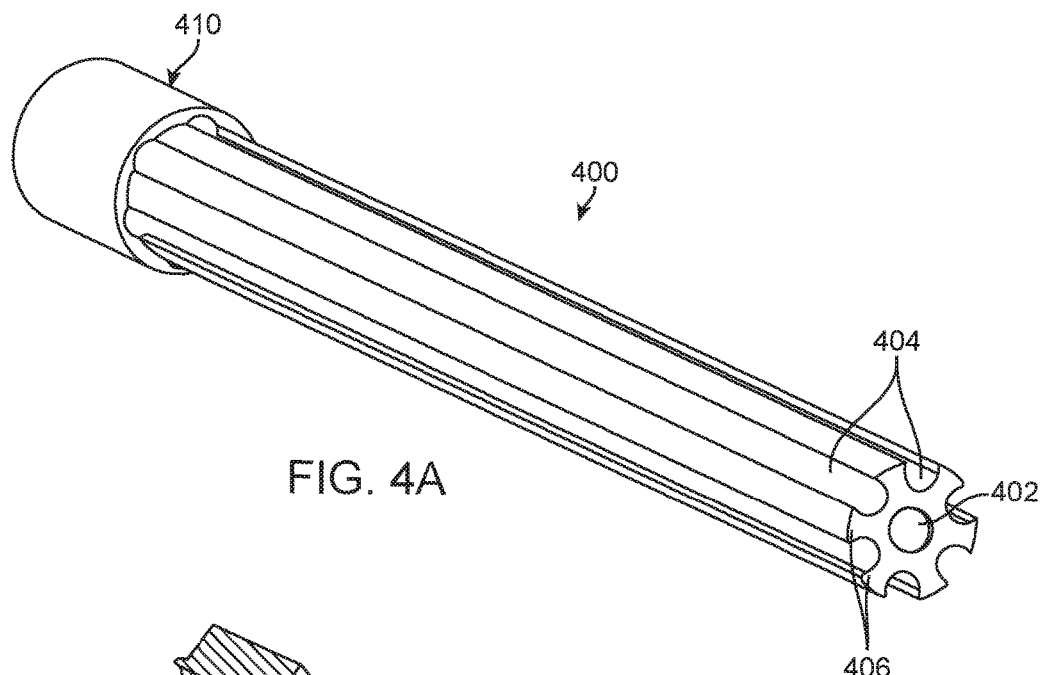
FIGS. 4A-4D provide various embodiments of a core for the device.
Figure 4B:
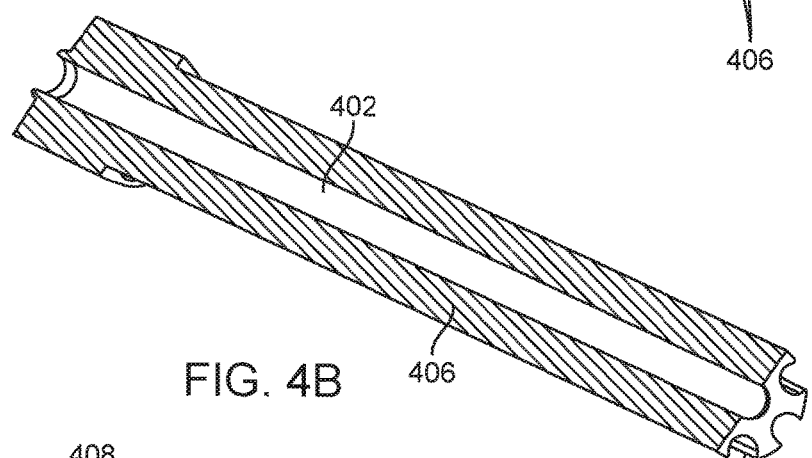
Figure 4C:
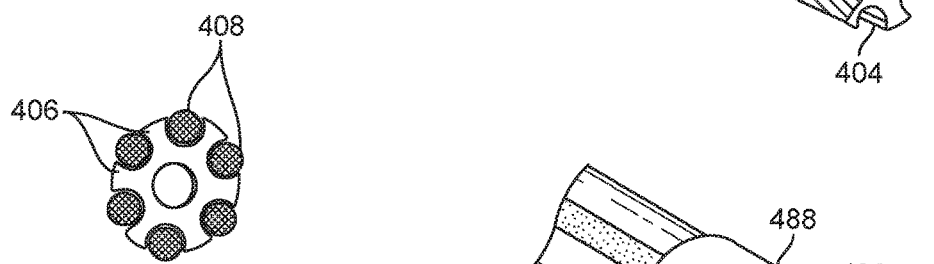
Figure 4D:
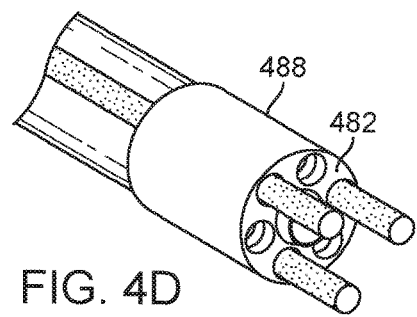

In an embodiment of a fixation device, the body may have a smooth internal surface instead of threads, and a flexible filler 400 and fibers 408 may be longitudinally disposed within the body, with the filler configured to separate and support the fibers within the longitudinal grooves 404. The body may be shape-locked by tensioning the fibers 408 within the body. A first end of fibers 404 may be attached to the distal bone interface or the end 82a of the filler 400. The second end of the fibers 408 may extend through the plug 488 and beyond the end 482 as represented in FIG. 4D. In its flexible state, the fibers 408 and filler 400 may be movable axially with respect to one another to thereby allow the support device to bend during insertion along a curved path. Once the support device is in place within the bone the fibers 408 may be tensioned and fixed in place (in a manner as discussed further below) with respect to the end 82b thereby minimizing, or prohibiting further relative axial movement between the fibers and the filler 400, and effectively shape-locking the configuration within the bone.

In additional embodiments of the support device, the body may include a plurality of individual interconnecting segments, or segments. In an embodiment as represented in FIGS. 5A-5E, at least a portion of a fixation device 500 may include a body portion 502 that is formed from a plurality of segments 504. In an embodiment, the segments 504 may be cylindrical discs, columns or other generally stackable elements, collectively referred to as segments. In alternative embodiments, the segments may have other cross-sectional configurations, such as triangular, rectangular, hexagonal, octagonal, or various other shapes. Each segment 504 may include a hollow core 508, allowing for passage of a guide wire 510, which may be used to direct the device into/through a bored hole as discussed above. The segments 504 may have various heights 504h and diameters 504d, wherein the diameters may be selected from the diameters as previously described. Further embodiments of segments of various ratios of height to diameter are presented further below.

Each segment 504, may include a first face 520 and a second face 518, disposed opposite the first face, and the segments may stack in a series, as shown in cross-section in FIG. 5B, with first faces of one segment adjoining second faces of an adjacent segment. At least one of the first face 520 and the second face 518 may include a centering pivot 522, that engages within a corresponding recess 516 of the other of the first face and the second face of a sequential segment in the series. In an embodiment as shown, one face may include the pivot 522 and the other face the recess 516. In alternative embodiments (not shown), for alternating segments, each face of one segment may include the pivot 522, and each face of an adjoining segment may include the recess 516.

To limit segment to segment angulation, or pivot of one segment on another segment, to a pre-determined maximum value, at least one of the first or second face surfaces 520 and 518 may be disposed with an angular inclination 518α, while the other surface may be essentially flat. In an embodiment, as shown in FIG. 5C, surface 520 may be higher towards the pivot 522 than at the periphery, and the surface 518 may be essentially flat. In an alternative embodiment (not shown), the surface with the recess 516 (surface 518 in FIG. 5C) may be the angled surface, and the surfaces having the pivot 522 may be flat.

The angular inclination 504α may therefore provide one limit for defining a minimum bend radius of the body 502. For example, stacked segments 504 with larger inclination angles 504α may bend to a tighter radius of curvature than segments having a smaller angle 504α. In embodiments, for example, the angle 504α may be about 2°, about 3°, about 4°, about 5°, about 6°, about 7°, about 8° about 9°, about 10°, about 11°, about 12°, about 13°, about 14°, about 15°, about 18° or any angle between the listed values or greater than the listed values.

A height 504h of the segments may also provide a limit for defining a minimum bend radius of the body 502. For example, stacked segments 504 with smaller heights 504h may bend to a tighter radius of curvature than segments having larger heights 504h. In embodiments, for example, the height 504h may be about 3 mm, about 4 mm, about 5 mm, about 6 mm, about 7 mm, about 8 mm, about 9 mm, about 10 mm, about 11 mm, about 12 mm, about 13 mm, about 14 mm, about 15 mm or any value between any of the listed values.

In an embodiment as depicted in FIGS. 5A and 5B, the segments 504 may be stacked and then inserted within a flexible sheath 514. In embodiments, the sheath may have a wall thickness of about; 0.5 mm, about 1 mm, about 1.5 mm, about 2 mm, about 2.5 mm, about 3 mm, about 3.5 mm, about 4 mm, about 4.5 mm, about 5 mm, or any value between any of the listed values. Depending on the tension-locking method used, the interior of the sheath may be smooth, threaded or toothed and may have a smooth internal surface. In some embodiments the sheath may have similar features to an outer layer of a catheter, being generally smooth and low friction with great bendability. The outer sheath may be made entirely of a light weight polymer, and may be a mono-layer or multi-layer sheath. The sheath may be reinforced (such as with a wire or wire ribbon braid) to promote pushability, or rely on the support device for both axial and radial support to prevent collapse. In some embodiments the sheath may collapse and "shrink fit" on the support device, while in other embodiments the sheath may have a gap space between the body of the support device and the sheath. Such gap space may be used for the injection of fluids, medicines or antibacterial compounds.

To shape-lock the segments 504 in a desired configuration after insertion of the device 500 into a fracture location, the segments may include a plurality of bores 524 disposed substantially parallel to the central core 508 and spaced circumferentially about the central core. Bores 524 may be configured to separate and support a series of tensile fibers 512 (one of which is represented in FIG. 5B) that may extend longitudinally through the aligned bores of sequentially stacked segments. In the flexible state, the fibers 512 may be axially fixed to the distal bone interface 506 only, with the fibers free to translate through their respective bore holes in each segment. When a tension is applied to the fibers 512 and the tension is locked with respect to the segments 504, via the proximal bone interface in a manner as discussed further below, translation of the fibers becomes limited and the segments become shape-locked with one another to maintain an overall shape of the device 500.

Figure 6:
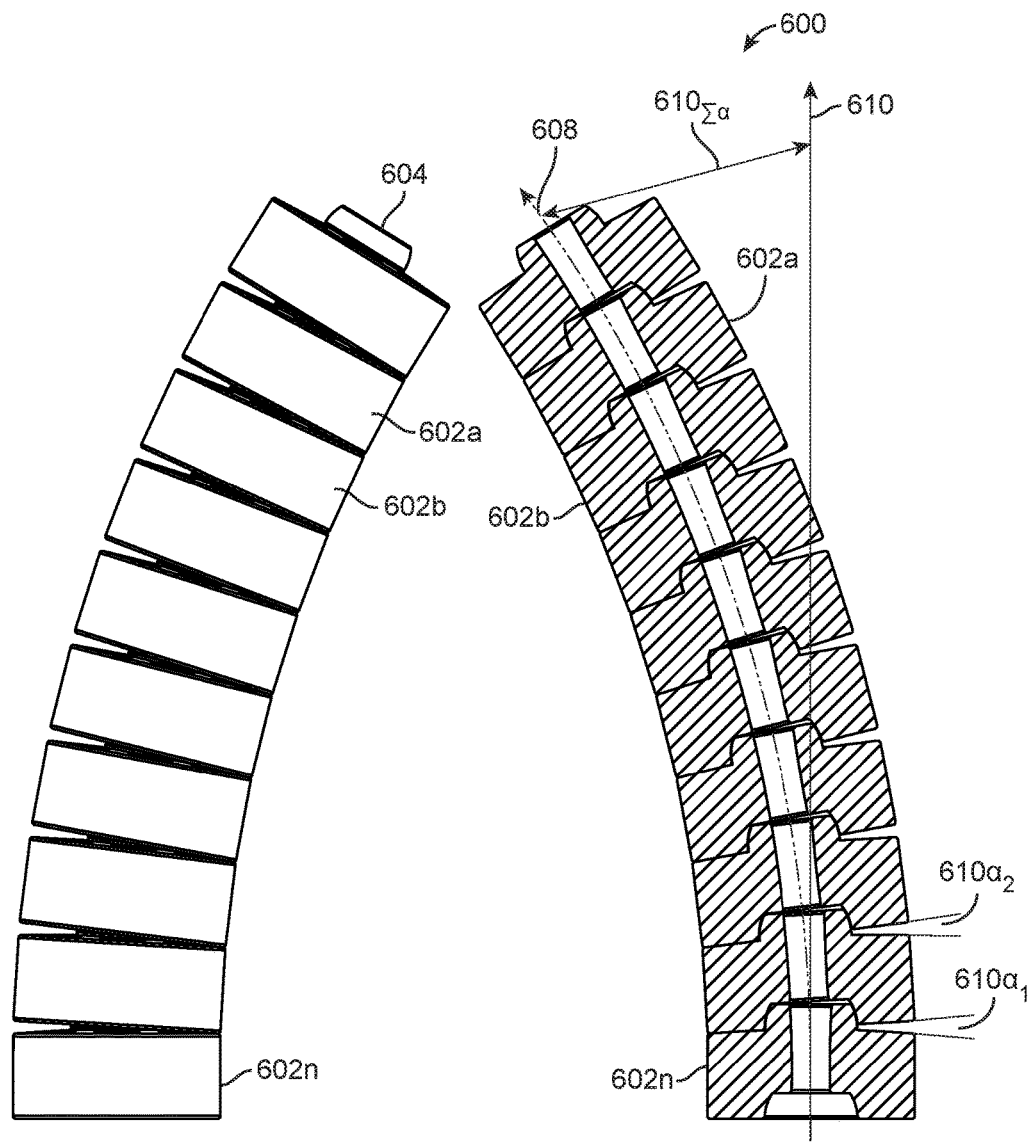
FIG. 6 illustrates a stack of device segments in two views.

In an embodiment, three or more fibers 512 may be included to provide segment fixation about all planes of movement. Each bore hole or channel 524 may not require a fiber 512, depending on the required strength and stability needed for the fixation device. Additional tensile fibers 512 may be added to provide additional strength, as well as a more uniform flexural stiffness in any bending axis with respect to the fibers pattern orientation. For segments 504 having six bore holes 524, three, four, five or six fibers may be provided within the segments, with at least one fiber in each of the positions disposed at about 120° from one another about the central bore 508 (see FIG. 6).

As discussed further below with regard to tensioning of the fibers 512, the fibers may terminate within the main body, or in members attached to either end of the main body, for example, the distal bone interface 506. The bore holes 524 in each segment 504 may form a lateral support for each fiber 512, keeping the fibers away from the neutral bending axis. When the assembly is made rigid, the assembly may experience a transverse load, the transverse load creates a purely tensile load in any fiber on the opposite side of the bending axis from the transverse load, a compressive load between bead segments, and a reduction in tension in the fibers on the adjacent side of the neutral axis.

Alternatively, with all fibers in the construct fixed in length, and each radially constrained but not under initial tension, loads applied to induce bending could result in a set of compressive fibers on one side of the neutral bending axis, and a set of tensile fibers on the opposing side of the neutral axis. In this construct, the load path supporting bending does not transmit a compressive load across segments.

In addition, the assembly of the fibers 512 inside the holes 524 of each segment 504 provides a torque transmission capability equal to the shear strength of the sum of at least two fibers, and at most the total number of fibers in the assembly. The torque transmission capability locks the torque between adjoining segments and thereby provides for a screw-in insertion of the fixation device, as the torque may be transmitted from the proximal end, through the segments 504 to the distal bone interface 506 via the fibers 512.

In the embodiment as depicted in FIGS. 5D and 5E, a segment 504 may include six bores holes 524 disposed at a spacing of about 60° so that the bore holes maintain tensile fibers 512 at a distance from the center of the segment, as well as in a specific radial positions of about 0°, 60°, 120°, 180°, 240°, 300°, and 360° relative to one another about the central core 508. Additional segment embodiments are discussed below.

In some embodiments, one or two bore holes 524 may be used to change the shape of the body 500. In some embodiments the body 500 may have a predisposed bend to it and a single fiber 512 may be used to offset the predisposed bend to relax or reduce the curvature of the body 500 during deployment and shape fixing. Alternatively two fibers 512 may be used at various radial positions about the center to perform a similar function. In still other embodiments, one or more fibers may be disposed outside the body and under the sheath, and the fiber may be tensioned and fixed into position to cause the desired shape setting (not shown).

In some embodiments, the individual segments 602a-n may be stacked one on top of another. The segments may have an angled surface on top or bottom allowing adjacent segments to lean off the main axis (FIGS. 6A-B). The angled surface of each segment allows each segment to have a small angle of deflection off the main axis from the adjacent segment (either above or below). The deflection can be determined based on the angle of the surface 602α. The sum of the angle deflections 610Σα off the main axis determines the curvature of the device 600. The deflection 602α of adjacent segments may be the same or it may be a higher or lower deflection. The stack of segments provides the section of the device where the greatest number of deflections off axis can occur. The sum of the deflections $610\Sigma\alpha$ from the normal axis 610 is represented by the curved axis 608. Here the segment stack is shown both in a plan view (FIG. 6A) and in a cross section view (FIG. 6B). In this view, the segment height is less than the segment diameter, however this is merely illustrative of one embodiment and in no way limiting. The segment may have a height equal or greater than the segment diameter.

Figure 7A:
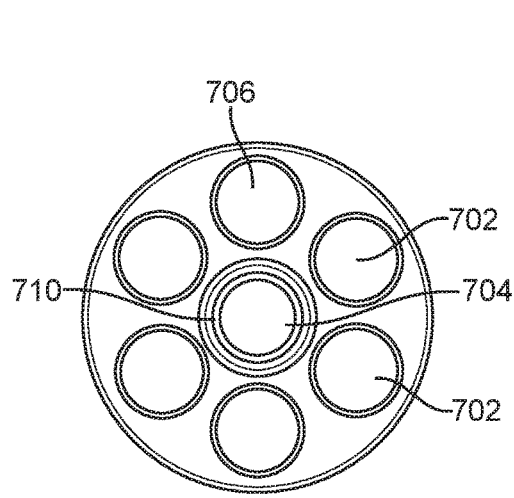
FIGS. 7A-7C provide an alternative embodiment of a segment.
Figure 7B:
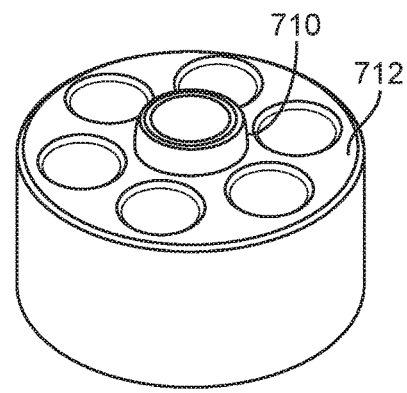
Figure 7C:
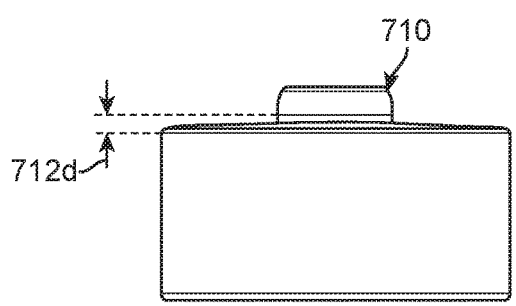
Figure 7D:
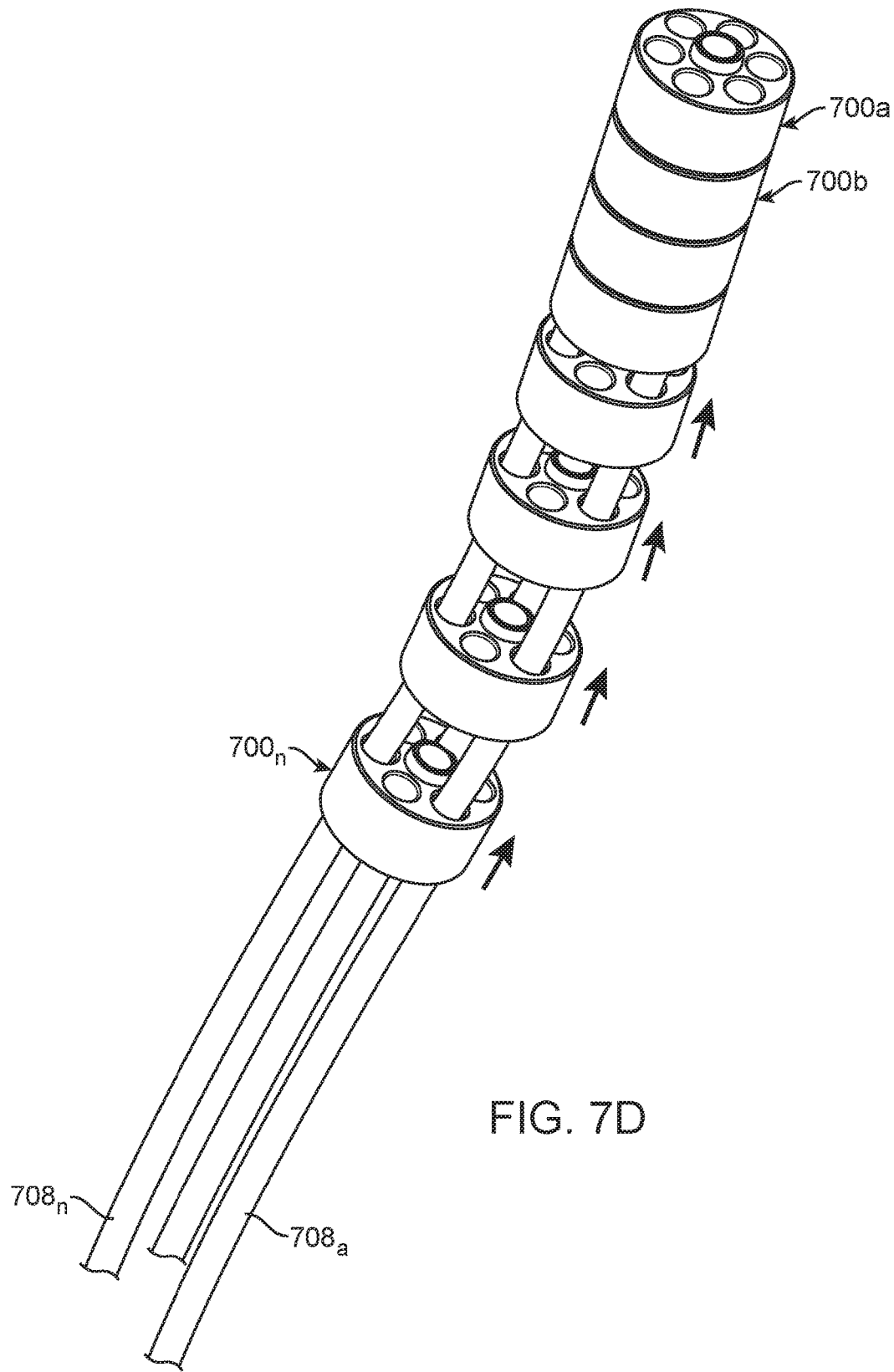
FIG. 7D provides an illustration of segments being threaded together.

In some embodiments, the individual segments 700 may have two or more bore holes or channels 702, 704 (FIG. 7A). A central bore hole or channel 704 may be used for sliding over a guide wire or guide pin. The peripheral channels 702 may be used for sliding over a fiber. By stacking the segments 700 on top of each other (FIG. 7D), the segments can be aligned using a form a generally contiguous body. The segments can align on the central collar or positive relief feature 710. The positive relief feature 710 may be raised above the angled plane 712d of the top surface 712 of segment 700. The difference in height between the edge of the segment 700 and the positive relief feature 710 forms an angle 712d. When the segments are stacked 700a-n over the fibers 708a-n, they form the body of the multi-segmented device. The segments can bend relative to each other. By way of analogy only, one might envision the body of a centipede or millipede. The arthropod body is not flexible between segments, but collectively with a higher number of segments, the arthropod body is able to curve on itself.

In some embodiments, the individual segments 800 may be tall, having a height dimension 800h which is greater than the diameter 800d (FIGS. 8A-D). The segment 800 may have a central bore hole or channel 802 and a raised neck or positive relief feature 804. Any number of peripheral channels 806 may be formed in the segment 800. These taller segments may have a standard form with a top surface having a positive relief feature 804 and a bottom surface having a negative relief feature 810 (FIG. 8C). Stacking these segments provides a deflection angle 804α between each segment. When the taller segments are used in place of the shorter segments in an implant of a certain height, it should be appreciated that the fewer number of segments with the same deflection angle will sum to a lower overall deflection angle. The sum of the deflection angle can be increased or decreased by any combination of changing the individual deflection angle on any one or more segments, or increasing or reducing the number of segments used in the same linear length of the device. Although two tall segments are shown in FIG. 8D, the segment stack may include any combination of tall and short segments in a single implantable embodiment.

Figure 9A:
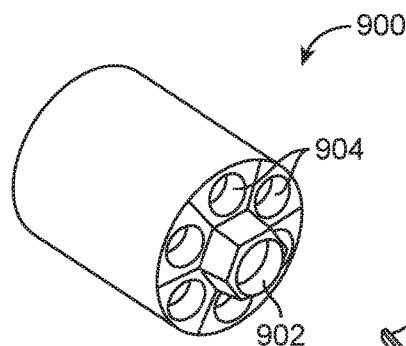
FIGS. 9A-9C provide alternative embodiments of segments.
Figure 9B:
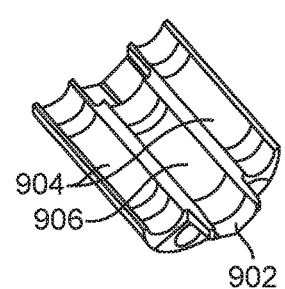
Figure 9C:
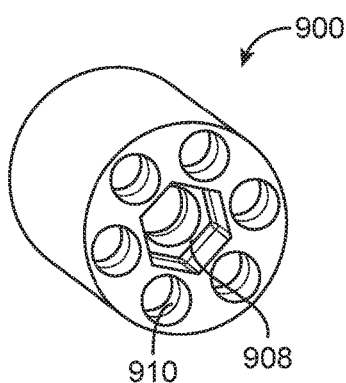
Figure 10A:
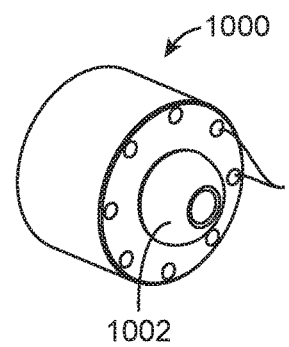
FIGS. 10A-10C provide alternative embodiments of segments.
Figure 10B:
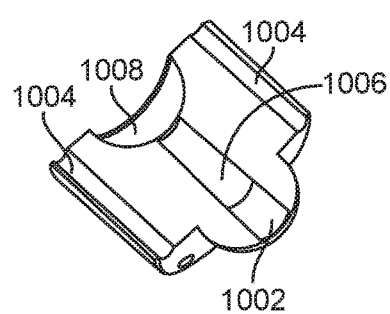
Figure 10C:
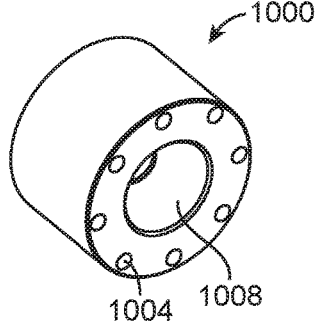

In some embodiments, the segments 900 (FIGS. 9A-9C) include six bore holes 904 disposed around the central bore 902 and configured for a maximum of six tensioning fibers. As discussed earlier, each bore hole or channel 904 may not need to have a tensioning fiber there through, and thus a fixation device having segments 900 may include three, four, five or six tensioning fibers, occupying at least three positions spaced at 120° around the periphery. Segments 1000 of FIGS. 10A-10C include eight bores 1004 disposed around the central bore holes 1002 and configured for a maximum of eight tensioning fibers. As discussed earlier, each bore hole or channel 1002 may not need to have a tensioning fiber there through, and thus a fixation device having segments 1000 may include four, five, six, seven or eight tensioning fibers, occupying at least four positions spaced at 90° around the periphery.

A few additional embodiments of segments 1100, 1102, 1104 are depicted in FIGS. 11A-11C. As shown in the various embodiments, the segments may have various diameters, lengths, pivot configurations, number and size of bores, and surface inclination angles. In an embodiment, as represented in FIG. 12, the body of a fixation device may be formed from segments of varying configuration stacked together. For example a proximal segment 1202, adjacent the proximal bone interface, may be longer if the initial portion of a bore in the proximal section of the bone to be treated is relatively straight. In embodiments, end segments may longer that those segments that are fixed about the curve, but distal segments should be navigable about the curve the support device is designed to treat thus limiting to some degree the length of the most distal segments. A next section of segments 1204 may have an intermediate height, for example about 160 mm, if the bore hole in the intermediate section is relatively straight with minimal bending. A distal set of segments 1206 may have a smaller height, for example about 80 mm, to accommodate bending about smaller radii. In an additional embodiment (not shown), proximal segments, such as segments 1202, 1204 may also have a diameter that is greater than distal segments, such as segments 1206, possibly requiring that bore hole in the bone be drilled with sections of different diameters.

Figure 13A:
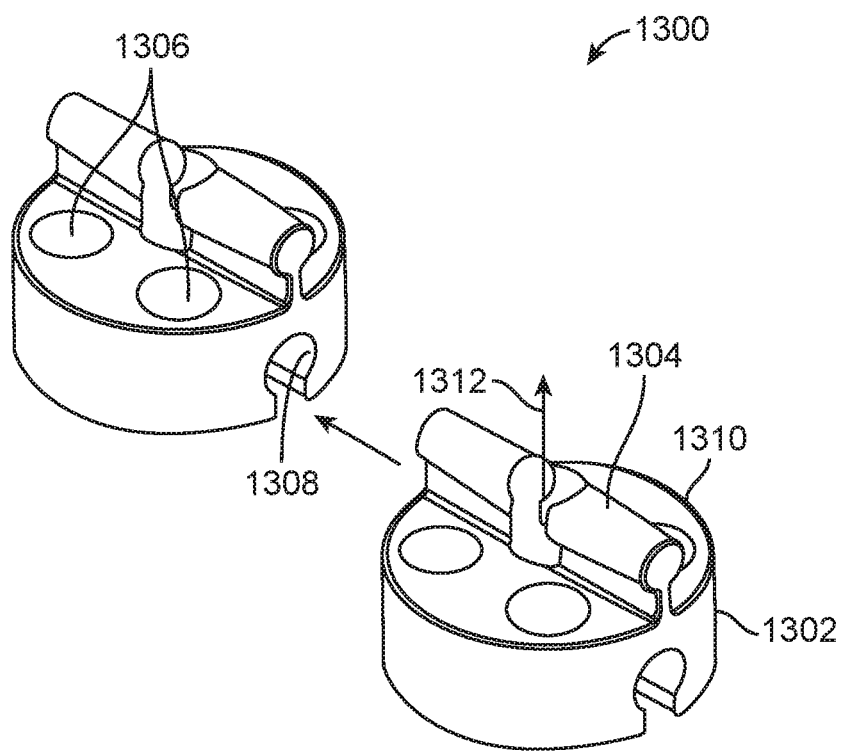
FIGS. 13A-13B provide an embodiment of a segment.
Figure 13B:

In some embodiment, the segment may include one or more fulcrum elements to facilitate or increase the off angle deflection between segments (FIGS. 13A-B). The segment 1300 has a base 1302 and a top surface 1310. The top surface has a fulcrum element 1304. In some embodiments, the fulcrum element 1304 may be rounded and symmetrical about the central channel 1312. The fulcrum element may have a taper, being generally larger toward the center (+) and gradually narrowing toward the perimeter or circumference of the base. In some embodiments, the fulcrum can be slidably engaged with a channel 1308 or aperture of similar dimensions (FIG. 13A). By using a fulcrum design on the positive relief component of each segment, the segments gain an angular deflection off the main axis in multiple directions while maintaining mechanical engagement with adjacent sections. This allows the segments to form a curve in two or more planes normal to the main axis while mechanically engaged to one another. The fulcrum allows greater flexibility between segments and does not require the device to have any specific alignment in order to generate a curved profile. The ability to remain in a loose, mechanical engagement with adjacent segments provides added capability in the device. A guide wire or guide pin may thread through the central channel and provide an overall shape to the device and the various segments.

Figure 14A:
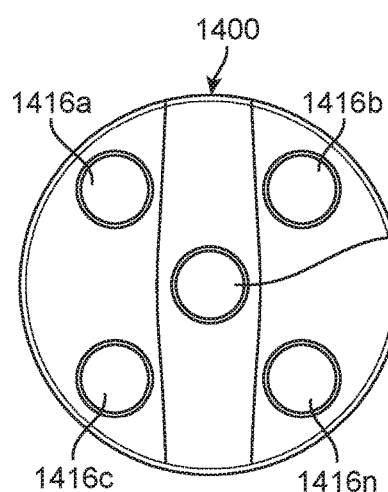
FIGS. 14A-14D provide an alternative embodiment of a segment.
Figure 14B:
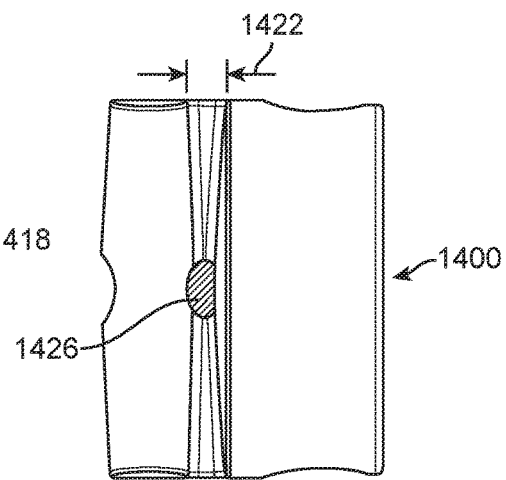
Figure 14C:
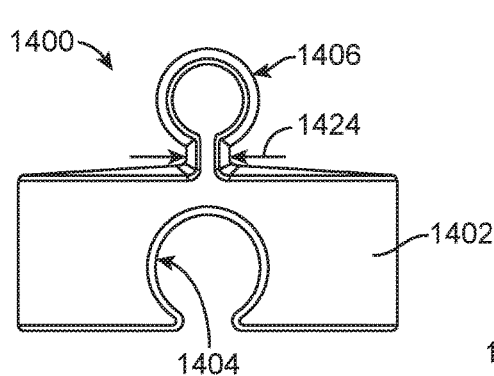
Figure 14D:
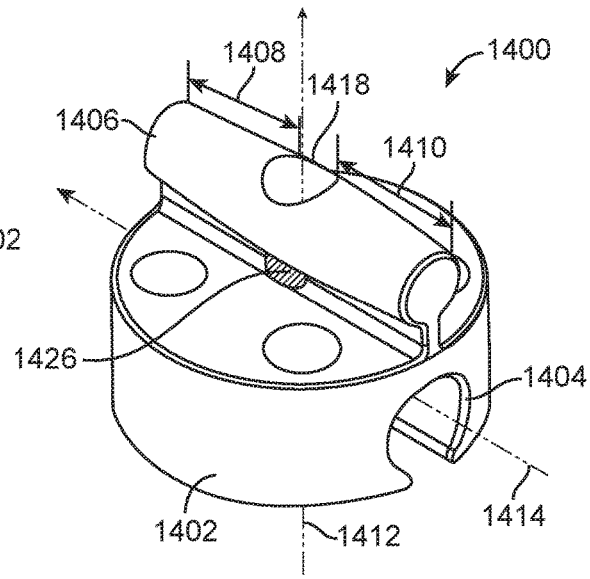

The fulcrum feature 1400 can now be seen in greater detail with four different views of the segment. In a plan view (FIG. 14A) the central channel 1418 and a group of peripheral channels 1416a-n can be seen. Although four peripheral channels are shown, it should be understood that the number of peripheral channels may be as few as 1 or as many as can be designed into the segment. Two side views of the segment 1400 are shown at 90 degree off sets. On one view (FIG. 14B), the side view reveals the central channel creates a hole in the neck region. The neck region raises the fulcrum above the top plate. Thus there may be a hole 1426 in the neck 1422 and 1424 of the segment. In the rotated side view (FIG. 14C), the aperture for the fulcrum pin 1406 can be seen. In these embodiments, the fulcrum pin 1406 and fulcrum channel 1404 are shown in parallel. However the fulcrum pin 1406 and fulcrum channel 1404 may be at any radial angle relative to each other. For example, the fulcrum pin and fulcrum channel may be offset anywhere from about 0 degrees to about 180 degrees where the fulcrum pin and the channel are symmetrical. Where the fulcrum pin is not symmetrical about the central channel, the fulcrum pin and fulcrum channel may be offset between 0 degrees and 360 degrees. Additional detail can be seen in a perspective view (FIG. 14D) of the segment with a fulcrum style positive relieve element. A circular perimeter 1402 can provide a smooth and atraumatic surface for the segment 1400. The fulcrum pin 1406 is a generally tapered pin (by way of analogy only the fulcrum pin may be thought of as a single piece wood rolling pin in shape) having a central channel 1418 through it. The central channel 1418 exposes a hole 1426 on each side of the neck 1424. A fulcrum channel 1404 goes through the segment 1400 and defines a fulcrum channel axis 1414. The fulcrum has two slopes 1408, 1410 from the central channel 1418. The two slopes 1408, 1410 may be the same, or they may differ in pitch, angle, shape or length.

Figures 15A, 15B:
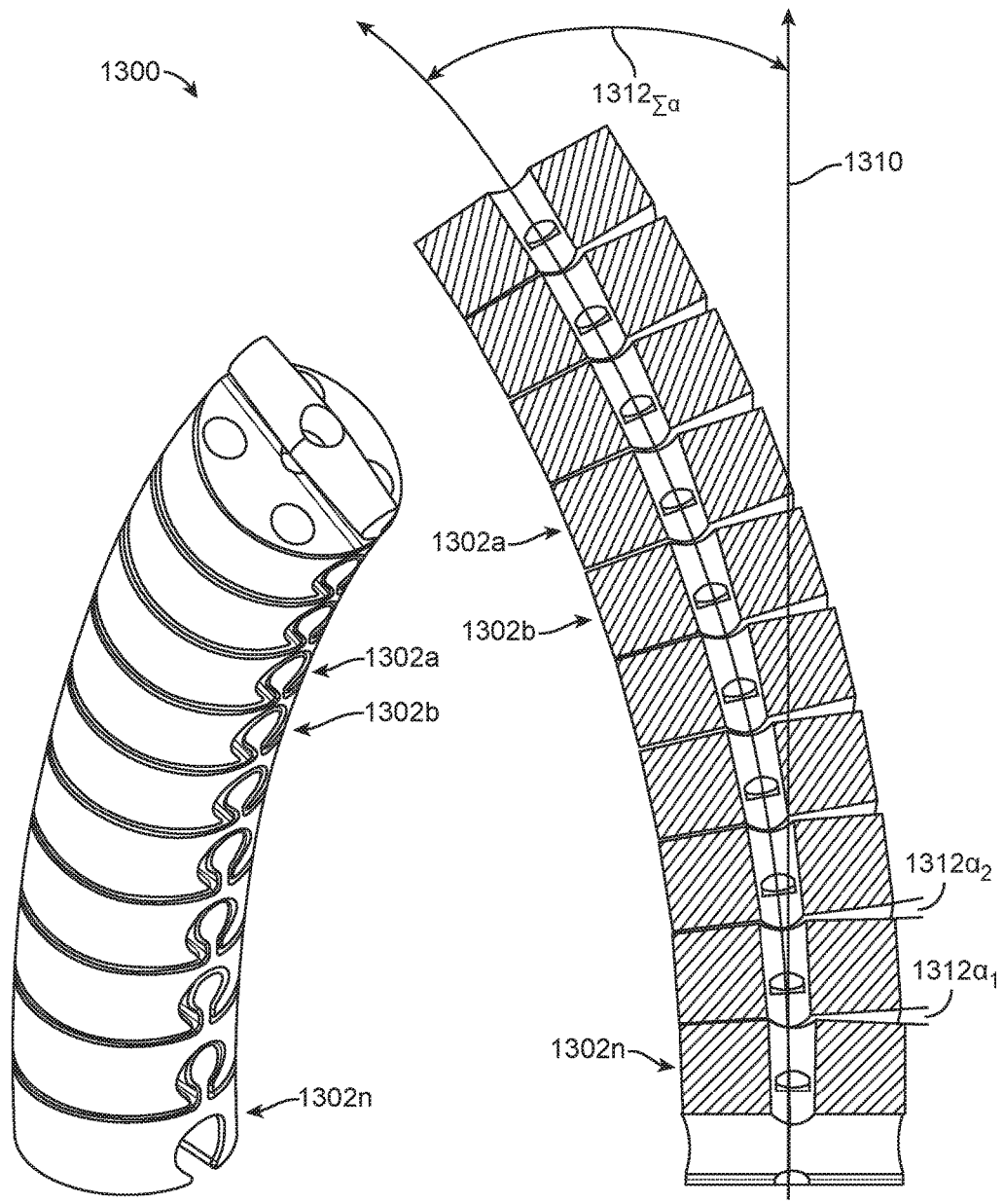
FIGS. 15A-15B provide a stack illustration of a segment embodiment.

An example of the fulcrum segments in a stacked arrangement is now shown in FIGS. 15A-B. The various segments 1502a-n of the stack are shown in a perspective view in FIG. 15A. The individual segments have bendability in multiple planes, including a plane parallel to the direction of the fulcrum pin. A cross section (FIG. 15B) shows the individual angle of deflection 1312α of the main axis 1310 and the sum angle of deflection 1312a-n.

Figure 16:
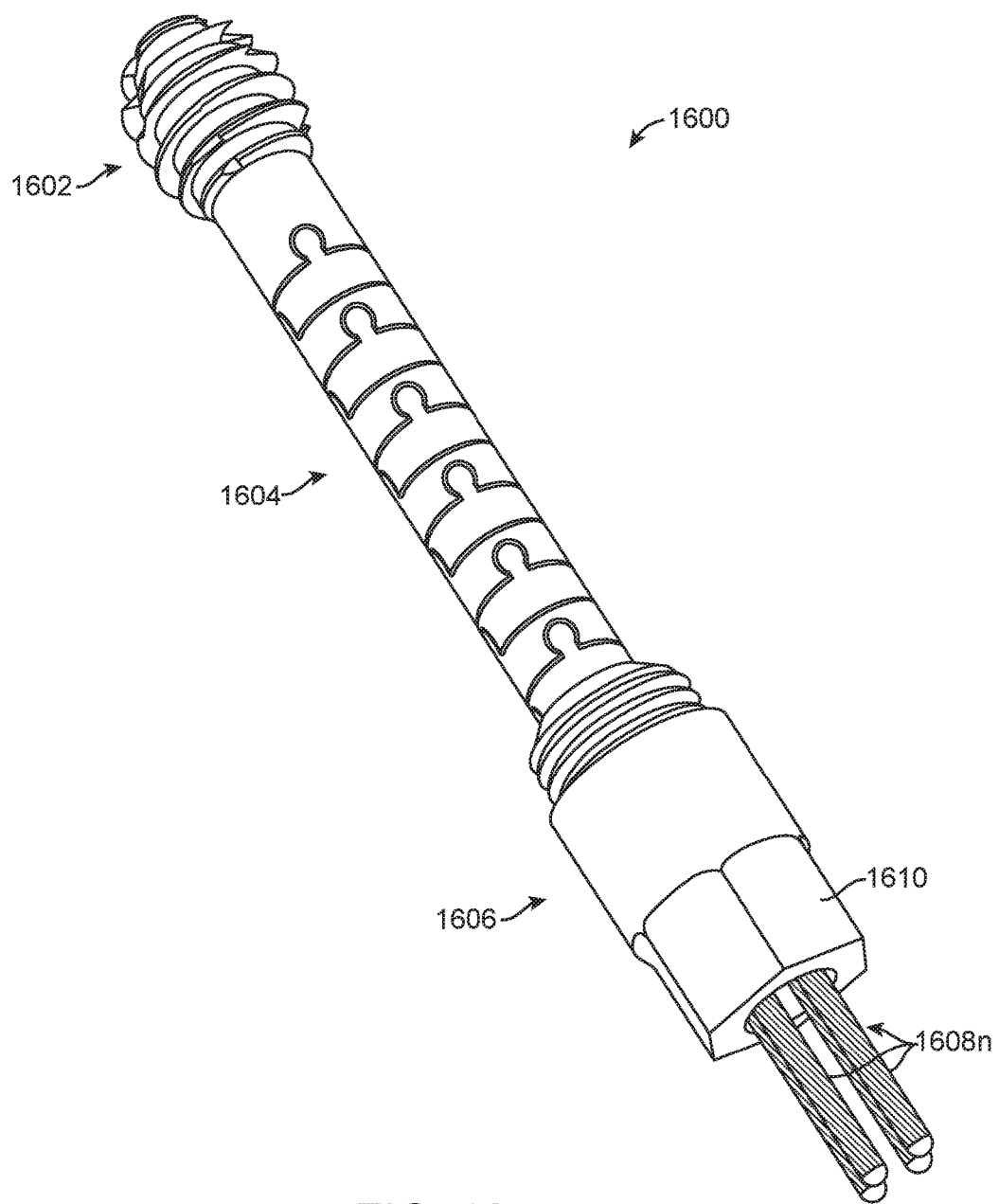
FIG. 16 provides a view of a device using a stack segment body.
Figure 17:
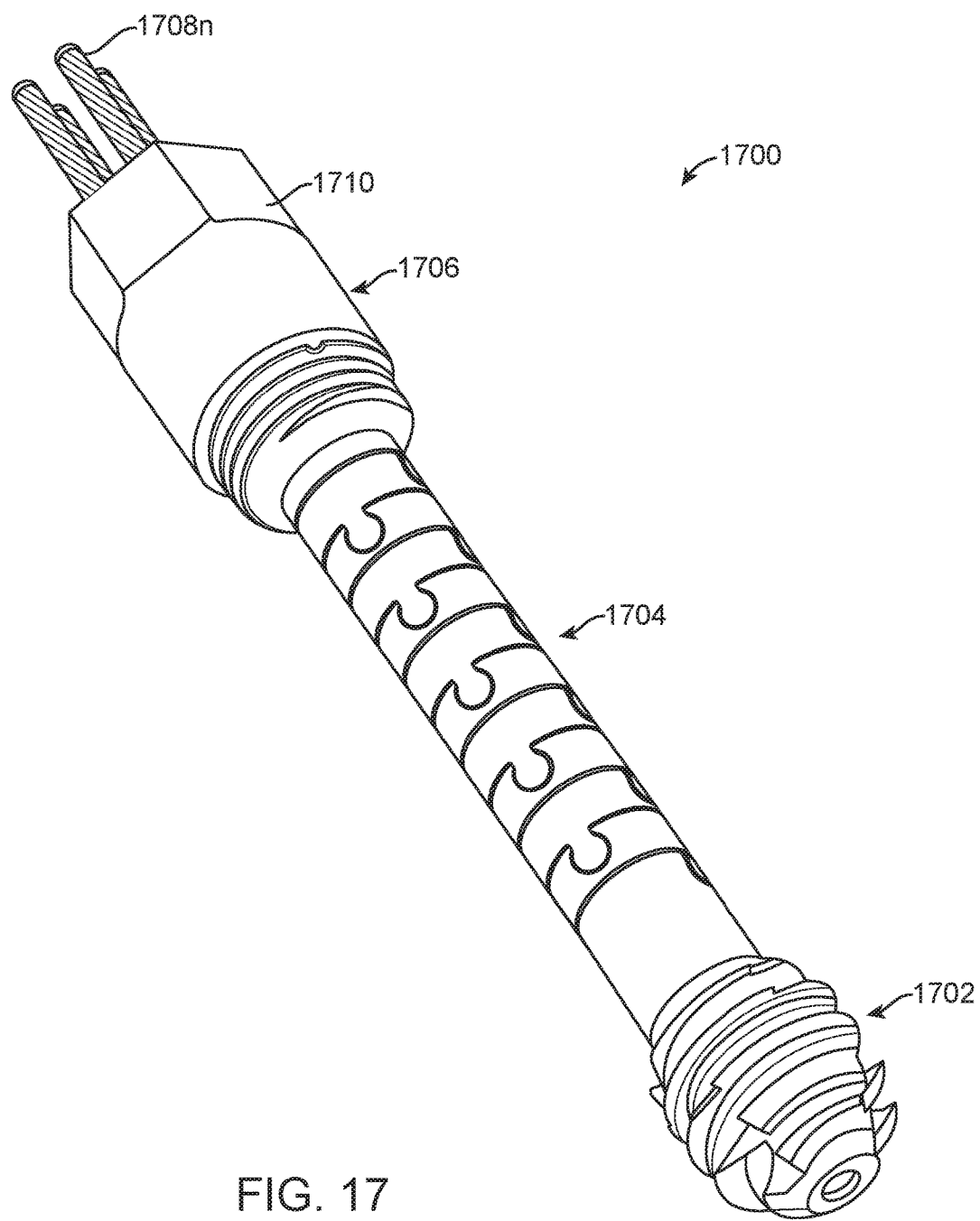
FIG. 17 provides an alternative embodiment of a device using a stack segment body.

In an alternative embodiment, the fulcrum segments are shown with the fulcrum pins at 90 degree angles to the fulcrum channels (FIG. 16). In this embodiment the device 1600 has a distal end 1602 having a screw engagement device for engaging in the boney tissue. The main body 1604 of the device 1600 is made up of fulcrum segments having fulcrum pins rotated 90 degrees from the fulcrum channels. The fulcrum pins and channels are able to engage mechanically and provide deflection angles between each segment and a sum deflection angle that is the net of each individual deflection angle. A proximal end 1606 is shown where individual fibers 1608n may be tensioned to hold the device 1600 in a desired shape. An alternative view of the device 1700 is provided in FIG. 17, having a distal end 1702, a body 1704 and proximal end 1706. The fibers 1708n extend from the proximal end.

Figure 18A:
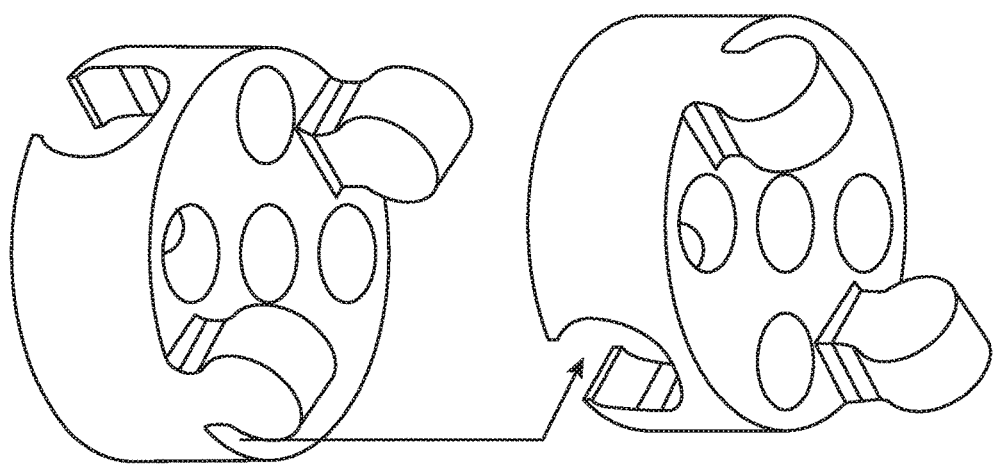
FIGS. 18A-18B provide an alternative embodiment of a segment with a fulcrum engagement.
Figure 18B:
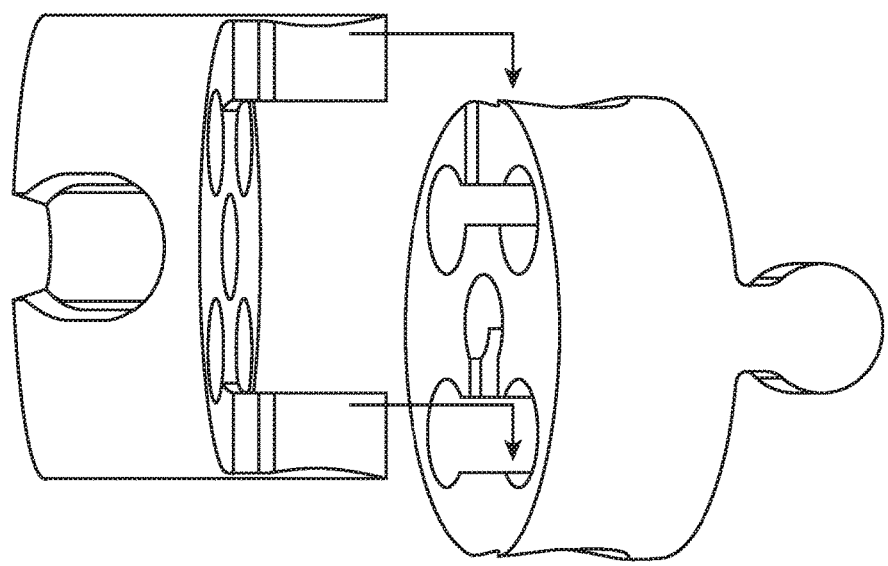
Figure 19A:
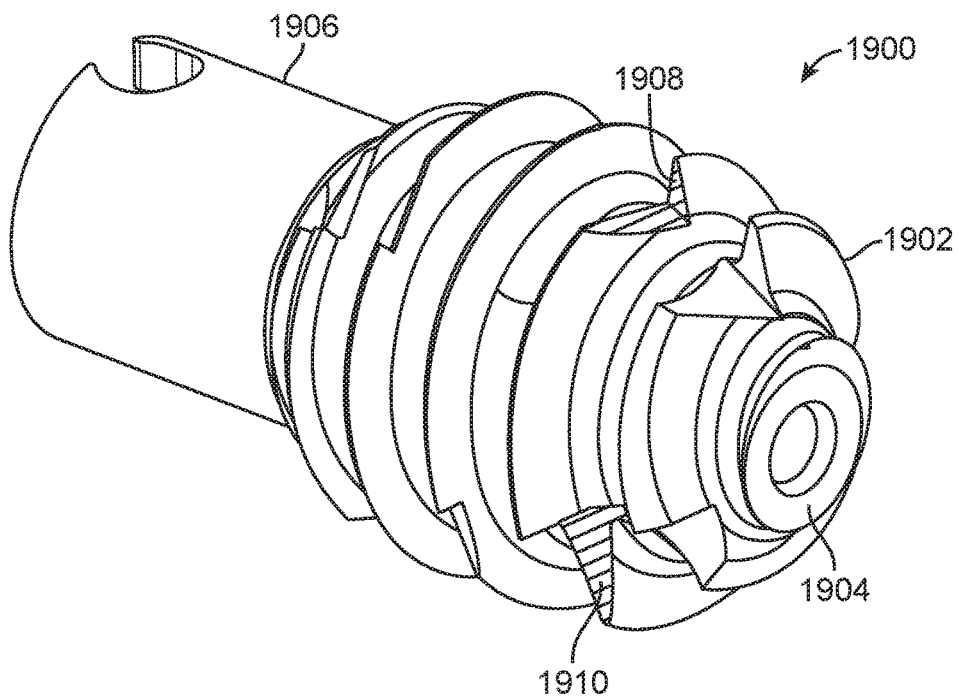
FIGS. 19A-19B provide two views of a distal section embodiment.
Figure 19B:
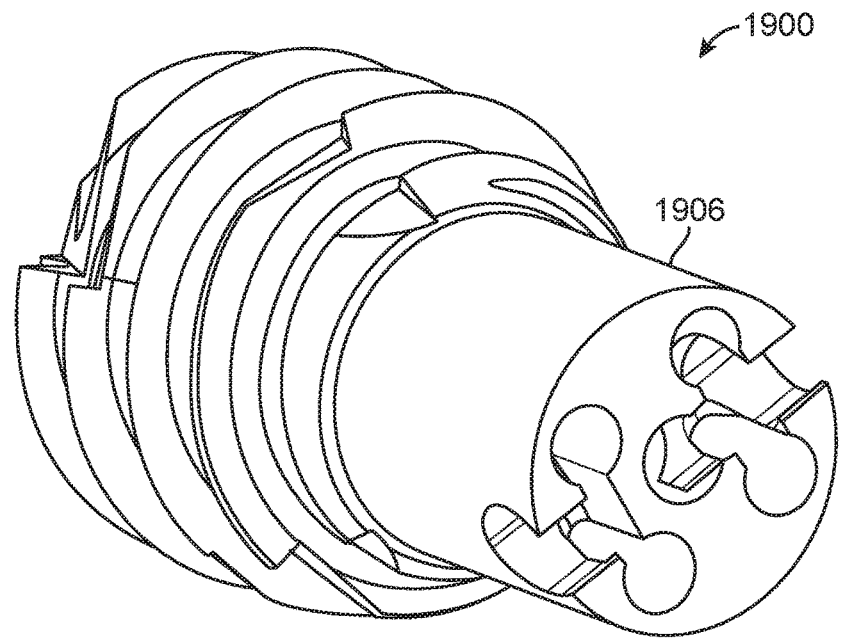

In some embodiments, the segments 1800a-n of the device may have replace the fulcrum pin and fulcrum channel individual round tabs 1802 (FIGS. 18A-B) and corresponding round apertures 1806 for receiving the tabs 1802. As previously described, the orientation of the tabs and apertures may be parallel or at any radial angle relative to each other along the circumference of the segment 1800. The segment tabs need not be round, they may be ball shaped, or have acute angles. A shaped slot feature 1810 may be made into one side of the segment to permit another segment to engage with the next segment. The sliding and stacking of the segments may be done one at a time or in groups of two or more.

In some embodiments, the distal end 1900 may have a segment engagement portion 1906 to engage the fulcrum channel or fulcrum tabs for receiving a fulcrum pin/tab from a segment. The distal end may also have a negative relief feature for receiving a positive relief feature of a segment. In still another embodiment the distal end may have a positive relief feature or fulcrum pin/tab for engaging a corresponding negative relief feature, channel or aperture on an adjacent segment. The distal end has a bone engagement feature 1902 like a screw thread. The screw thread may have optional detents 1908, 1910 in the threading to facilitate cutting into the bone for both clockwise and counter clockwise rotation. This helps in both placement and removal of the device should removal be required. A guide wire aperture 1904 may be provided so the distal end may slide over the guide wire.

Figure 20B:
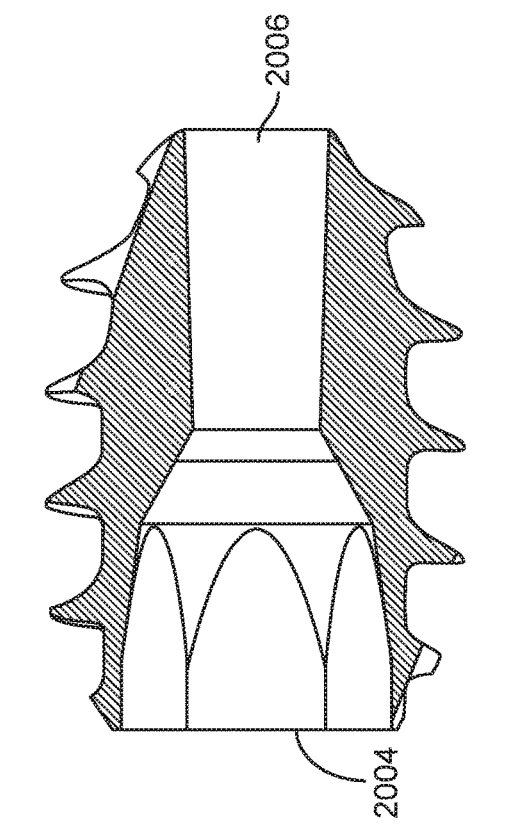
FIG. 20B shows a cut away view of a distal segment.
Figure 20A:
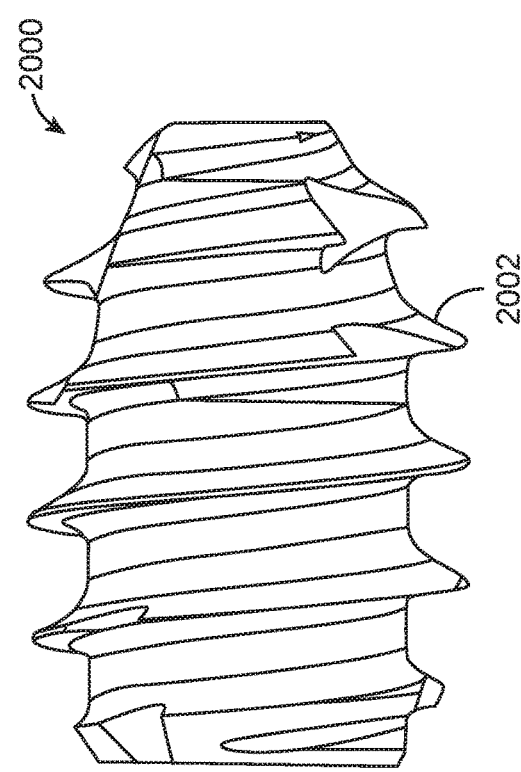
FIG. 20A shows a profile view of a distal segment.

In some embodiments the distal end may be a screw head having a generally tapered form with an oblong core (FIG. 20A). The distal end may have an internal negative relief feature for receiving a hex bolt or other connection element from an adjacent segment. The connection between the distal end and the distal most segment may be one where some angle of deflection is afforded to the overall device, or it may be a connection with a solid fit and not additional angle of deflection of the main axis is gained between the last segment of the main body and the distal end.

Figure 21:
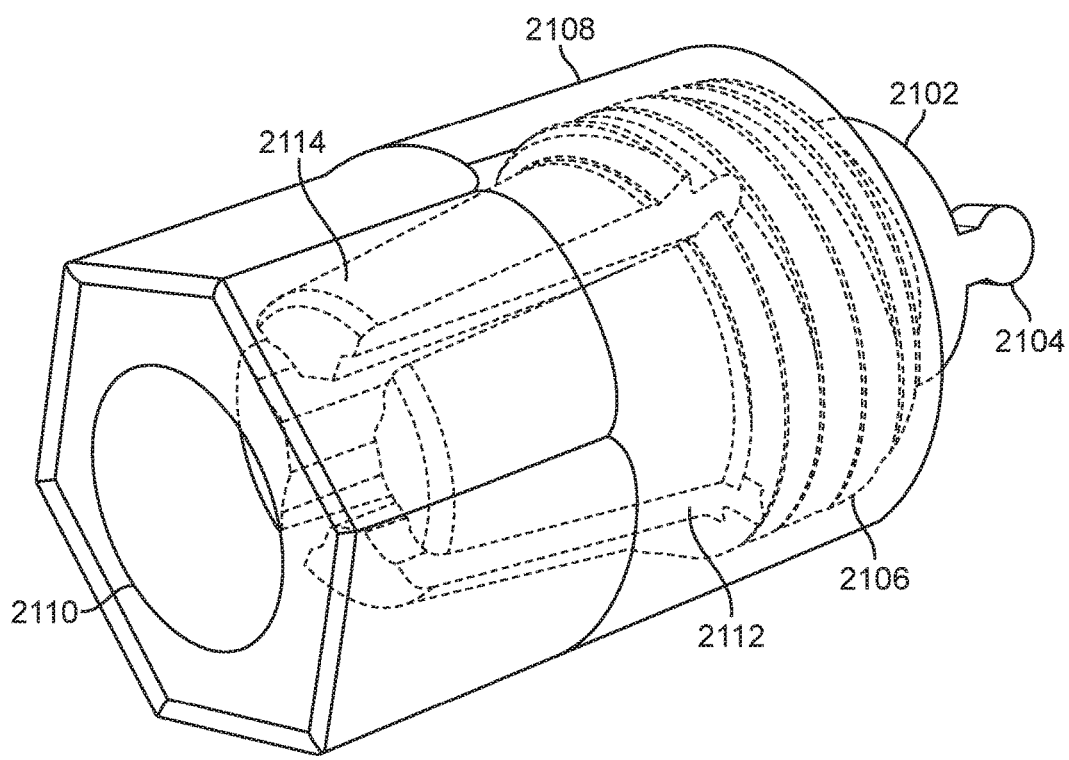
FIGS. 21 and 22 provide an illustration of proximal end cap.

An end cap 2100 is provided for securing the proximal end of the main body (FIG. 21). In an embodiment, the end cap 2100 fits over the proximal most segment 2102 of the main body. The proximal most segment 2102 may have a fulcrum tab 2104 for engaging other segments of the main body. The proximal most segment 2102 may also have a screw thread 2106 for engaging the end cap 2100. One or more fiber channels 2112 are provided for the fibers (not shown) to be gathered at the proximal end and drawn tight or simply fixed into position. The end cap 2100 slides over the proximal most segment and can be screwed on to the proximal most segment to engage the threads 2106. The end cap 2100 may be tightened by hand by grasping or engaging the back section 2114 which may have a roughened surface to facilitate gripping. Alternatively the back section 2114 may be engaged using a torque driver. An optional aperture or hole 2110 may be provided for the guidewire, fibers or other loose ends that may trail from the device to be threaded through and removed after the device is placed and capped. In some embodiments, the device is driven in to the bone via a torque driver transmitting torque directly to the proximal most segment 2102. The torque driver (not shown) would be adapted to accommodate the shape of the proximal end of the proximal most section. In some other embodiments, the device may be driven in to the bone with a torque driver applying torque to the end cap 2100.

Figure 22:
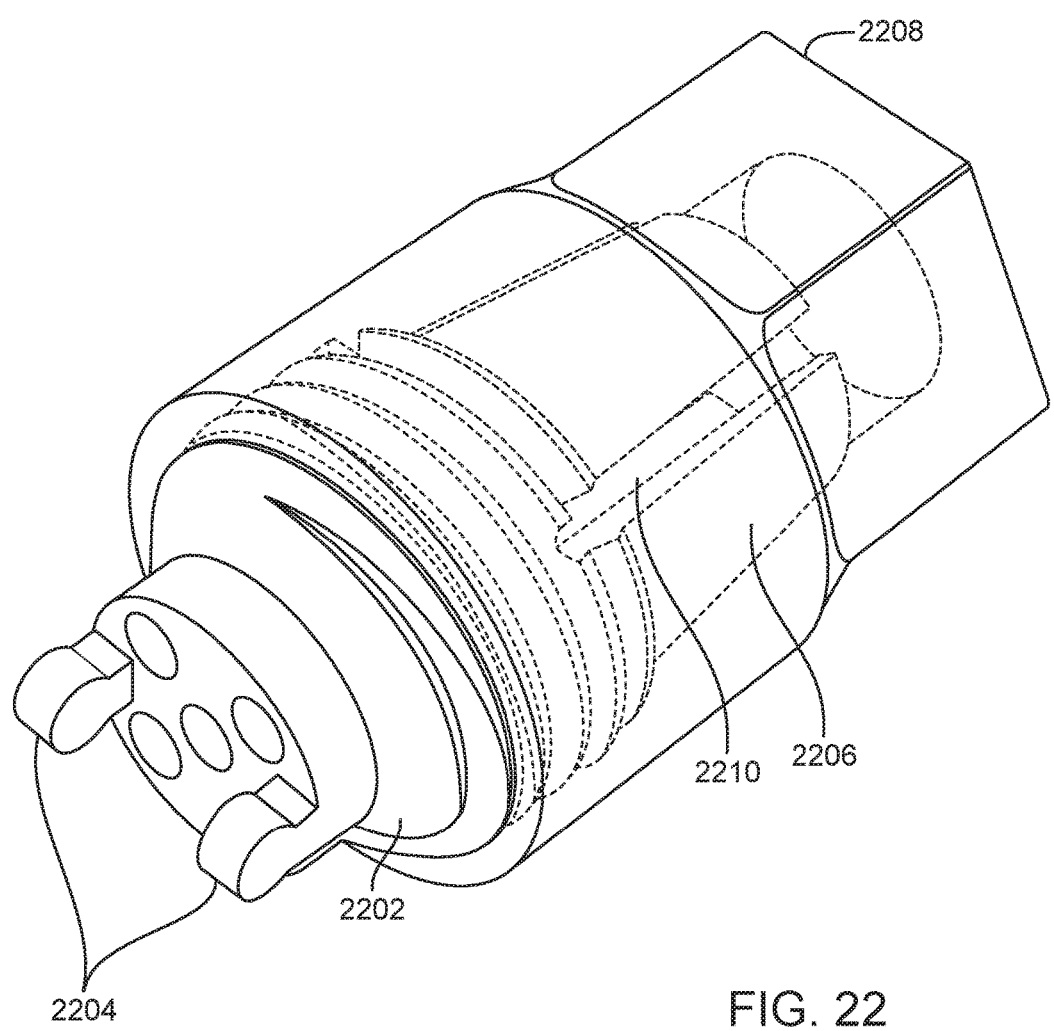

The end cap 2200 is now shown in a different perspective angle (FIG. 22). The operator may hold the fibers in a group and place them into the thread channels 2210 and secure them in place. Generally one fiber per channel, but the channels may be designed and cut to accommodate more than one fiber. Between the channels are tabs 2206 which are optionally intended to engage a torque transmission device to help drive the device into the bone. Once the fibers are secured, the end cap 2200 may be screwed into place over the proximal most segment 2202. Note the proximal most segment has a pair of fulcrum tabs 2204 for illustration purposes only. The fulcrum or connection/engagement mechanism to other segments of the body may be any kind.

In some embodiments, the proximal end may be any form that can receive a torque transmission device and transmit torque to the body and the distal end of the device. Various non limiting shapes adapted to receive torque transmission devices are shown in FIGS. 23A-23F. In one non limiting embodiment, the relief feature for engaging a torque transmission device is a positive relief feature 2300 having an end flange 2304 to prevent the proximal end from being pushed into the bone past the hard cortical wall. In some embodiments there is a negative relief feature 2308 for receiving the male end of a torque driver. A flange 2312 or other feature is used again to help prevent the proximal end from being driven past the hard bone wall. A hole or aperture 2306, 2310 is made in the proximal end for the passage of a guidewire.

Figure 24A:
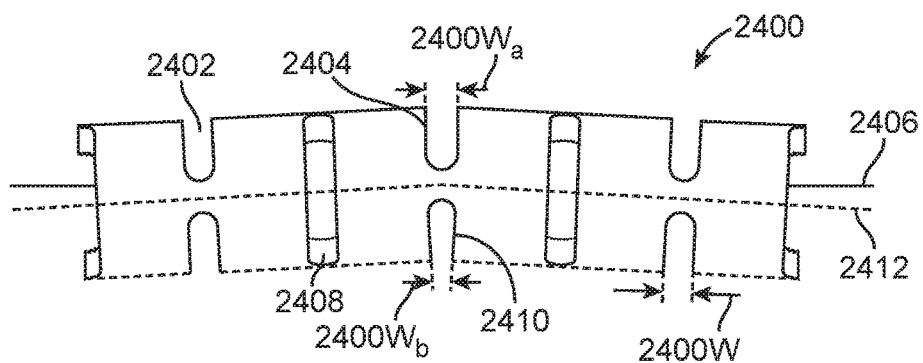
FIGS. 24A-24D illustrate a toothed interior embodiment.

FIG. 24A shows an alternative embodiment of a body 2400 having pairs 2402, 2408 of slots disposed circumferentially around the body tube, and offset by about 90° from each other. In an unbent state, the slots may have a width 2400w. The body 2400 is bent downwardly away from the linear axis 2406 and defines an offset axis 2412 wherein a width $2400w_b$ of at least one slot 2410 on the lower side may be narrowed and a width $2400w_a$ of at least one slot 2404 on the upper side may be increased to allow the body to bend downwardly.

Figure 24B:
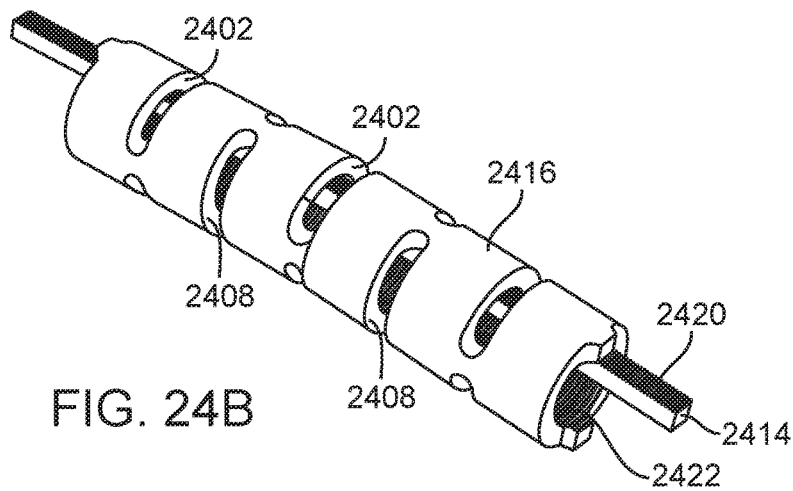
Figure 24C:
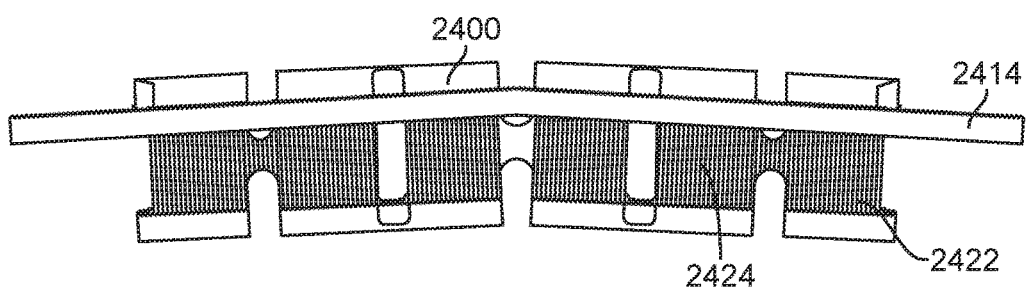
Figure 24D:
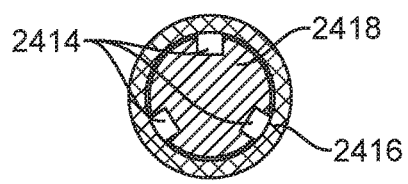

In some embodiments, as represented in FIGS. 24B, 24C and 24D, the body 2400 may be locked in its bent configuration by providing radially inwardly disposed teeth 2422 on the interior surface of the body 2400, which teeth extend through the main body. One or more externally toothed fibers 2414 may be inserted within the central cannula 2424. The toothed fibers 2414 may include teeth 2420 that match the pitch of the teeth 2422 (or threads) on the inside of the outer member so that the teeth on the fibers may engage with the teeth on the interior surface. In the flexible state, the internal fibers 2414 in the main body have sufficient diametric clearance to translate axially through the main body. In these embodiments, the tooth pitch is generally fine scale so a series of engaged teeth form between the inside of the body and the toothed fibers. Where the device has a bend in it, and the tooth frequency changes over any particular length, the fine scale of the teeth allows gaps and teeth to engage on a less than 1:1 or more than 1:1 ration and still provide gripping or engagement friction so the parts remain relatively stationary to each other when in a fixed shape.

In an embodiment as shown, the fibers 2414 may have a rectangular cross-section with teeth 2420 on one surface thereof. In alternative embodiments, the fibers 2414 may have teeth on each surface, or the fibers may have a circular cross-section and may have circumferential teeth or threads. To provide and maintain engagement of the teeth 2420 with the teeth 2422, an internal core component, or filler 2418, shown in cross-section in FIG. 24D, may be inserted longitudinally into the cannula 2424 to hold the fibers 2414 adjacent the interior walls.

The entire main body may be converted to a rigid state upon the insertion of the filler 2418, which pushes the teeth 2420 of the internal fibers 2414 against the teeth of the main body, meshing the threads/teeth of the internal members, creating a load path from one rigid section of the main body to the internal tension members, (bypassing the flexible section of the main body) to the next rigid section of the main body. The fibers 2414 may terminate within the main body, or in members attached to either end of the main body, for example, the proximal or distal bone interfaces. The internal core, or filler 2418, may be formed of materials that are flexible (bendable) for insertion along a curved path, but minimally compressible so that the fibers 2414 remain pressed into engagement with the interior surface. Some examples of materials from which the filler 2418 may be constructed include, but are not limited to SS 316LVM, Titanium Grade 23 6Al-4V ELI, PPEK or any 236LVM Stainless steel, polyether ether ketone (PEEK), or other materials as described herein.

In an embodiment, wherein three fibers 2414 (shown in cross-section in FIG. 24D) may be internally disposed within the body 2400, the fibers may be disposed at about 120° with respect to one another to thereby prohibit movement (bending) in all directions orthogonal to the longitudinal axis. In additional embodiments, additional fibers may be disposed within the cannula to provide additional shape-locking capability. For example, four fibers may be circumferentially spaced at about 90° from one another, or six fibers may be circumferentially spaced at about 60° from one another, or eight fibers may be circumferentially spaced at about 45° from one another. The number of fibers may be varied depending on the diameter of the body, and/or the intended use, such as severity and location of the fracture and stress that may be applied to the fractured bone.

Figure 25:
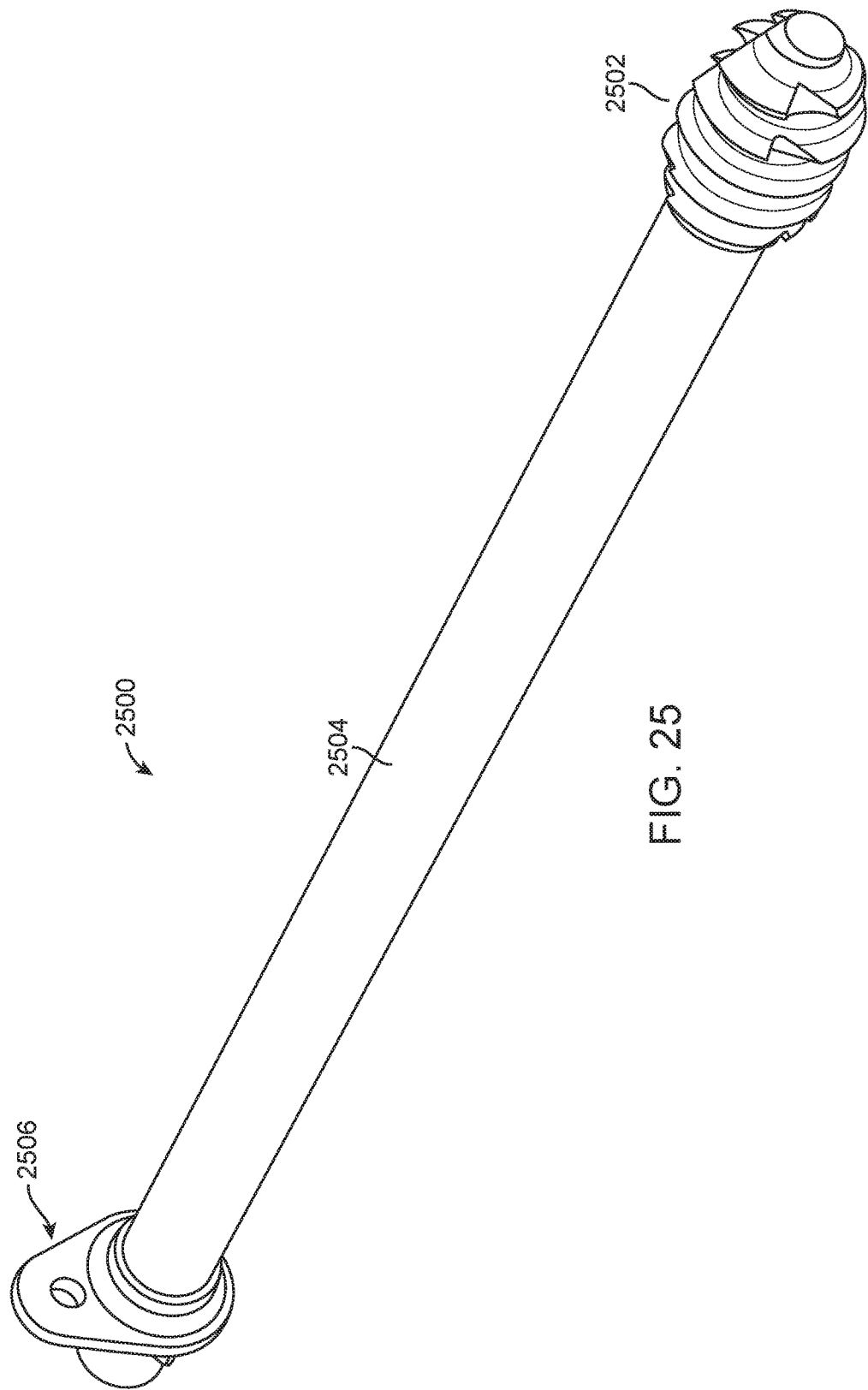
FIGS. 25 and 26 illustrate a unibody type device.
Figure 26:
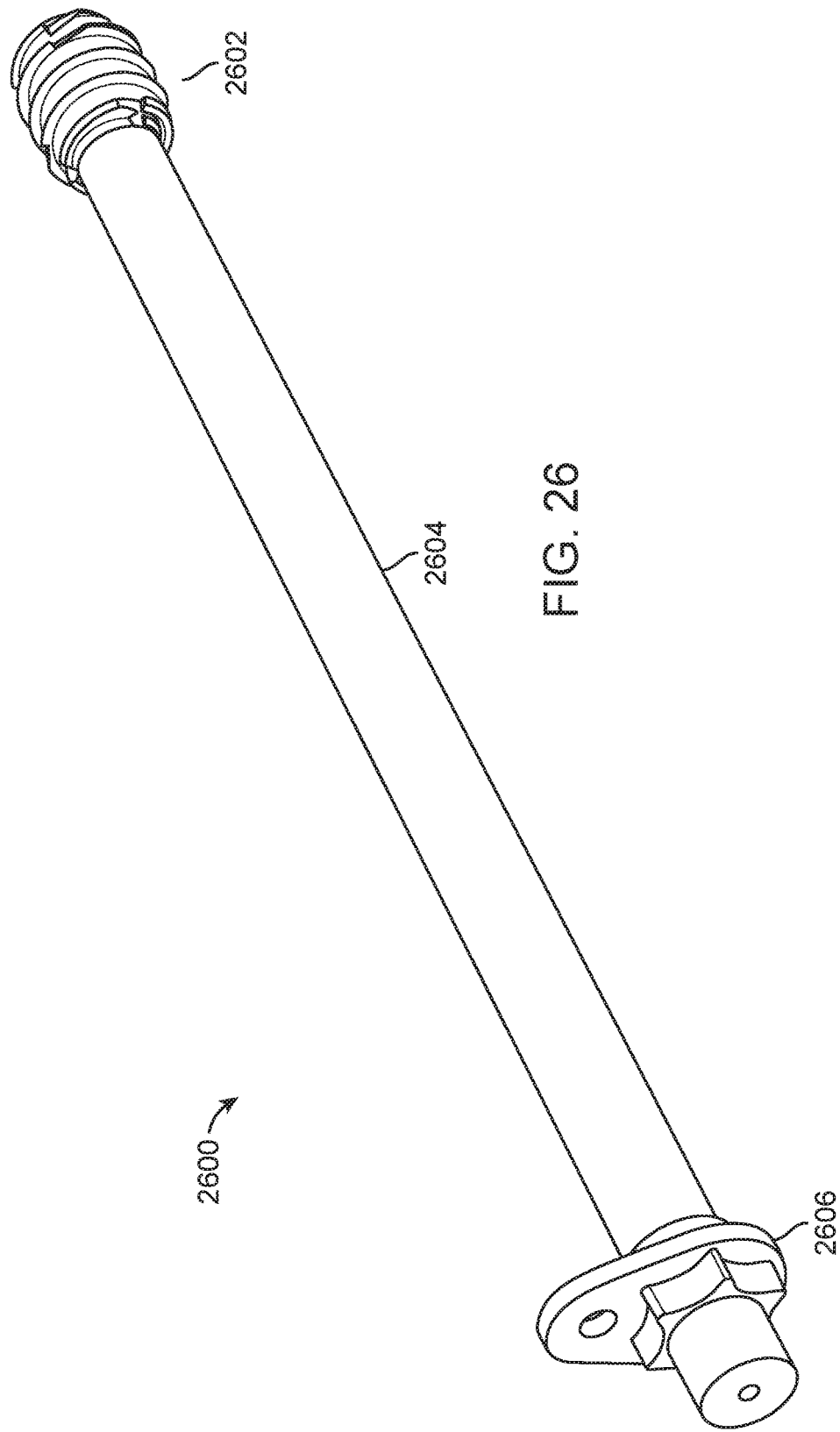

In some embodiments, the body 2504 of the device 2500 may be made of a single component (FIG. 25). In these embodiments, the body may be made of a flexible polymer material, a flexible metal or alloy tube or a combination of both. In some embodiments, the flexible tube may draw from existing manufacturing techniques for catheters, endoscopes and other minimally invasive medical device designs. In some embodiments the distal end 2502 retains a screw thread for engaging boney tissue and a torque transmission proximal end 2506 to allow torque to be transferred from the proximal end, along the body and too the distal end. The body may be a multilayer polymer device with metal wire or ribbon braid. Such a design may have added rigidity to enhance pushability and torquability. In some embodiments a catheter or endoscope construction technique can allow for an enlarged central lumen, through which a multi segmented body or other core like device may be inserted. In some embodiments the single tube body device may have a flange on the proximal end to act as a stop and prevent the device from being inserted too far into the bone (FIG. 26). The proximal end may be equipped with a flange 2606 so the device 2600 does not become completely inserted into the intramedullary space of the bone. Such an insertion may make retrieval and removal of the device difficult. The device 2600 has a body 2604 which may be a unibody design or a multi-segmented body. A distal end 2602 is also provided.

In some embodiments, the device 2700 may use a tube or other design for the main body 2704 having a series of slots, apertures or other stress relief elements built into the body structure. In an embodiment, a series of slots $2708_{a-n}$ are constructed as part of the body 2704. When torque is applied to the proximal end 2706, the body 2704 can transfer the torque to the distal end 2702. The individual slots or apertures $2708_{a-n}$ provide stress relief or enhance torque and flexibility, allowing the body to rotate on its axis and deliver torque to the distal end with compromising the structural integrity of the device. The body 2704 may be solid or hollow, or multi lumen with various component layers. In some embodiments the body 2704 may have a large central lumen to accommodate a multi-segment core or other material to provide enhanced structural features, allowing pushability, torquability and radial stiffness.

Figure 27:
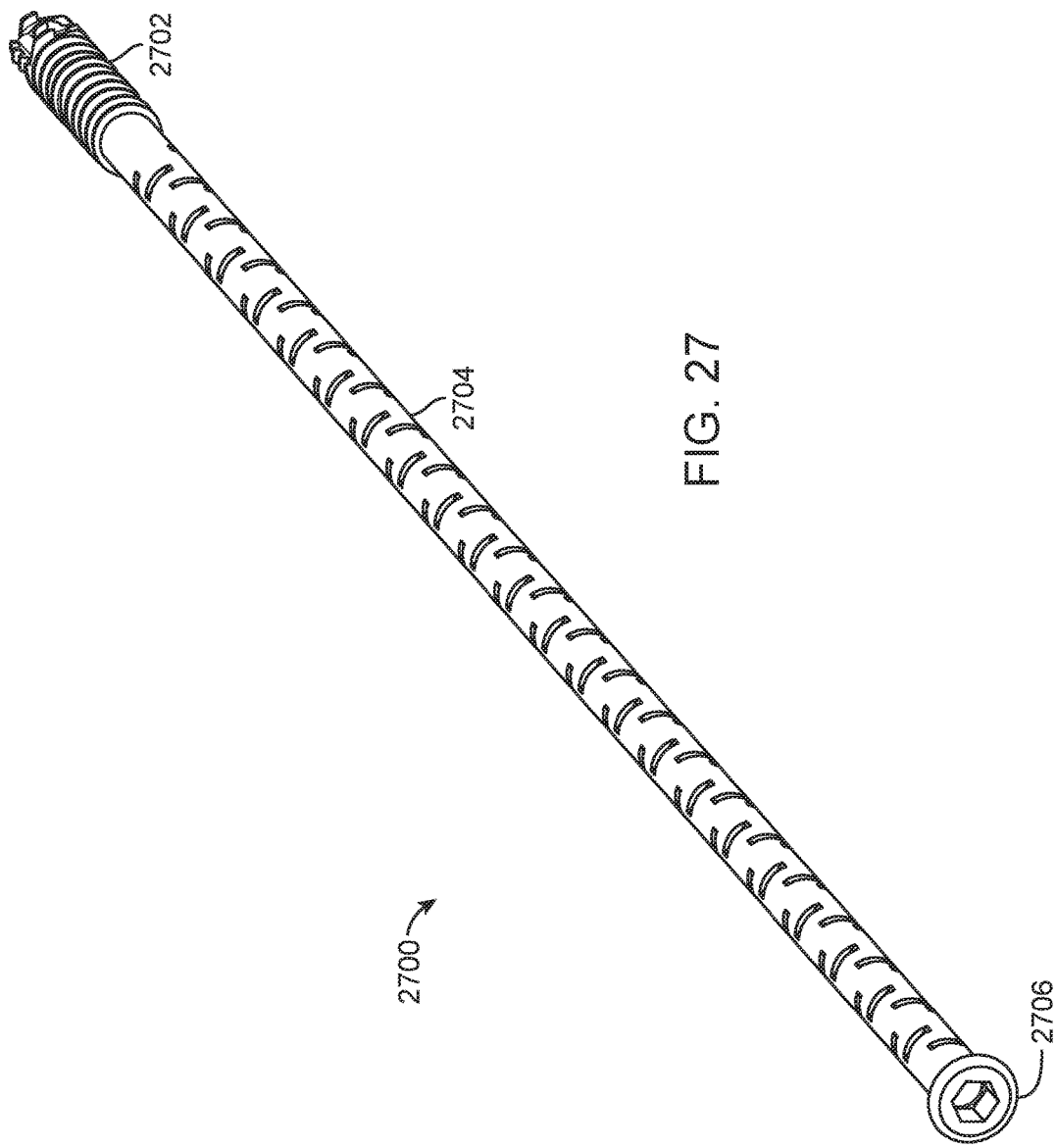
FIGS. 27 and 28 illustrate a unibody design with stress relief features.

In an additional unibody-type configuration, a unibody support device 2700 may be constructed of a non-flexible, torsionally stiff material, such as, for example, titanium as presented above (FIG. 27). In an embodiment, the body 2704 may be include a plurality of spaced apart slots $2708_{a-n}$ or other apertures that extend circumferentially about a portion of the exterior surface. The apertures may be arranged following a helical pattern around the tube shaped body. In an embodiment the slots may be configured as pairs, with each slot of a pair being disposed at about 180° from the other slot of the pair, thereby allowing for widening of the slot on one side, while the opposite slot is narrowed for bending in the direction of the narrowed slot. As shown, the slots $2708_{a-n}$ may also be circumferentially offset from one another. In an embodiment, the slots may be circumferentially offset from each other by about 60° to 90°, thereby allowing for bending of the body 2704 to occur in a multiplicity of directions, as may be required for cannulae of complex curvature, or curvature in more than one plane.

Figure 28:
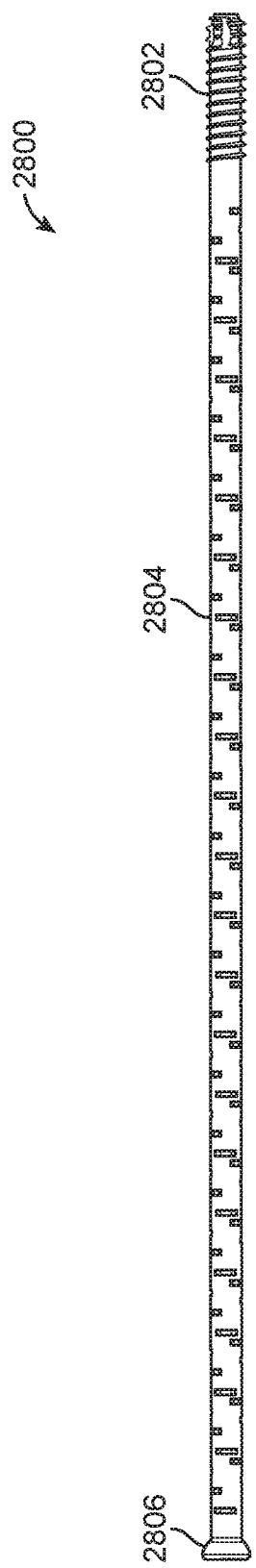

The distal bone interface 2702 and the proximal bone interface 2706 may be integral with the body 2704, or may be separate attached components, of any of the embodiments as discussed herein. The proximal section 2706 depicts a radial flange for axial bone fixation, and depicts a negative relief hex configuration for torque transmission, and the distal bone interface 2702 is depicted as a threaded screw head with bone cutting threads. The bone cutting threads may be regular pitch or variable pitch, continuous or interrupted/interval; type. In some embodiments, threads may be replaced or augmented with spikes, pins, nails or any other mechanism in addition or alternative to screw threads. A profile view is now shown in FIG. 28, having a profile view of the device 2800 with a proximal section 2806, body section 2804 and a distal end 2802.

Figure 29A:
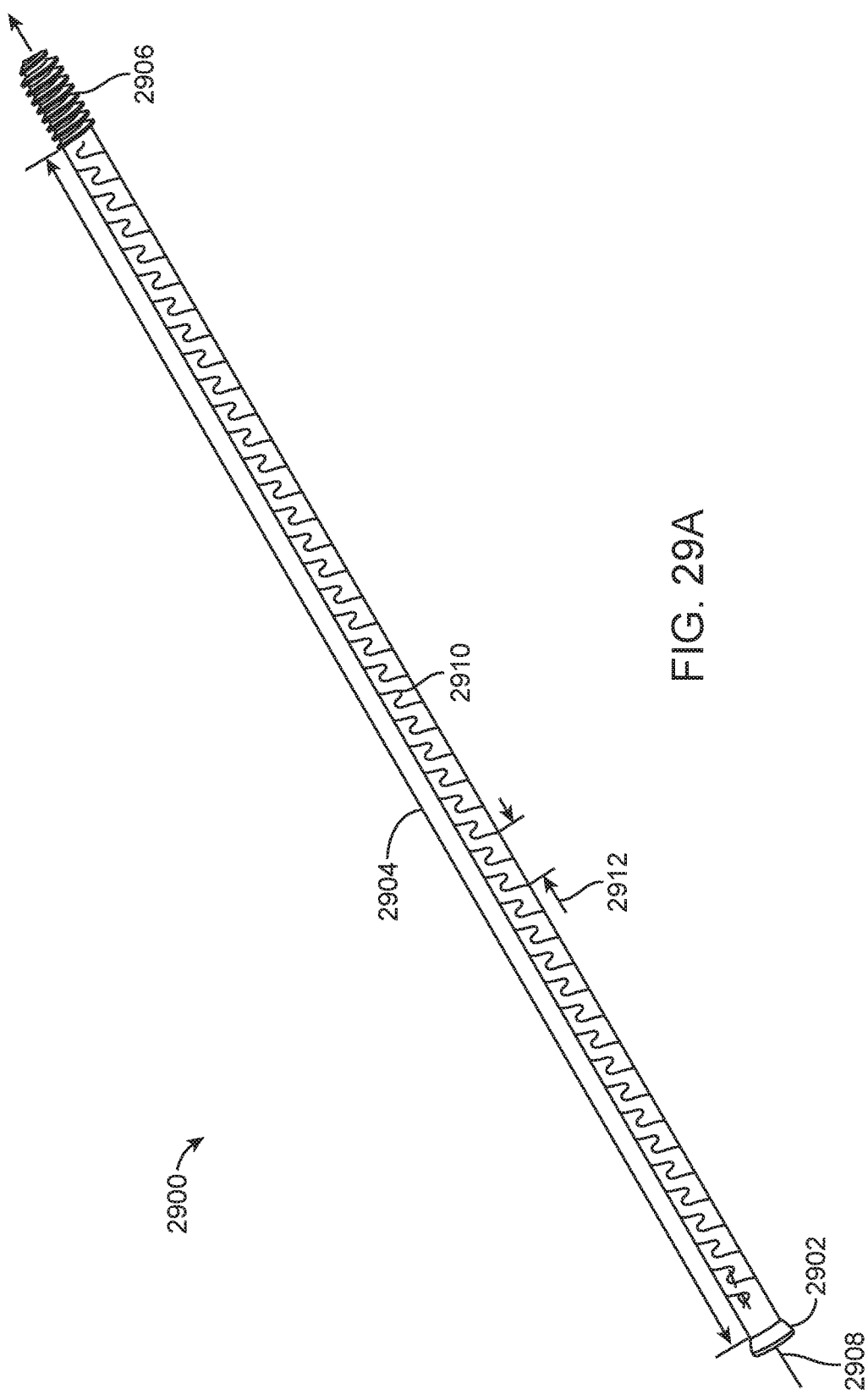
FIGS. 29A-29B illustrate a unibody design with a cut line.
Figure 29B:
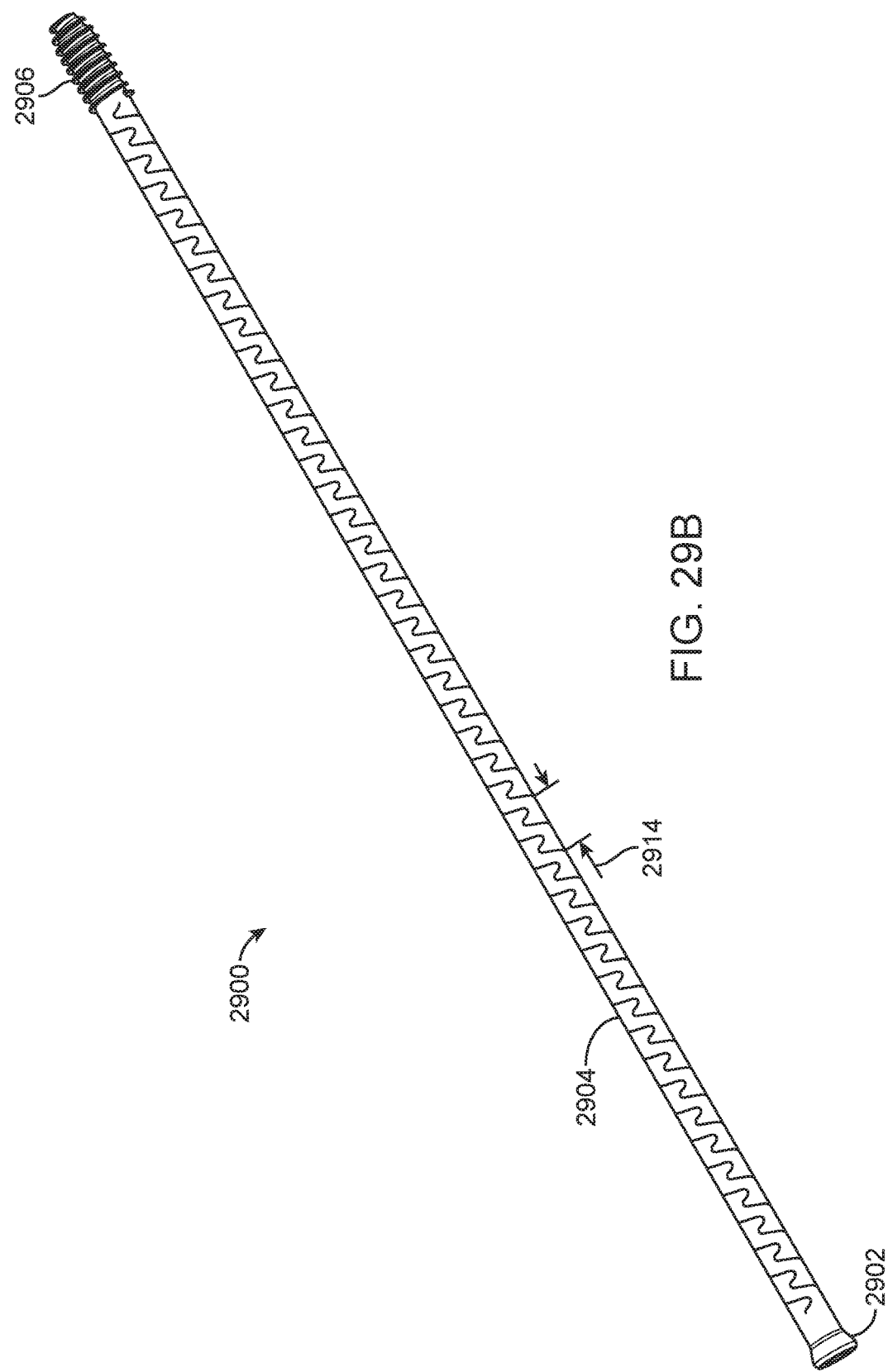
Figure 30:
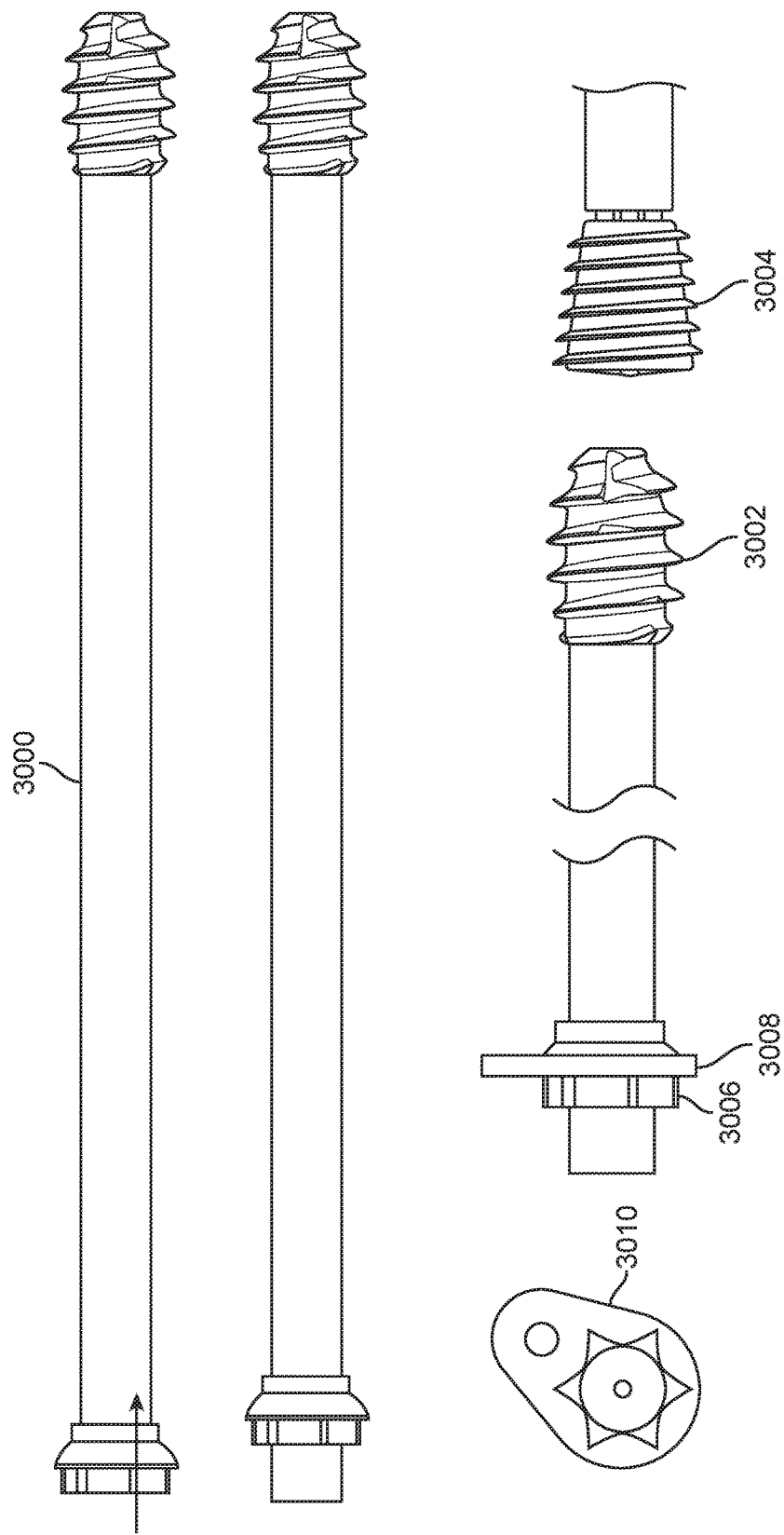
FIG. 30 illustrates various embodiments of a proximal end.

In still other embodiments, the device 2900 may have a body 2904 made from a single tube, but cut using any acceptable cutting technique (laser, EDM, mechanical blade) to produce a long continuous scar or slice through the tubular body (FIGS. 29A-29B). The cut 2910 may be completely through the tube body so the cut punctures the shell of the tube, or the cut may be an etching or partial cut that produces a gouge or trench in the tube body without penetrating the tube body. In some embodiments the cut 2910 may be alternating cuts through the tube body and gouges that do not penetrated to the interior of the tube body. One may imagine this sort of scoring as a dashed line of through cuts and partial cuts. The device 2900 has a distal section 2906 and a proximal section 2902. The device 2900 in a linear state defines an axis 2908, and the type of cut line 2910 and its depth in the body will define how far the device 2900 can be deflected or bent off its main axis. The cut line 2910 may be made to start at one end of the tubular body and continue to the other end. The number of turns the cut line 2910 makes in a given unit of linear length defines the frequency 2912 of the cut line. Generally the higher the frequency, the greater deflection off the main axis the device 2900 can make. Alternatively by increasing the width of the cut, a similar result (greater angle of deflection) can be achieved. The cut line 2910 may have variable cut width as well as depth.

The proximal end may come in a variety of shapes, sizes and features. In some embodiments of the proximal end, there may be a flange 3008, 3010 of varying shapes and sizes. The flange is generally intended to prevent the proximal section of the device 3000 from being inserted past the cortical wall of the bone being treated. Access to the proximal end is generally important in case the patient has a post operative complication which requires removal of the device. The medical professional then needs ready access to the device without being required to dig into the bone to retrieve the device. A flange or similar feature may be used to prevent the device from being inserted too far into the intramedullary space. In some embodiment the proximal end 3004 may be tapered such that part of the proximal end can enter past the cortical wall and part of the proximal end cannot enter past the cortical wall. In some embodiments the proximal end may be threaded so there is a feature or element that will engage the cortical wall. The distal head 3002 similarly may have a bone engagement thread.

In some embodiments, the distal end may use articulable disks 3102 and clamps 3112 to engage the bone. In some embodiments, the disks 3102 are provided in a first position which is narrower in profile to allow insertion into the intramedullary bone space (FIG. 31). The clamps 3112 are in a low radius configuration to allow the device to be advanced. When the device is in the proper location, the disks 3104 compresses on the clamps 3114 forcing the clamps radially outward, and thus engage the boney tissue. This action may occur when the fibers are drawn tight, or when the device is withdrawn slightly to cause the disks or clamps to engage the boney tissue, or the disks or clamps may be actuated using some sort of user control mechanism. Various non-limiting designs for the disks and clamps are provided 3106, 3108, 3110. The clamps may be similar to washers or lock washers in shape.

In some embodiments, placement of the device may be facilitated by using a curved intramedullary fixation (CIF) steerable guidewire, or simply guidewire 3300 (FIG. 33). The guidewire 3300 maybe one generally used in orthopedic procedures, and may be about 0.3 mm to 6.0 mm in diameter. The diameter of the guidewire can be selected by the medical professional and appropriate for the bone the guidewire will be used on. The guidewire 3300 has a bend 3302 near the distal end 3304, and the distal end may be tapered to a point. In operation, a medical professional may pass the guidewire 3300 down the bone and tap on the proximal end of the guidewire to incrementally advance the guidewire in the intramedullary space of the bone. The guidewire is rotated so the bend 3302 portion of the guidewire is angled toward the cortical wall. Thus when the user taps on the proximal end of the guidewire, the distal end is deflected away from the cortical wall when the bend portion impacts the wall. In this manner, the guidewire may be continuously rotated by the medical professional under visualization so the guidewire creates a curved path through the intramedullary space.

The guidewire, the device and other components as described here in, may be made from a wide range of materials. In the various embodiments described herein, the device and the guidewire may be composed from a polymer, a metal, an alloy, or a combination thereof, which may be biocompatible. For example, the guidewire or device can be formed from Titanium Grade 23 6Al-4V ELI material or 316 LVM Stainless steel titanium or a titanium alloy. Other suitable metals may include stainless steel, cobalt-chromium alloys, and tantalum. In some embodiments, metal alloys having shape memory capability, such as nickel titanium or spring stainless steel alloys, may also be used. In some embodiments, the guidewire and device can be formed from a suitable polymer including non-degradable polymers, such as polyetheretherketone (PEEK) and polyethylene (PE), as well as modified versions of these materials (for example, PEEK+calcium phosphates and PE+vitamin E, metal coatings, or surface texturing). Additional non limiting polymers may include; polyether-block co-polyamide polymers, copolyester elastomers, thermoset polymers, polyolefins (e.g., polypropylene or polyethylene, including high density polyethylene (HDPEs), low-density polyethylene (LDPEs), and ultrahigh molecular weight polyethylene (UHMWPE)), polytetrafluoroethylene, ethylene vinyl acetate, polyamides, polyimides, polyurethanes, polyvinyl chloride (PVC), fluoropolymers (e.g., fluorinated ethylene propylene, perfluoroalkoxy (PEA) polymer, polyvinylidenefluoride, etc.), polyetheretherketones (PEEKs), PEEK-carbon fiber composites, Polyetherketoneketones (PEKKs), poly(methylmethacrylate) (PMMA), polysulfone (PSU), epoxy resins and silicones. Additionally starch based polymers may be used.

Additional materials may include carbon and polyaramid structures, glass or fiberglass derivatives, ceramic materials, and artificial biocompatible protein derivatives (recombinant derived collagen). In other embodiments, the fracture stabilization device may be made of a metal and/or alloy segments with a polymer shell, or a sandwich style and coaxial extrusion composition of any number of layers of any of the materials listed herein. Various layers may be bonded to each other to provide for single layer composition of metal(s), alloys, and/or polymers. In another embodiment, a polymer core may be used with a metal and/or metal alloy shell, such as a wire or ribbon braid.

Additionally, at least a portion of the device may include a bone integration surface to promote bone ingrowth, on-growth, and/or through-growth between the segments, if desired. The bone integration surfaces can comprise a three-dimensional space to allow bone integration into and/or onto portions of the fracture stabilization device. The three dimensional space can be provided by a three-dimensional substrate, for example beads, and/or by the provision of holes through the bone integration portions. Other methods for achieving bone integration can include the provision of an appropriate surface topography, for example a roughened or textured area and/or by the provision of osteoconductive coatings, such as calcium phosphates. The bone integration surface may enable the fracture stabilization device to provide a metal and/or polymeric scaffold for tissue integration to be achieved through the fracture stabilization device. In various embodiments, various materials may be used to facilitate, stimulate or activate bone growth. A non-limiting list of materials may include hydroxyapatite (HA) coatings, synthetic bioabsorbable polymers such as poly (α-hydroxy esters), poly (L-lactic acid) (PLLA), poly (glycolic acid) (PGA) or their copolymers, poly(DL-lactic-co-glycolic acid) (PLGA), and poly(ε-caprolactone) (PLC), poly(L-lactide) (LPLA), (DLPLA), poly(ε-caprolactone) (PCL), poly(dioxanone) (PDO), poly(glycolide-co-trimethylene carbonate) (PGA-TMC), poly(lactide-co-glycolide), polyorthoesters, poly (anhydrides), polyhydroxybutyrate, poly(l-lactide-co-glycolide) (PGA-LPLA), cyanoacrylates, poly(dl-lactide-co-glycolide) (PGA-DLPLA), poly(ethylene carbonate), poly(iminocarbonates), poly(l-lactide-co-dl-lactide) (LPLA-DLPLA), and poly(glycolide-co-trimethylene carbonate-co-dioxanone) (PDO-PGA-TMC).

EXAMPLES OF THE USE OF THE SUPPORT DEVICE ARE NOW PROVIDED

Example 1: Device Insertion

In an embodiment, the support device has a proximal end, a distal end, and an elongate main body. The proximal end includes a flexibility fixation element that serves to lock the support device into a rigid or inflexible shape when desired. The support device may include an optional sheath to enhance the atraumatic profile of the support device when used. After the patient is properly prepared and oriented so the surgeon, doctor or other medical professional can access the desired location of the body, the trocar 3204 can be assembled with a protective sleeve 3202 to access the pelvis P. The assembled protective sleeve 3202 and trocar 3204 are used to pass through soft tissue to the desired entry point E on the bone. When the trocar and protective sleeve assembly are properly placed, a user may strike the trocar with a hammer, cannulated hammer or other instrument 3206 to create a starting point in the bone for the procedure (FIGS. 32A-L). In this example, the pelvis P has suffered a break B in two locations. The break in the Sacrum is not treated in this example.

A start drill 3208 or similar device may be inserted through the protective sleeve 3202 and advanced through the cortical bone. This creates a portal for all instruments and devices to pass through as they enter the bone P (FIG. 32B).

The start drill may be removed and a steerable guide wire, guide pin or CIF steerable guide wire (collectively simply referred to herein as a "guidewire" 3210) may be inserted through the protective sleeve 3202 and the trocar 3204. A physician or other medical professional may use fluoroscopy or other visualization technology to view the guidewire in the bone. The CIF guidewire is advanced through the medullary canal. By Rotating the CIF steerable Guidewire and applying force on the proximal end, a desired placement can be achieved. The guidewire is advanced to the proximity of the cortical wall of the Pubis symphysis and across the break B (FIG. 32C).

Figure 32A:
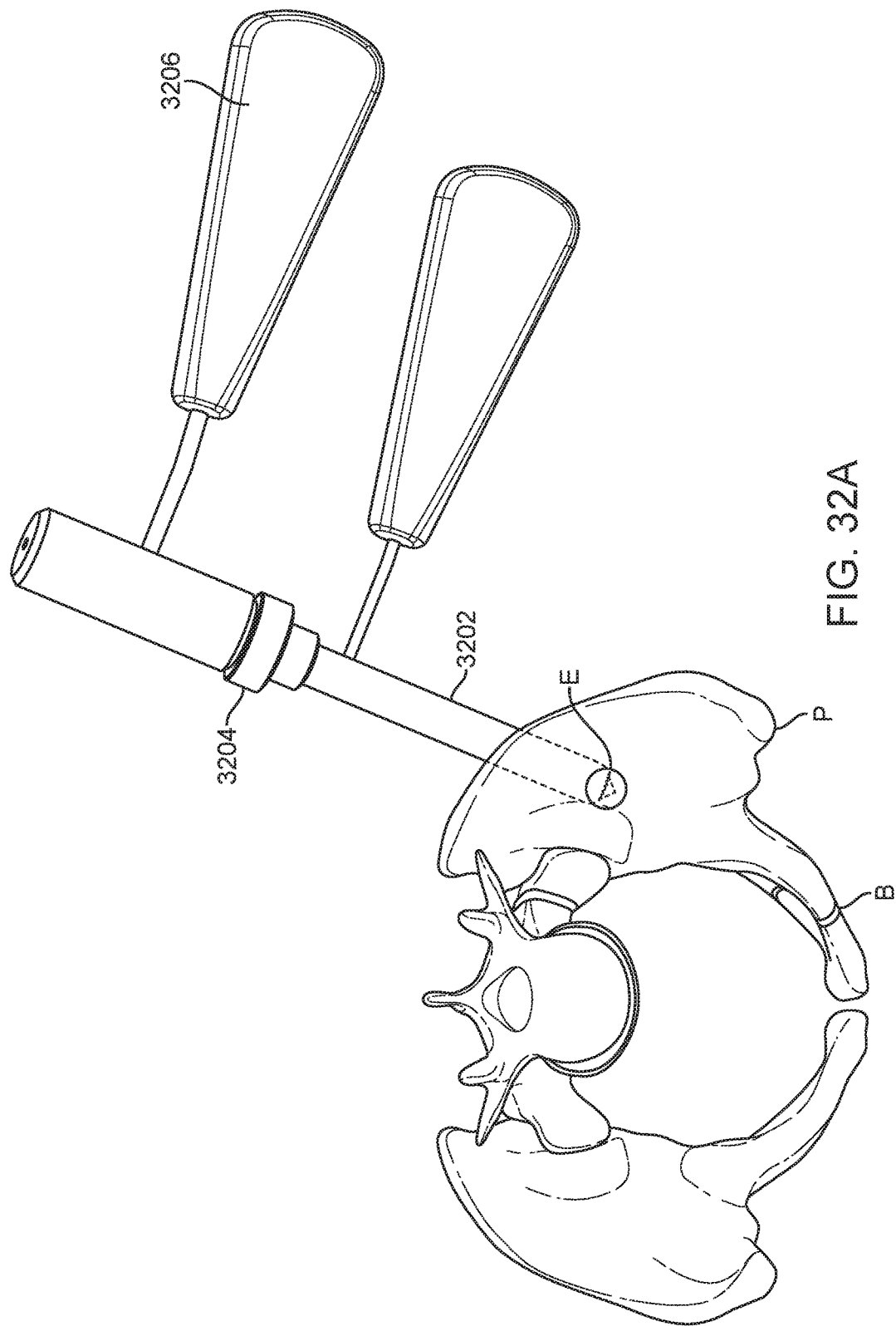
Figure 32D:
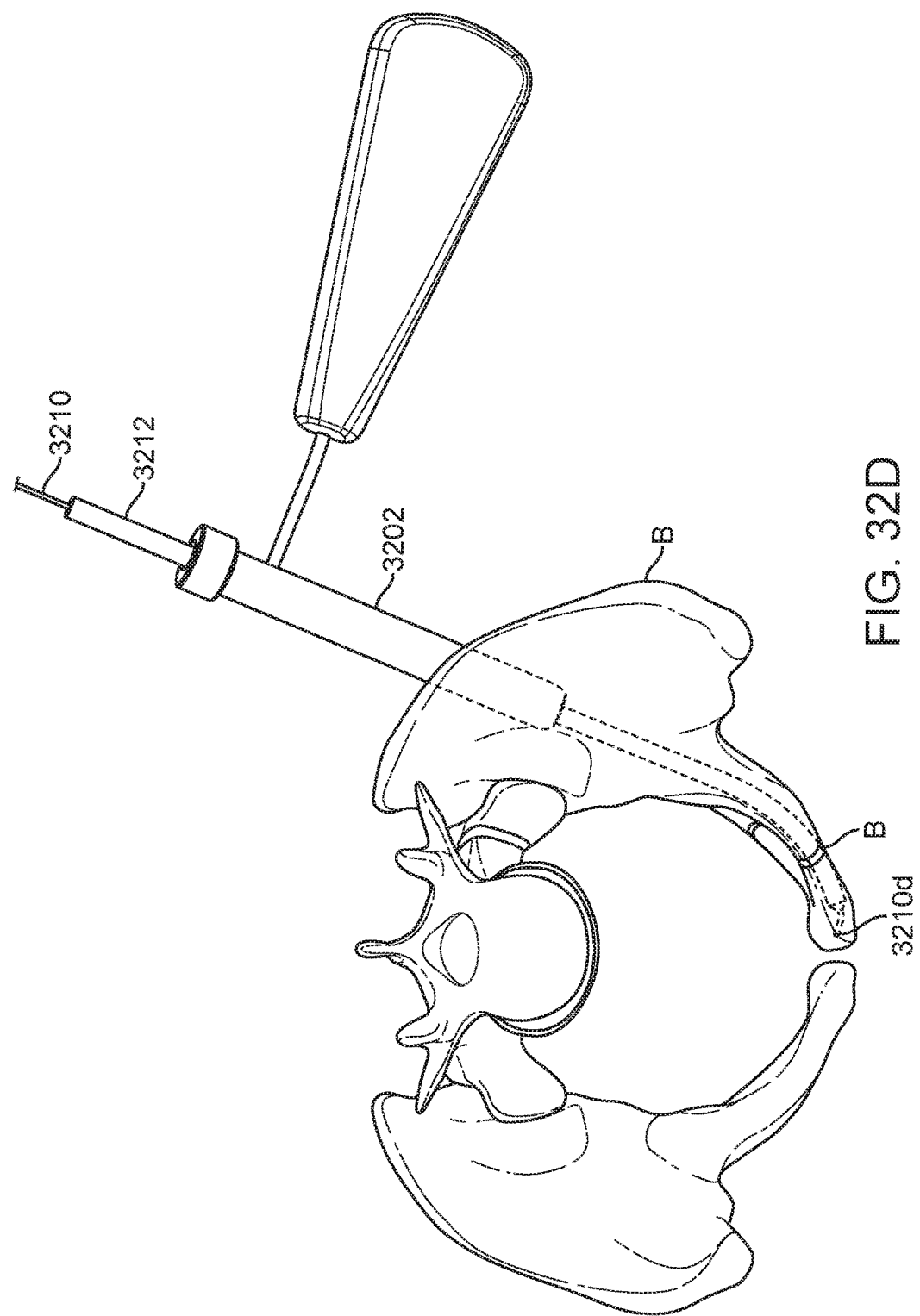

Once the medical professional is satisfied with the placement of the CIF steerable guidewire 3210, a cannulated flexible reamer 3212 may be passed over the guidewire and used to ream the cancellous bone. The surgeon should exercise care not to ream through the bone past the distal end of the guidewire 3210d (FIG. 32D).

Figure 32E:
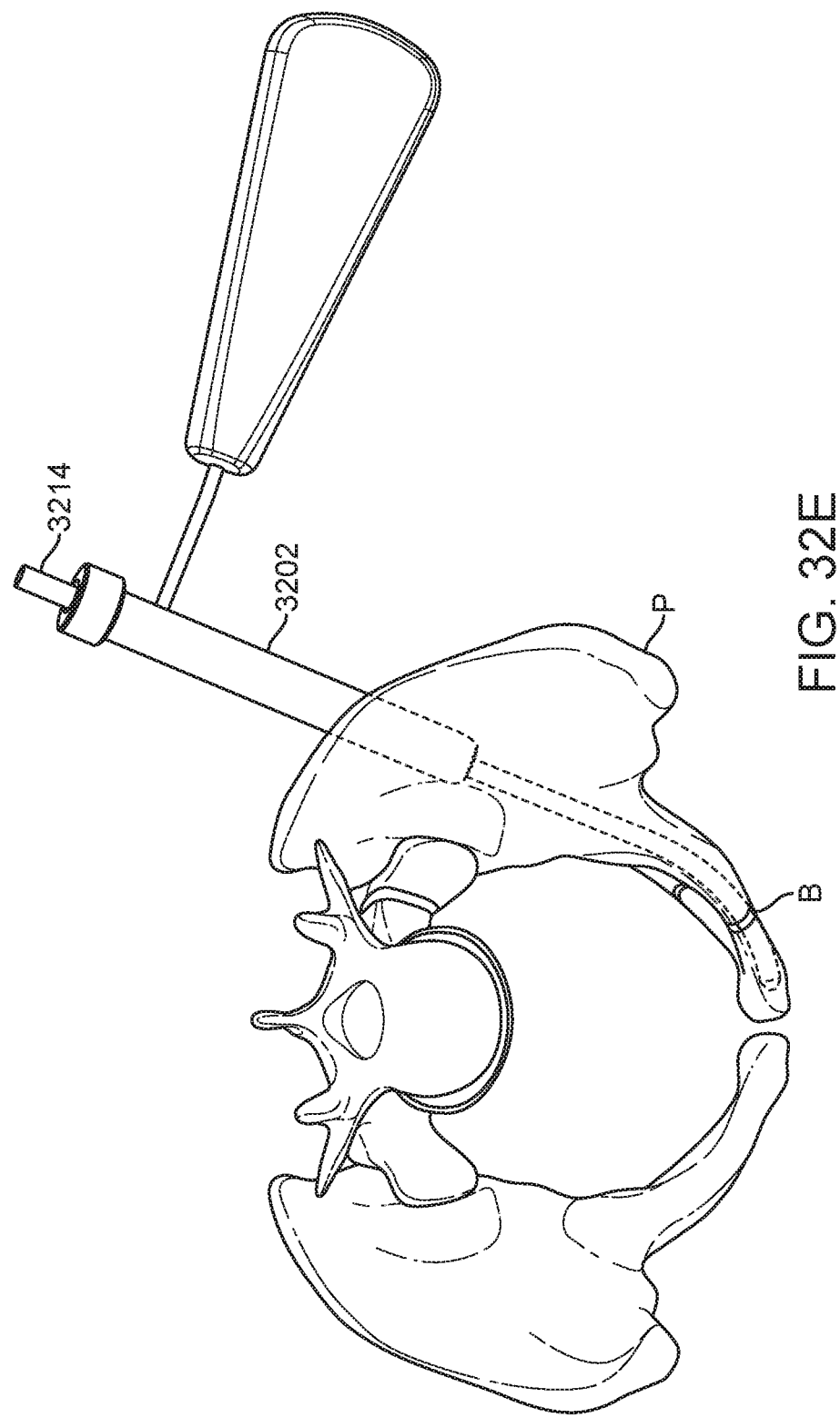

When the medical professional is satisfied the reaming is completed, the reamer tool and the guidewire are both removed. A directional exchange tool 3214 is introduced through the protective sleeve 3202 and into the recently reamed channel in the medullary canal. It may be useful to place the cone shaped geometry of the directional exchange tool adjacent to, and as normal as possible to, the cortical wall (FIG. 32E). A trocar tipped guidewire 3216 is then passed through the directional exchange tool 3214. The trocar tipped guidewire 3216 is placed down to the cortical wall CW (FIG. 32F). The user than applies force, either manually or via some mechanical advantage device) on the proximal end of the trocar tipped guidewire 3216 until both cortices of the Pubis Symphysis have been perforated (FIG. 32G).

Figure 32H:
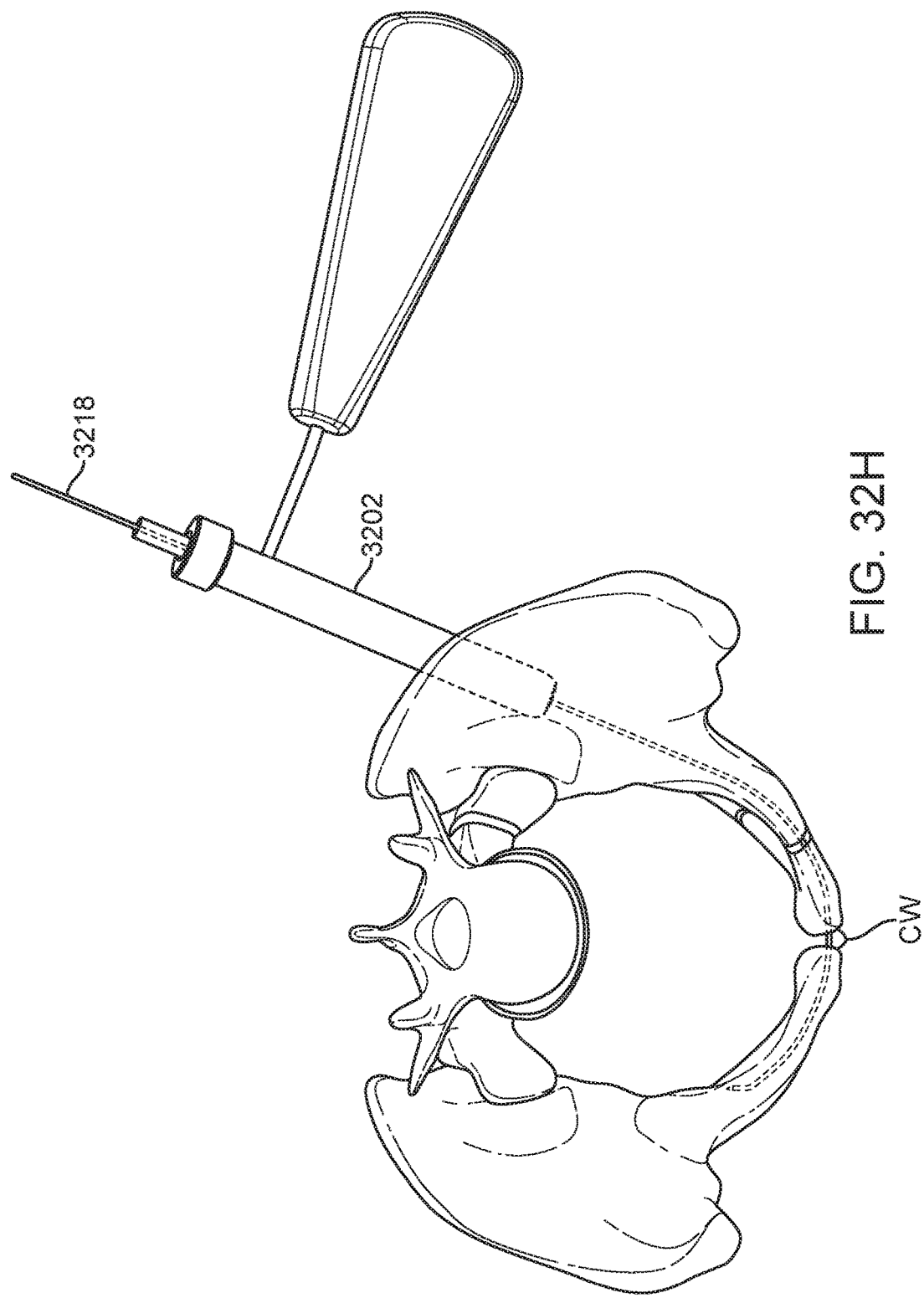
Figure 32I:
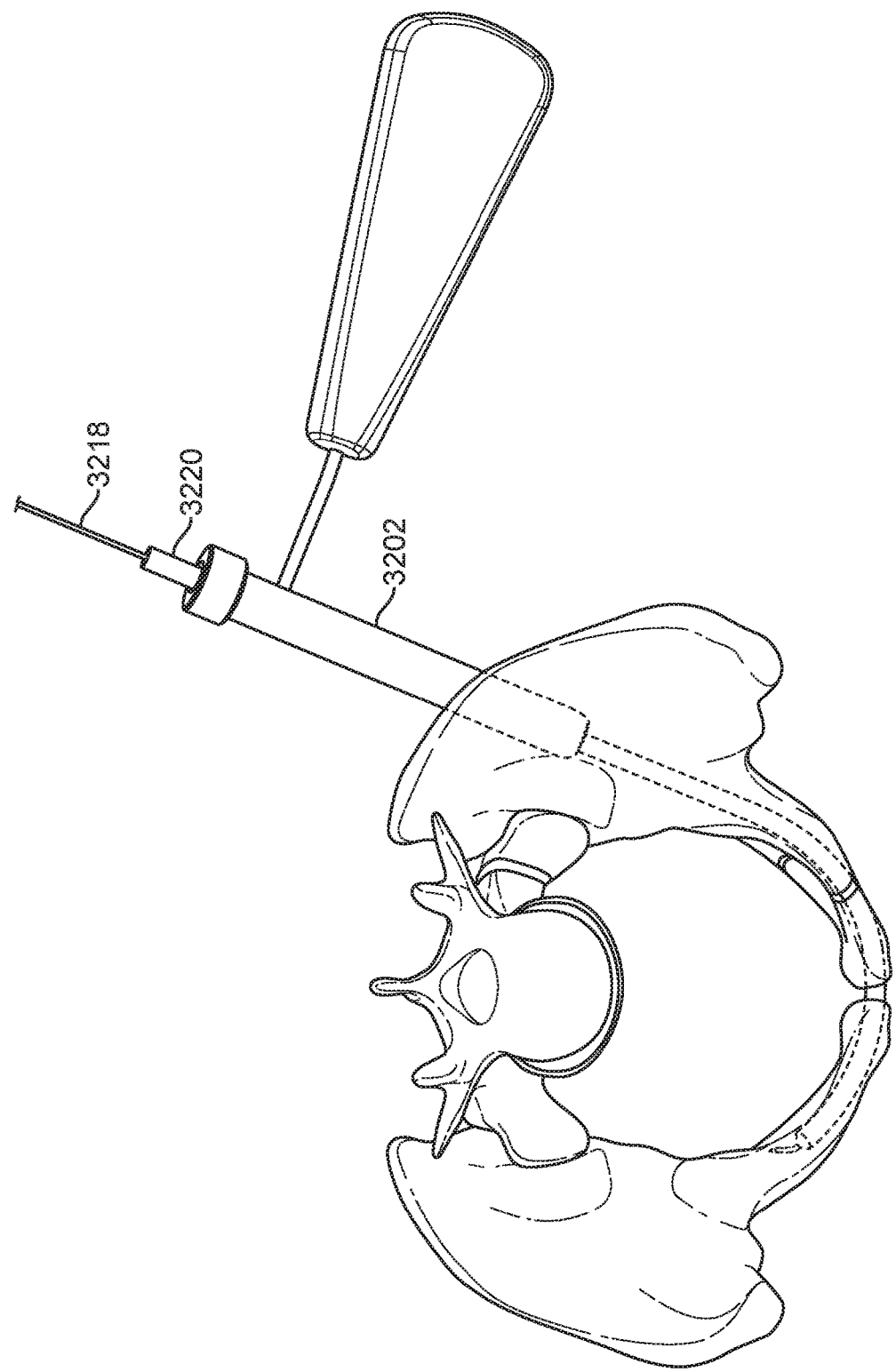

Once both cortices have been pierced, the trocar tipped guidewire is removed and a second steerable guidewire 3218 is introduced. If the perforations in the cortical wall CW are not large enough, it may be necessary to ream the holes out until they are sufficiently large to accommodate the passing of the guidewire. The medical professional then crosses the guidewire to the Pubis Symphysis and medullary canal across the pubic arch (FIG. 32H). A reamer 3220 is used to finish creating the path between the two side of the pubic arch (FIG. 32I).

Figure 32K:
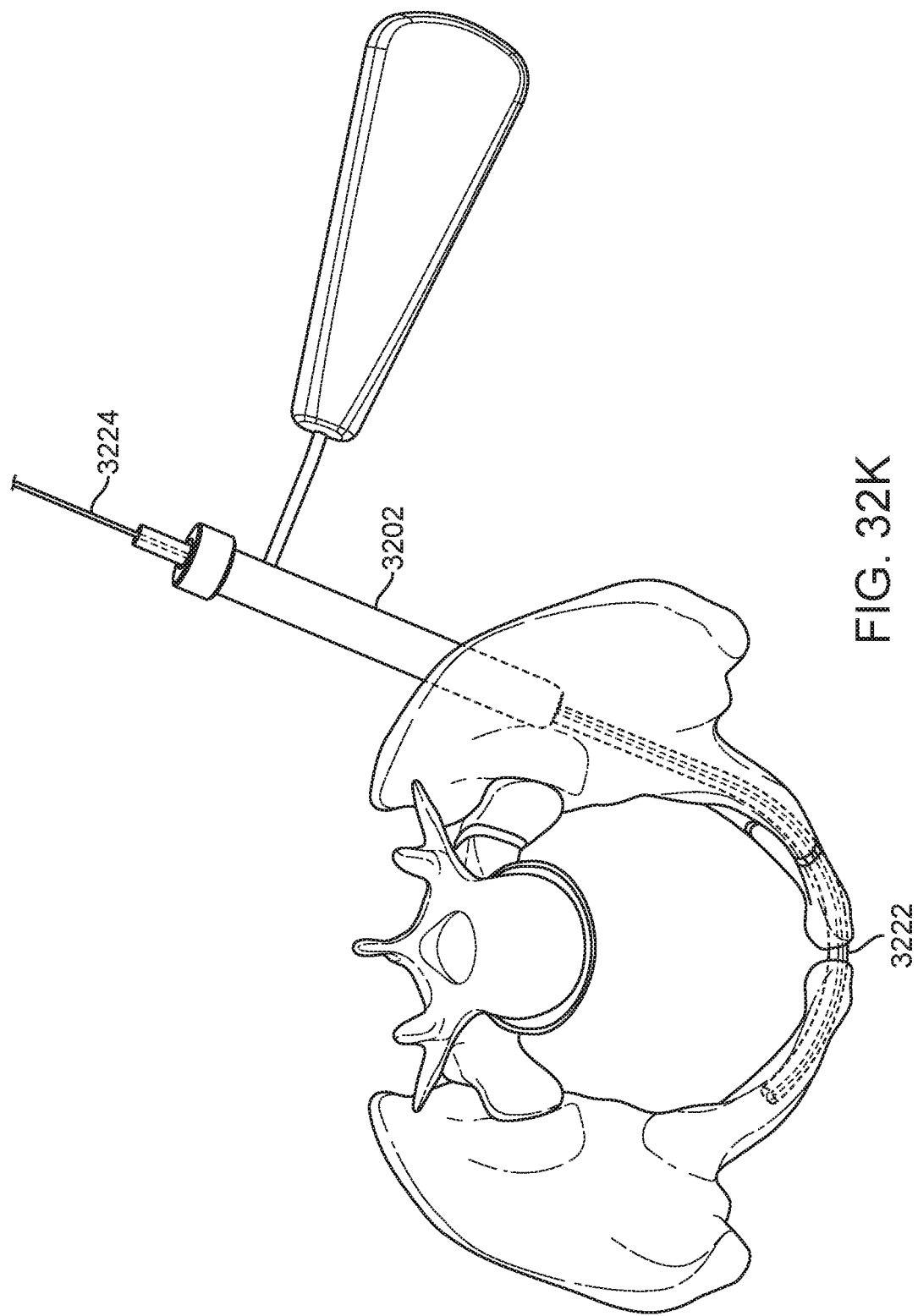
Figure 32L:
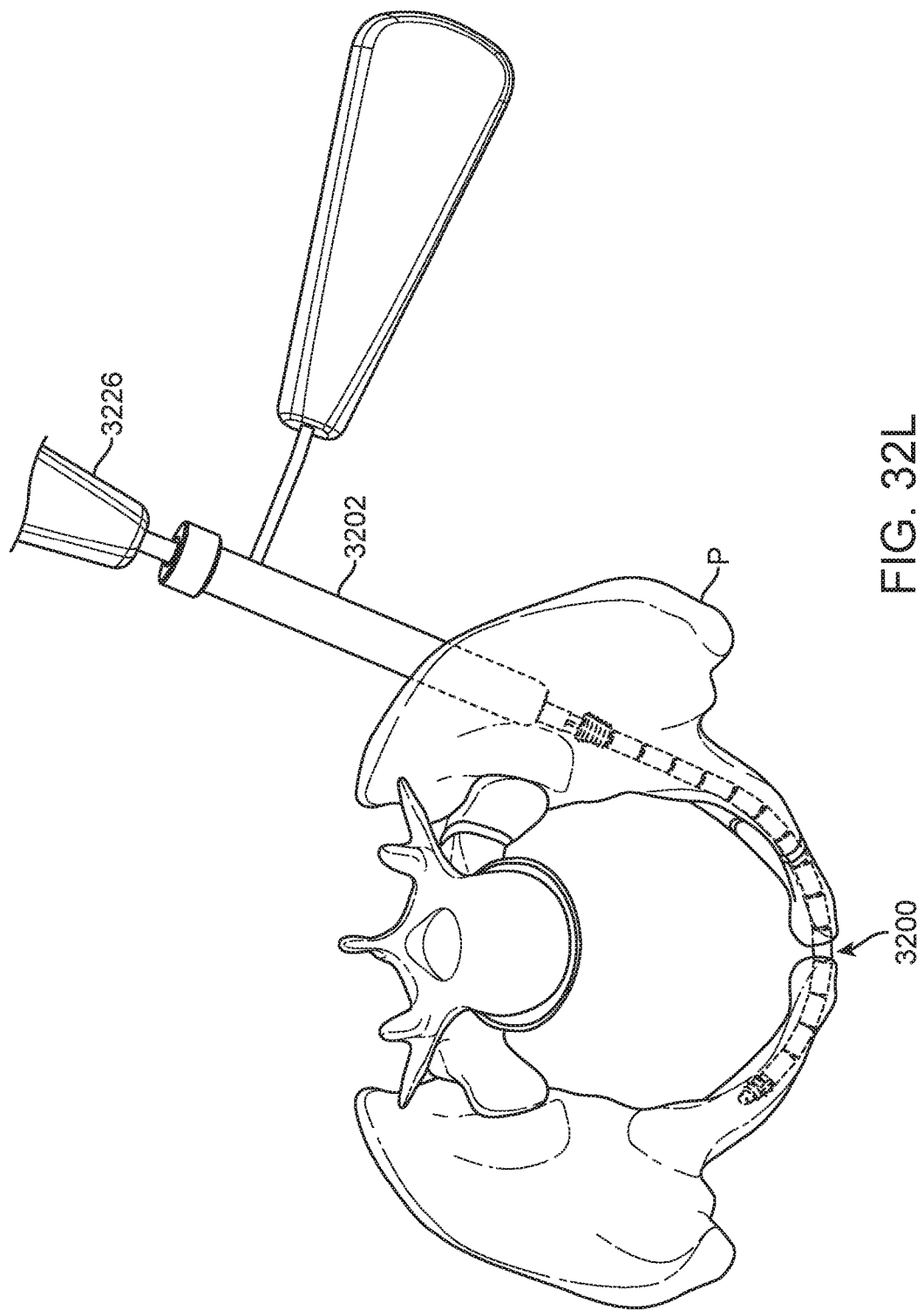

When the reaming is completed, the medical professional can introduce an exchange tube 3222 over the guidewire 3218. The exchange tube 3222 is then advanced over the guidewire to the distal end of the guidewire (FIG. 32J). Once the exchange tube 3222 is properly placed, the guidewire may be removed and a trocar tipped guidewire 3224 is introduced and advanced to approximately the same distal location. The exchange tube 3222 can then be removed (FIG. 32K). The device 3200 can now be advanced over the guidewire 3224. The device 3200 may need to be advanced using any appropriate torque driver 3226, such as a hexalobe driver, screw driver or drill tool to name a few. Once the device is properly placed across the break B and the pubic arch, the shape device can be secured in place by drawing tight any fibers in the device to secure the position of the segments, or simply deploying a proximal end with a bone engagement element to secure the device 3200 in the bone (FIG. 32L).

The device has a distal end which is rounded and oblong with a screw thread designed to help cut into the bone structure when the support device is deployed. The shape of the distal end may be adapted for a variety of different types of bones and bone densities. The shape and design of the distal end should be adaptive to not overly stress weaker bones (such as in patients who are elderly and may suffer from osteoporosis). Similarly the shape, thread pitch and cutting edge should be adapted for stronger bones if the support device is to be placed into the bone of someone younger and healthy (such as an athlete).

Example 2: Surgical Procedure for Fixation of Pelvic Fracture

The device may be used to stabilize fractures in the iliosacral area posteriorly, the anterior column of the acetabulum, the superior pubic ramus, the posterior column of the acetabulum, the pubic symphysis as well as other areas. The device may be adapted for use in ribs, the sternum, collar bones, shoulder blades or even long bones of the body.

The procedure used to treat bones can be generically thought of to follow and be similar to, the procedure to insert cannulated cancellous screws in some areas (but not all). The curved intramedullary device is not a reduction device and as with the use of cannulated screws, the surgeon generally should reduce the fracture and temporarily stabilize it before employing the current device. The device can secure the pubic rami and the symphysis at the same time. In an example procedure, the patient would be placed supine on a radiolucent operating table and prepped and draped exposing the entry points chosen for the particular procedure. For example, for a vertical shear type of pelvic fracture with disruption through the sacrum at the back and the pubic ramus at the front, the pubic area and the posterolateral buttock area would be exposed.

After the fracture is reduced and temporarily held by whatever method the surgeon needs, a small incision is made of the pubic tubercle on the affected side and the lateral side of the tubercle exposed. A small hole of about 2-5 mm (millimeters) is drilled through the cortex in the middle of the lateral side of the tubercle and a special curved guidewire is introduced into the medullary space of the superior pubic ramus. Using the image intensifier as a guide and using appropriate imaging views, the guide wire is advanced, not by drilling, but by hammering. Alternative embodiments advance the wire by drilling. Another alternative embodiment has a guidewire which has a drill feature incorporated into its distal end to facilitate drilling through the bone (which may be either cancellous or cortical).

The hammering of the guidewire can be done with a standard hammer or a hammer drill. The wire is carefully advanced inside the pubic ramus and the anterior column, past the acetabulum staying inside the bone. The length of the wire inside the bone is measure and an appropriate length of curved intramedullary device is chosen. A flexible reamer of 8.5 mm is placed over the guidewire and drilled in, again under fluoro control, making a tunnel in the bone. Using an exchange tube, the sharp bent tipped guidewire is exchanged for a blunt tipped guidewire. The reamer and guidewire are removed and the chosen curved intramedullary device is screwed into the tunnel over the guidewire using a torque driver.

Because the device is flexible, it is easier to insert it through a cannula. Once in place, one embodiment has a star shaped screwdriver used to tighten then tensioning wire and compress the elements of the device together to make them rigid. A capping nut is then applied to the proximal end to add mild compression and to prevent the bone from slipping off the end of the device. Once in place, the device is made rigid.

Example 3

Attention is then directed posteriorly, the surgeon chooses a starting point on the lateral surface of the ilium above the sciatic notch. The starting point is not quite as critical as it is in using a cannulated screw since the guidewire follows a curved path of the surgeon's choosing and the path can be modified in situ more easily than can the path of a straight wire. Because of the bulk of the soft tissue of the buttock, this procedure would be done through a series of stacked cannulae.

Example 4

The procedure is then the same as described for the anterior fixation. A hole is drilled at the desired access point, and a curved guidewire is hammered across the SI joint and across the body of the sacrum through SI and if needed across the far SI joint in the ilium, measuring, reaming, guidewire exchange, insertion of the device and tightening of the tension fibers of the device. It may be needed to tighten the wires/fibers of the anterior and anterior devices at the same time, or in synchronized fashion, to be sure that tightening one does not move the fracture in the other site. Once the device is in place, the wounds are closed, final X-rays are taken and dressings are applied.

Example 5

Alternative embodiments include a flexible/rigid device (as described herein) to fixate an anterior pelvic fracture along with conventional screws or plates to fixate a posterior fracture.

Example 6

Another alternative embodiment includes a flexible/rigid device (as described herein) to fixate a posterior pelvic fracture along with conventional screws or plates to fixate an anterior fracture.

Example 7: Device Removal

In an embodiment, the support device may need to be removed after implantation. This may be referred to as explanation or simply removal. In this embodiment the operator must once again access the entry site on the bone that was previously treated with the flexible support device. The proximal bone interface may be rotated off, or removed in the appropriate manner to expose the shape locking element. The shape locking element is engaged with a tool that can disengage the shape locking mechanism in a manner that will allow the support device to return to a flexible state. The support device is then removed from the bone. If the support device was "screwed" in, it can be rotated in the opposite direction and unscrewed from the bone. The tool may interface with either the proximal end, the shape locking element, or other readily accessible feature on or near the proximal end. It may be necessary to remove some bone ingrowth from the support device in order to gain sufficient access to the implanted support device when removal is desired.

Rotation of the proximal end of the device transmits torque through the support device up to the distal bone interface. The torsional response of the main body sections may result in a section by section disengagement with any bone ingrowth. The most proximal section is likely to break free first, with the segments breaking free in sequence down to the most distal end. It is also possible that entire sections will break free at once, or the device will break free all together. When the support body has broken free of the bone ingrowth, the support body may be removed.

Embodiments

1. A medical apparatus for bone fixation, the apparatus comprising:
   a flexible body defining a main axis, the flexible body having a proximal end and a distal end, the flexible body comprising:
      a plurality of individual segments having a mechanical engagement structure for non-rigidly interlocking the individual segments together;
      a plurality of apertures in each individual segment, the apertures arranged to generally form a plurality of lumens in the flexible body when the segments are in non-rigid mechanical engagement;
      wherein the individual segments may move relative to each other in a first and a second orthogonal plane relative to the main axis;
   a torque transmission member positioned substantially on the proximal end;
   a bone engagement feature positioned substantially on the distal end; and
   a plurality of fibers extending through the lumens such that the fibers provide a fixed shape to the flexible body when the fibers are fixed into position.

2. The apparatus of embodiment 1, wherein the individual segments possess a first and a second end, the first end having a mechanical engagement structure (male end) and the second end having a shaped receptacle for receiving a similarly shaped mechanical engagement structure (female end) such that the interconnection between the mechanical engagement structure and the shaped receptacle forms a mechanical interlock allowing movement between the mechanically engaged individual segments.

3. The apparatus of embodiment 2, wherein the mechanical engagement structure operates as a fulcrum.

4. The apparatus of embodiment 2, further comprising a second mechanical engagement structure.

5. The apparatus of embodiment 2, further comprising a second shaped receptacle.

6. The apparatus of embodiment 1, wherein the flexible body is sub-divided into sections.

7. The apparatus of embodiment 4, wherein each section comprises one or more segments.

8. The apparatus of embodiment 1, wherein said fibers are of two or more individual lengths when drawn taut.

9. The apparatus of embodiment 1, wherein the individual segments are not of uniform size, shape, mass or length.

10. The apparatus of embodiment 1, wherein the individual mechanical engagement structures are not uniform from segment to segment.

11. The apparatus of embodiment 1, wherein the individual shaped receptacles are not uniform from segment to segment.

12. The apparatus of embodiment 1, further comprising a sheath extending over the flexible body.

13. The apparatus of embodiment 1, wherein the fibers are mechanically fixed into position.

14. The apparatus of embodiment 1, wherein the fibers are chemically fixed into position.

15. A medical apparatus for bone fixation, the apparatus comprising:
   An elongate tubular body defining a first axis, the body having a proximal end, a distal end and a lumen there through, the tubular body having a plurality of apertures;
   a torque transmission member located substantially at the proximal end;
   a bone engagement feature located substantially at the distal end;
      wherein the plurality of apertures provide stress relief along the elongate body when the tubular body is under torque.

16. A medical apparatus of embodiment 15, further comprising a stiffening member within the lumen.

17. A medical apparatus of embodiment 16, wherein the stiffening member is a spring.

18. A medical apparatus as in embodiment 16, wherein the stiffening member is a single rigid member.

19. A medical apparatus as in embodiment 15, where a chemical compound causes radial expansion of the tubular body.

20. A medical apparatus for fixation of fractured bone, the apparatus comprising:
   an elongated body defining a longitudinal axis, and having a proximal end and a distal end spaced longitudinally from the proximal end by a first distance, the body comprising:
      a flexible body portion extending along at least a portion of the first distance, the flexible body portion comprising a plurality of interconnected segments, wherein each segment of the interconnected segments defines an axis portion of the longitudinal axis, and each segment is movable with respect to at least one adjacent segment to angularly offset the axis portion of each segment with the axis portion of the at least one adjacent segment;
   a transmission member positioned adjacent the proximal end for axially inserting the elongated body into the bone;
   a bone engagement device positioned adjacent the distal end for axially retaining the elongated body within the bone;
   a plurality of cables disposed longitudinally within the elongated body through at least the flexible body portion in circumferentially spaced relation to one another; and
   a cable tensioning system for tensioning individual ones of the plurality of cables to retain the interconnected segments in a fixed relationship with each of the plurality of cables and with one another.

21. The medical apparatus of embodiment 20, wherein:
   the plurality of interconnected segments comprises a plurality of individual interconnected segments; and
   each individual segment having a first end and a second end spaced axially from the first end; and
   at least one of the first end and the second end of each segment comprises a first engagement portion for pivotally engaging with the other of the first end and the second end of an adjacent segment to angularly offset the axis portion of the segment with the axis portion of the at least one adjacent segment.

22. The medical apparatus of embodiment 21, wherein:
the first engagement portion comprises a protrusion extending axially from the first end; and
the other of the first end and the second end comprises a recessed portion for receiving the protrusion therein.

23. A method of fixing a reduced bone fracture in a curved bone, the method comprising:
creating an entry into a curved bone;
advancing a guidewire through an intramedullary space to a position distal to a reduced bone fracture;
reaming a channel in the intramedullary space along the length of the guidewire;
advancing a curved intramedullary fixation device through the channel; and
locking the curved intramedullary fixation device in place.

What is claimed is:

1. A method, comprising:
inserting a guidewire into an intramedullary space of a bone having a fracture;
advancing the guidewire through the intramedullary space to a position distal to the fracture;
advancing an intramedullary fixation device in a flexible configuration along a curved pathway over the guidewire such that the device conforms to the curved pathway as it is advanced; and
locking the intramedullary fixation device in a rigid curved configuration to fixate the bone fracture by prohibiting at least two flexible members extending axially within the intramedullary fixation device from moving relative to one another in an axial dimension, wherein prohibiting movement of the flexible members relative to each other increases the rigidity of the device in the rigid curved configuration relative to the rigidity of the device in the flexible configuration.

2. The method of claim 1, wherein the bone comprises a curved bone.

3. The method of claim 2, wherein the curved bone is a bone of a pelvis.

4. The method of claim 1, wherein the flexible members are movable relative to each other in the axial dimension while the intramedullary fixation device is in the flexible configuration.

5. The method of claim 1, wherein:
the intramedullary fixation device comprises a plurality of individual segments each having a mechanical engagement structure configured for interlocking individual segments together;
each of the plurality of individual segments comprises a respective hollow core at a respective center of the individual segment; and
advancing the intramedullary fixation device comprises advancing the intramedullary fixation device over the guidewire such that the guidewire extends through the hollow core of each individual segment of the plurality of individual segments.

6. The method of claim 5, wherein:
each of the plurality of individual segments further comprises at least two apertures distributed circumferentially around the hollow core of the respective individual segment to generally form at least two lumens in the intramedullary fixation device; and
the intramedullary fixation device further comprises, as the at least two flexible members, at least two fibers that extend through the at least two of lumens, and wherein locking the intramedullary fixation device comprises fixing each of the at least two fibers into a respective position relative to each of the other ones of the at least two fibers.

7. The method of claim 6, wherein respective fibers of the at least two fibers pass through different apertures of the at least two apertures.

8. The method of claim 6, wherein fixing the at least two fibers into position relative to each other comprises mechanically fixing the at least two fibers into position at a proximal end of the device with an end cap.

9. The method of claim 6, wherein locking the intramedullary fixation device comprises tensioning the at least two fibers prior to fixing each of the at least two of fibers into a respective position relative to each of the other ones of the at least two fibers.

10. The method of claim 1, wherein, during the advancing the intramedullary fixation device over the guidewire, the plurality of individual segments are mechanically interlocked such that the individual segments are able to move relative to each other in a first plane and a second plane, and wherein the first plane and the second plane are orthogonal relative to a main axis defined along the guide wire.

11. The method of claim 10, wherein immediately adjacent individual segments are able to move relative to each other in the first plane and the second plane during the advancing the intramedullary fixation device over the guidewire.

12. The method of claim 1, wherein advancing the intramedullary fixation device over the guidewire comprises applying a torque driver to a torque transmission engagement feature positioned substantially on a proximal end of the intramedullary fixation device to rotate the intramedullary fixation device.

13. The method of claim 1, wherein:
the flexible members extend from a proximal region of the intramedullary fixation device to a distal region of the device; and
the intramedullary fixation device conforms to the curved pathway in the flexible configuration by permitting a region of the device disposed between the proximal region and the distal region to flex in response to the device being advanced along the curved pathway.

14. The method of claim 1, further comprising:
advancing another guidewire through the intramedullary space;
passing a reaming device over the other guidewire;
reaming cancellous bone with the reaming device to create a reamed channel; and
removing the other guidewire and the reaming device from the intramedullary space.

15. The method of claim 14, wherein advancing the guidewire through the intramedullary space to the position distal to the fracture comprises advancing the guidewire through the reamed channel.

16. The method of claim 1, wherein the advancing the intramedullary fixation device comprises screwing the intramedullary fixation device into the bone.

17. The method of claim 1 wherein advancing the guidewire comprises advancing the guidewire from the intramedullary space of the bone to an intramedullary space of another bone.

18. The method of claim 17 wherein the bone is one side of a pubic arch and the other bone is another side of the pubic arch.

19. The method of claim 1 wherein locking the intramedullary fixation device includes causing a length of one of the least two flexible members between two locations of the intramedullary fixation device to be different than a respective length between the two locations of at least one other one of the at least two flexible members.

20. The method of claim 1 wherein locking the intramedullary fixation device includes causing a length of one of the least two flexible members between a member-fixation location and a member-lock location of the intramedullary fixation device to be different than a respective length of at least one other one of the at least two flexible members between the member-fixation and the member-lock locations.

21. A method, comprising:
inserting a guidewire into an intramedullary space of a bone along a curved path that spans a fracture of the bone;
advancing an intramedullary fixation device over the guidewire such that the device acquires a curved shape that corresponds to the curved path;
removing the guidewire such that the intramedullary fixation device retains the curved shape after the guidewire is removed; and
fixating the fracture with the intramedullary fixation device in the curved shape after the guidewire is removed by prohibiting axial movement of a flexible member of the device relative to another flexible member of the device, the flexible member and the other flexible member each extending axially from a proximal region of the device, through a curved through a curved middle region of the device, to a distal region of the device.

22. The method of claim 21, wherein the intramedullary space comprises a curved intramedullary space.

23. A method, comprising:
advancing an intramedullary fixation device through a curved intramedullary space of a fractured bone, wherein the intramedullary fixation device comprises a plurality of individual segments each having a mechanical engagement structure for interlocking individual segments together, and wherein the intramedullary fixation device is in a flexible state while advancing the intramedullary fixation device through the curved intramedullary space such that adjacent individual segments can move relative to each other;
shape locking the intramedullary fixation device into a rigid state and curved shape to fixate the bone fracture;
wherein each of the plurality of individual segments comprises a plurality of apertures distributed circumferentially around the respective individual segment to generally form a plurality of lumens extending longitudinally through the individual segment;
wherein the intramedullary fixation device further comprises a plurality of fibers extending through the plurality of lumens of each of the individual segments; and
wherein shape locking the intramedullary fixation device comprises fixing each of the plurality of fibers in a respective position relative to the other fibers.

24. The method of claim 23, further comprising:
wherein each of the plurality of individual segments comprises a hollow core at a center of each respective individual segment; and
advancing the intramedullary fixation device over a guidewire such that the guidewire extends through the hollow core of each individual segment of the plurality of individual segments.

25. A method, comprising:
advancing an intramedullary fixation device in a flexible state along a curved pathway in an intramedullary space of a bone having a fracture to a position distal to the fracture such that the device conforms to the curved pathway as the device is advanced by allowing at least two flexible members disposed within the intramedullary fixation device to move relative to one another in an axial dimension of the device; and
locking the intramedullary fixation device into a rigid state in a curved configuration to fixate the bone fracture by prohibiting the at least two flexible members from moving relative to one another in the axial dimension, wherein the device has a rigidity in the rigid state that is greater than the rigidity of the device in the flexible state.

26. The method of claim 25, further comprising:
advancing a guidewire through the intramedullary space such that the guidewire spans the bone fracture; and
wherein advancing the intramedullary fixation device includes advancing the intramedullary fixation device over the guidewire.

27. A method, comprising:
advancing an intramedullary fixation device in a flexible state along a curved pathway in an intramedullary space of a bone having a fracture such that the device conforms to the curved pathway as it is advanced and such that the device spans the fracture; and
causing the intramedullary fixation device to be curved in a rigid state to fixate the fracture by prohibiting at least two radially adjacent flexible members extending axially within the intramedullary fixation device from sliding past one another.

28. The method of claim 27, further comprising:
advancing a guidewire through the intramedullary space such that the guidewire spans the bone fracture; and
wherein advancing the intramedullary fixation device includes advancing the intramedullary fixation device over the guidewire.

* * * * *